United States Patent
Lally et al.

(10) Patent No.: US 7,619,731 B2
(45) Date of Patent: Nov. 17, 2009

(54) MEASURING A DAMAGED STRUCTURE FORMED ON A WAFER USING OPTICAL METROLOGY

(75) Inventors: Kevin Lally, Austin, TX (US); Merritt Funk, Austin, TX (US); Radha Sundararajan, Dripping Springs, TX (US)

(73) Assignee: Tokyo Electron Limited (JP)

( * ) Notice: Subject to any disclaimer, the term of this patent is extended or adjusted under 35 U.S.C. 154(b) by 339 days.

(21) Appl. No.: 11/396,210

(22) Filed: Mar. 30, 2006

(65) Prior Publication Data

US 2007/0229806 A1    Oct. 4, 2007

(51) Int. Cl.
 *G01N 21/00* (2006.01)
(52) U.S. Cl. ................................. 356/237.5; 702/76
(58) Field of Classification Search ... 356/237.1–237.5, 356/445, 630–632, 601; 700/109, 110, 121; 702/76
See application file for complete search history.

(56) References Cited

U.S. PATENT DOCUMENTS

| | | | |
|---|---|---|---|
| 5,903,342 A | 5/1999 | Yatsugake et al. | |
| 6,384,909 B2 | 5/2002 | Tomita et al. | |
| 6,591,405 B1 | 7/2003 | Doddi | |
| 6,608,690 B2 | 8/2003 | Niu et al. | |
| 6,661,515 B2 | 12/2003 | Worster et al. | |
| 6,694,275 B1 | 2/2004 | Jakadar et al. | |
| 6,743,646 B2 | 6/2004 | Jakatdar et al. | |
| 6,768,983 B1 | 7/2004 | Jakatdar et al. | |
| 6,785,638 B2 | 8/2004 | Niu et al. | |
| 6,818,459 B2 | 11/2004 | Wack et al. | |
| 6,829,559 B2 | 12/2004 | Bultman et al. | |
| 6,839,145 B2 | 1/2005 | Niu et al. | |
| 6,853,942 B2 | 2/2005 | Drege et al. | |
| 6,891,626 B2 | 5/2005 | Niu et al. | |
| 6,928,395 B2 | 8/2005 | Niu et al. | |
| 6,943,900 B2 | 9/2005 | Niu et al. | |
| 6,947,141 B2 | 9/2005 | Bischoff et al. | |
| 6,979,823 B2 | 12/2005 | Shinada et al. | |
| 6,989,899 B2 | 1/2006 | Salnik et al. | |
| 7,006,235 B2 | 2/2006 | Levy et al. | |
| 7,046,375 B2 | 5/2006 | Bischoff et al. | |
| 7,072,049 B2 | 7/2006 | Niu et al. | |
| 7,235,414 B1 | 6/2007 | Subramanian et al. | |
| 7,324,193 B2* | 1/2008 | Lally et al. ............... | 356/237.2 |
| 2003/0198895 A1 | 10/2003 | Toma et al. | |
| 2004/0017574 A1 | 1/2004 | Vuong et al. | |
| 2004/0017575 A1* | 1/2004 | Balasubramanian et al. | 356/625 |
| 2004/0117055 A1 | 6/2004 | Seidel et al. | |

(Continued)

OTHER PUBLICATIONS

Machavariani, V. et al. (2002). "Scatterometry—Interpretation by Different Methods of Electromagnetic Simulation," *Proceedings of SPIE-Metrology, Inspection, and Process Control for Microlithography XVI* 4689:177-188.

(Continued)

*Primary Examiner*—Hoa Q Pham

(57) ABSTRACT

A method of measuring a damaged structure formed on a semiconductor wafer using optical metrology includes directing an incident beam on the damaged structure. A diffracted beam is received from the damaged structure. The received diffracted beam is processed to determine a profile of an undamaged portion of the damaged structure and to measure an amount of dielectric damage of the damaged structure.

18 Claims, 23 Drawing Sheets

U.S. PATENT DOCUMENTS

| | | | |
|---|---|---|---|
| 2004/0181304 A1 | 9/2004 | Collier | |
| 2004/0218192 A1* | 11/2004 | Bischoff et al. | 356/600 |
| 2004/0267397 A1 | 12/2004 | Doddi et al. | |
| 2005/0057748 A1 | 3/2005 | Vuong et al. | |
| 2005/0077597 A1 | 4/2005 | Toma et al. | |
| 2005/0215072 A1 | 9/2005 | Kevwitch et al. | |
| 2007/0077782 A1 | 4/2007 | Lee et al. | |
| 2007/0232045 A1* | 10/2007 | Lally et al. | 438/597 |
| 2007/0233404 A1* | 10/2007 | Lally et al. | 702/35 |
| 2008/0137078 A1* | 6/2008 | Lally et al. | 356/237.2 |

OTHER PUBLICATIONS

International Search Report and Written Opinion mailed Feb. 13, 2008, for PCT Application No. PCT/US07/08018 filed Mar. 29, 2007, 10 pages.

International Search Report and Written Opinion mailed Feb. 14, 2008, for PCT Application No. PCT/US07/07934 filed Mar. 29, 2007, 8 pages.

International Search Report and Written Opinion mailed Feb. 20, 2008, for PCT Application No. PCT/US07/08264 filed Mar. 29, 2007, 10 pages.

Stover, J. C. (1995). Optical Scattering-Measurement and Analysis, Second Edition, SPIE-The International Society for Optical Engineering: Bellingham, Washington, 5 pages (Table of Contents).

Moharam, M. G. et al. (May 1995). "Stable Implementation of the Rigorous Coupled-Wave Analysis for Surface-Relief Dielectric Gratings: Enhanced Transmittance Matrix Approach," Journal of the Optical Society of America A 12(5): 1077-1086.

U.S. Appl. No. 11/394,592, filed Mar. 30, 2006 for Lally et al.

U.S. Appl. No. 11/395,636, filed Mar. 30, 2006 for Lally et al.

U.S. Appl. No. 11/396,214, filed Mar. 30, 2006 for Lally et al.

Wolf, S. (2004). "Introduction to Dual-Damascene Interconnect Processes," Ch. 15.3 *In Silicon Procession for the VLSI ERA*. Lattice Press: Sunset Beach, CA, vol. 4, pp. 674-679, excerpt located online at <http://latticepress.com/damascene.html> (3 pages).

* cited by examiner

MEASURING A DAMAGED STRUCTURE FORMED ON A WAFER USING OPTICAL METROLOGY

BACKGROUND

1. Field

The present application generally relates to optical metrology, and, more particularly, to measuring a damaged structure formed on a wafer using optical metrology.

2. Description of the Related Art

Optical metrology involves directing an incident beam at a structure, measuring the resulting diffracted beam, and analyzing the diffracted beam to determine various characteristics, such as the profile of the structure. In semiconductor manufacturing, optical metrology is typically used for quality assurance. For example, after fabricating a periodic grating in proximity to a semiconductor chip on a semiconductor wafer, an optical metrology system is used to determine the profile of the periodic grating. By determining the profile of the periodic grating, the quality of the fabrication process utilized to form the periodic grating, and by extension the semiconductor chip proximate the periodic grating, can be evaluated.

Conventional optical metrology is used to determine the deterministic profile of a structure formed on a semiconductor wafer. For example, conventional optical metrology is used to determine the critical dimension of a structure. However, the structure may be formed with various stochastic effects, such as damaged materials.

SUMMARY

In one exemplary embodiment, a method of measuring a damaged structure formed on a semiconductor wafer using optical metrology includes directing an incident beam on the damaged structure. A diffracted beam is received from the damaged structure. The received diffracted beam is processed to determine a profile of an undamaged portion of the damaged structure and to measure an amount of dielectric damage of the damaged structure.

BRIEF DESCRIPTION OF THE DRAWINGS

Exemplary embodiments will now be described, by way of example only, with reference to the accompanying schematic drawings in which corresponding reference symbols indicate corresponding parts, and in which.

DETAILED DESCRIPTION

This application is related to co-pending application Ser. No. 11/394,592, entitled DAMAGE ASSESSMENT OF A WAFER USING OPTICAL METROLOGY, filed Mar. 30, 2006; application Ser. No. 11/396,214, entitled MEASURING A DAMAGED STRUCTURE FORMED ON A WAFER USING OPTICAL METROLOGY, filed Mar. 30, 2006, issued Jan. 29, 2008, as U.S. Pat. No. 7,324,193; and co-pending application Ser. No. 11/395,636, entitled CREATING A LIBRARY FOR MEASURING A DAMAGED STRUCTURE FORMED ON A WAFER USING OPTICAL METROLOGY, filed Mar. 30, 2006. The contents of each of these applications are herein incorporated by reference in their entireties.

In material processing methodologies, pattern etching comprises the application of a thin layer of light-sensitive material, such as photoresist, to an upper surface of a wafer that is subsequently patterned in order to provide a mask for transferring this pattern to the underlying thin film during etching. The patterning of the light-sensitive material generally involves exposure by a radiation source through a reticule (and associated optics) of the light-sensitive material using, for example, a micro-lithography system, followed by the removal of the irradiated regions of the light-sensitive material (as in the case of positive photoresist), or non-irradiated regions (as in the case of negative resist) using a developing solvent.

Additionally, single and/or multi-layer masks can be implemented for etching features in a thin film. Soft mask and/or hard mask layers can be used. For example, when etching features in a thin film using a soft mask top layer, the mask pattern in the soft mask layer is transferred to the hard mask layer using a separate etch step (hard mask open) preceding the other etch steps for the thin film. The soft mask can, for example, be selected from several materials for silicon processing including, but not limited to ArF resist materials or photoresist materials compatible with smaller feature sizes, The hard mask can, for example, be selected from several materials for silicon processing including, but not limited to, silicon dioxide ($SiO_2$), silicon nitride ($Si_3N_4$), and carbon.

Figure 1:
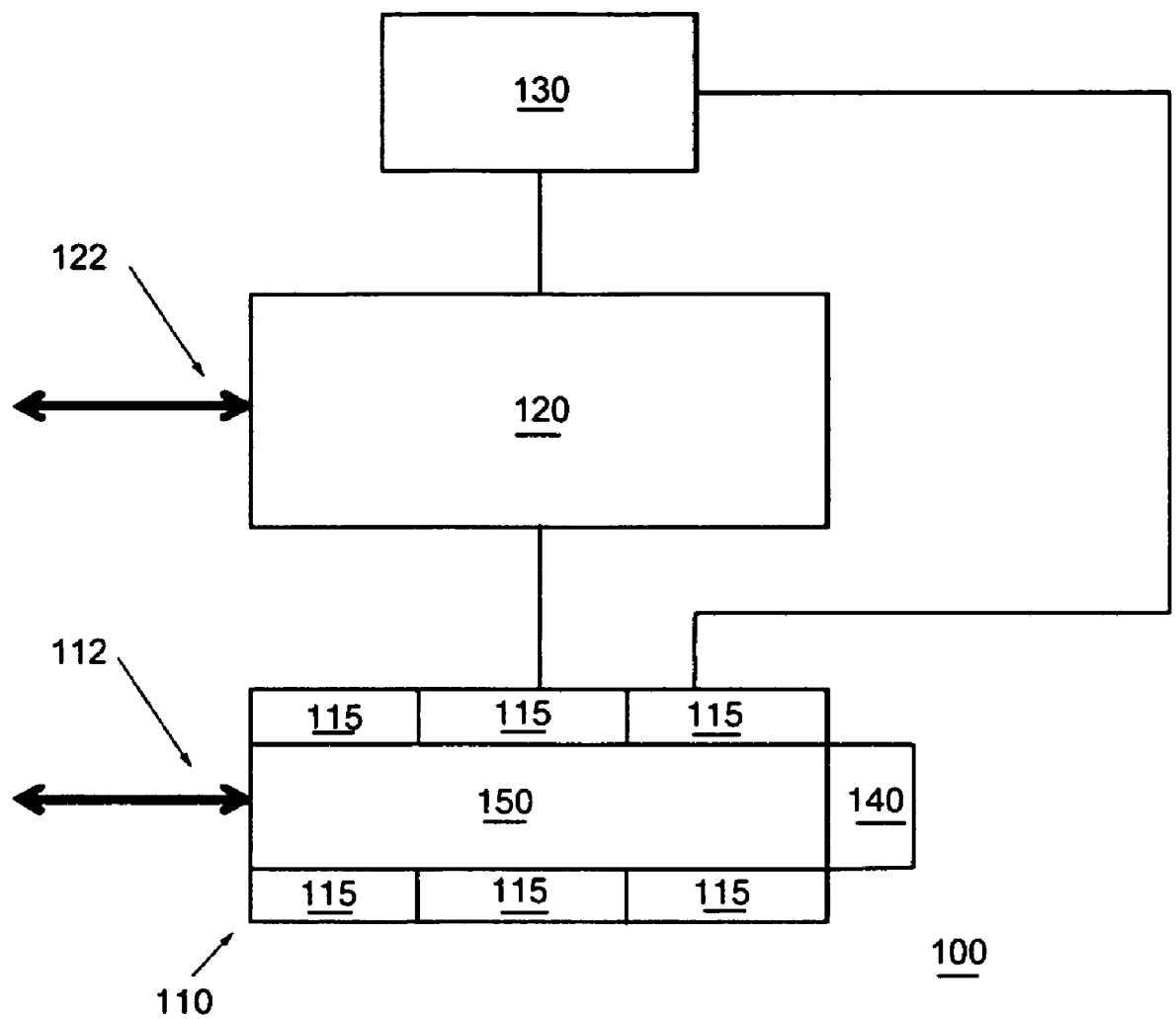
FIG. 1 shows an exemplary block diagram of a processing system in accordance with an embodiment of the present invention.

FIG. 1 shows an exemplary block diagram of a processing system in accordance with an embodiment of the present invention. In the illustrated embodiment, processing system 100 comprises a processing tool 110, a controller 120 coupled to the processing tool 110, and a manufacturing equipment system (MES) 130 coupled to the processing tool 110 and the controller 120. The processing tool 110 can include a number of processing modules 115 that can be coupled to a transfer system 150.

In addition, an integrated metrology module (IMM) 140 can be coupled to the processing tool 110. For example, the IMM 140 can be coupled to the transfer system 150. Alternatively, the IMM 140 may be coupled to the processing tool 110 in a different manner. At least one of the processing tool 110, the controller 120, the MES 130, and the IMM 140 can comprise a control component, a GUI component, and/or a database component (not shown). In alternate embodiments, one or more of these components may not be required.

Some setup and/or configuration information can be obtained by the processing tool 110 and/or the controller 120 from the factory system 130. Factory level business rules can be used to establish a control hierarchy. Business rules can be used to specify the action taken for normal processing and the actions taken on error conditions. For example, the processing tool 110 and/or the controller 120 can operate independently, or can be controlled to some degree by the factory system 130. In addition, factory level business rules can be used to determine when a process is paused and/or stopped, and what is done when a process is paused and/or stopped. In addition, factory level business rules can be used to determine when to change a process and how to change the process.

Business rules can be defined at a control strategy level, a control plan level or a control model level. Business rules can be assigned to execute whenever a particular context is encountered. When a matching context is encountered at a higher level as well as a lower level, the business rules associated with the higher level can be executed. GUI screens can be used for defining and maintaining the business rules. Business rule definition and assignment can be allowed for users with greater than normal security level. The business rules can be maintained in the database. Documentation and help screens can be provided on how to define, assign, and maintain the business rules.

The MES 130 can be configured to monitor some system processes using data reported from the databases associated with the processing tool 110 and/or the controller 120. Factory level business rules can be used to determine which processes are monitored and which data is used. For example, the processing tool 110 and/or the controller 120 can independently collect data, or the data collection process can be controlled to some degree by the factory system 130. In addition, factory level business rules can be used to determine how to manage the data when a process is changed, paused, and/or stopped.

In addition, the MES 130 can provide run-time configuration information to the processing tool 110 and/or the controller 120. Data can be exchanged using GEM SECS communications protocol. For example, APC settings, targets, limits, rules, and algorithms can be downloaded from the factory to the processing tool 110 and/or the controller 120 as an "APC recipe", an "APC system rule", and "APC recipe parameters". Measurement system recipes and settings can be downloaded from the factory to the processing tool 110 and/or the controller 120 as an "IMM recipe", an "IMM system rule", a Profile Application Server (PAS) recipe, and/or "IMM recipe parameters".

In general, rules allow system and/or tool operation to change based on the dynamic state of the processing system 100. Some setup and/or configuration information can be determined by the processing tool 110 and/or the controller 120 when they are initially configured by the processing system 100. In addition, tool level rules can be used to establish a control hierarchy at the tool level. For example, the processing tool 110 and/or the IMM 140 can operate independently, or the IMM 140 can be controlled to some degree by the processing tool 110. In addition, tool level rules can be used to determine when a process is paused and/or stopped, and what is done when a process is paused and/or stopped. In addition, tool rules can be used to determine when to change a process, how to change the process, and how to manage the data.

In FIG. 1, one processing tool 110, and one controller 120 are shown, but this is not required for the invention. The semiconductor processing system can comprise any number of processing tools having any number of controllers associated with them in addition to independent process tools and modules.

The processing tool 110 and/or the controller 120 can be used to configure any number of processing tools having any number of processing tools associated with them in addition to any number of independent process tools and modules. Among other functions, the processing tool 110 and/or the controller 120 can collect, provide, process, store, and display data from processes involving processing tools, processing subsystems, process modules, and sensors.

The processing tool 110 and/or the controller 120 can comprise a number of applications including at least one tool-related application, at least one module-related application, at least one sensor-related application, at least one interface-related application, at least one database-related application, at least one GUI-related application, and at least one configuration application, among others.

The system 100 can comprise an APC system that can interface with processing tools from Tokyo Electron Limited (TEL), such as a Unity Tool, a Telius Tool and/or a Trias Tool and their associated processing subsystems and process modules. In addition, the system 100 can comprise one or more run-to-run (R2R) controllers. For example, the processing system 100 can include a TELIUS™ from Tokyo Electron Limited, and one or more controllers such as a group level controller (i.e. an INGENIO™ GL controller from Tokyo Electron Limited), a tool level controller (i.e. an INGENIO™ controller from Tokyo Electron Limited), and a measurement analysis controller (i.e. a Profiler™ Application Server (PAS) from Timbre Technologies, Inc a TEL company). In addition, the IMM 140 can be an iODP system from Timbre Technologies, Inc. Timbre Technologies, Inc is a California corporation and a wholly owned subsidiary of TEL.

Alternatively, the controller 120 can support other process tools and other process modules.

A GUI component (not shown) can provide easy to use interfaces that enable users to: view tool status and process module status; create and edit x-y charts of summary and raw (trace) parametric data for selected wafers; view tool alarm logs; configure data collection plans that specify conditions for writing data to the database or to output files; input files to statistical process control (SPC) charting, modeling and spreadsheet programs; examine wafer processing information for specific wafers, and review data that is currently being saved to the database; create and edit SPC charts of process parameters, and set SPC alarms which generate e-mail warnings; run multivariate PCA and/or PLS models; and view diagnostics screens in order to troubleshoot and report problems with the TL controller 120. As should be apparent to those skilled in the art, the GUI component need not provide interfaces for all functions. Instead the GUI may provide interfaces for any subset of these functions or others not listed here.

Controller 120 can include a memory (not shown) that can include one or more databases. Data from the tool can be stored as files in a database. In addition, IM data and host metrology data can be stored in the database. The amount of data depends on the data collection plans that are configured, as well as the frequency with which processes are performed and processing tools are run. The data obtained from the processing tools, the processing chambers, the sensors, and the operating system can be stored in the database.

In an alternate embodiment, the system 100 can comprise a client workstation (not shown). The system 100 can support a plurality of client workstations. A client workstation can allow a user to perform configuration procedures; to view status including tool, controller, process, and factory status; to view current and historical data; to perform modeling and charting functions; and to input data to the controller. For example, a user may be provided with administrative rights that allow him to control one or more processes performed by a system component.

Processing tool 110 and the controller 120 can be coupled to MES 130 and can be part of a Fault Detection and Classification (FDC) System. The processing tool 110 and/or the controller 120 can exchange information with a factory system. In addition, the MES 130 can send command and/or override information to the processing tool 110 and/or the controller 120. For example, the MES 130 can feed-forward to the processing tool 110 and/or the controller 120 downloadable recipes for any number of process modules, tools, and measuring devices, with variable parameters for each recipe. Variable parameters can include final CD targets, limits, offsets, and variables in the tool level system that needs to be adjustable by lot. In addition, metrology data can be feed-forwarded to controller 120 from a factory system or a lithography tool, such as a Lithius tool from Tokyo Electron Limited.

Furthermore, the MES 130 can be used to provide measurement data, such as CD SEM information, to the controller 120. Alternately, the CD SEM information can be provided manually. Adjustment factors are used to adjust for any offset between the IM and CD SEM measurements. The measurement and/or historical data can include wafer identification information and a timestamp, such as a date, for proper insertion in to the database.

A single processing tool 110 is also shown in FIG. 1, but this is not required for the invention. Alternately, additional processing tools can be used. In one embodiment, a processing tool 110 can comprise one or more processing modules. Processing tool 110 can comprise at least one of an etch module, a deposition module, a measurement module, a polishing module, a coating module, a developing module, and a thermal treatment module.

Processing tool 110 can comprise link 112 for coupling to at least one other processing tool and/or controller. For example, other processing tools and/or controllers can be associated with a process that has been performed before this process, and/or other controllers can be associated with a process that is performed after this process. Link 112 can be used to feed forward and/or feed back information. For example, feed forward information can comprise data associated with an in-coming wafer. This data can include lot data, batch data, run data, composition data, and wafer history data.

The IMM 140 can include an Optical Digital Profiling (ODP) system. The processing tool 110 can also include module related measurement devices, tool-related measurement devices, and external measurement devices. For example, data can be obtained from sensors coupled to one or more process modules and sensors coupled to the processing tool. Sensors can include an Optical Emission Spectroscopy (OES) sensor and optical end point detection sensor. For example, the wavelength ranges for these sensors can range from 200 nm to 900 nm. In addition, data can be obtained from an external device such as a Scanning Electron Microscopy (SEM) tool, a Transmission Electron Microscopy (TEM) tool, and an Optical Digital Profiling (ODP) tool.

An ODP tool is available from Timbre Technologies Inc. (a TEL company) that provides a technique for measuring the profile of a structure in a semiconductor device. For example, ODP techniques can be used to obtain critical dimension (CD) information, structure profile information, or via profile information.

Controller 120 is coupled to processing tool 110 and MES 130, and information such as pre-processing data and post-processing data can be exchanged between them. For example, when an internal error event is generated by the tool, the controller 120 can send a message, containing information about the event, to the MES 130. This can allow the factory system and/or factory personnel to make the necessary changes to minimize the number of wafers at risk after a major change occurs such as those that occur during corrective or preventative maintenance.

A single controller 120 is also shown in FIG. 1, but this is not required for the invention. Alternatively, additional controllers can be used. For example, the controller 120 can comprise at least one of a run-to-run (R2R) controller, a feed-forward (FF) controller, a process model controller, a feedback (FB) controller, and a process controller (all not shown in FIG. 1).

Controller 120 can comprise link 122 for coupling to at least one other controller. For example, other controllers can be associated with a process that has been performed before this process, and/or other controllers can be associated with a process that is performed after this process. Link 122 can be used to feed forward and/or feedback information.

In one case, the controller 120 knows the input state and a model equation for the desired state for the wafer, and the controller determines a set of recipes that can be performed on the wafer to change the wafer from the input state to a processed state. In another case, the controller 120 determines the input state and desired state for the wafer, and the controller 120 determines a set of recipes that can be performed on the wafer to change the wafer from the input state to the desired state. For example, the set of recipes can describe a multi-step process involving a set of process modules.

One time constant for the controller 120 can be based on the time between measurements. When measured data is available after a lot is completed, the controller's time constant can be based on the time between lots. When measured data is available after a wafer is completed, the controller's time constant can be based on the time between wafers. When measurement data is provided real-time during processing, the controller's time constant can be based on processing steps, within a wafer. When measured data is available while a wafer is being processed or after a wafer is completed or after the lot is completed, the controller 120 can have multiple time constants that can be based on the time between process steps, between wafers, and/or between lots.

One or more controllers 120 can be operating at any point in time. For example, one controller can be in an operating mode while a second controller can be in a monitoring mode. In addition, another controller can be operating in a simulation mode. A controller can comprise a single loop or multiple loops, and the loops can have different time constants. For example, loops can be dependent on wafer timing, lot timing, batch timing, chamber timing, tool timing, and/or factory timing.

The controller 120 can compute a predicted state for the wafer based on the input state, the process characteristics, and a process model. For example, a trim rate model can be used along with a processing time to compute a predicted trim amount. Alternately, an etch rate model can be used along with a processing time to compute an etch depth, and a deposition rate model can be used along with a processing time to compute a deposition thickness. In addition, models can include SPC charts, PLS models, PCA models, FDC models, and Multivariate Analysis (MVA) models.

The controller 120 can receive and utilize externally provided data for process parameter limits in a process module. For example, the controller GUI component provides a means for the manual input of the process parameter limits. In addition, a factory level controller can provide limits for process parameters for each process module.

The controller 120 can receive and execute models created by commercially available modeling software. For example, the controller can receive and execute models that were created by external applications and sent to the controller.

In one embodiment, controller 120 can be used to run FDC applications and can send and/or receive information concerning an alarm/fault condition. For example, the controller can send and receive FDC information to and from a factory level controller or a tool level controller. In addition, FDC information can be sent via the e-Diagnostics network, e-mail, or pager after the identification of an error condition. In an alternate embodiment, FDC applications can be run on different controllers.

The controller 120 can take various actions in response to an alarm/fault, depending on the nature of the alarm/fault. The actions taken on the alarm/fault can be based on the business rules established for the context specified by the system recipe, process recipe, module type, module identification number, load port number, cassette number, lot number, control job ID, process job ID, slot number and/or the type of metrology data. In one embodiment, the controller determines the actions to take. Alternately, the controller may be instructed to take some specific actions by the FDC system.

The controller 120 can comprise a database component for archiving input and output data. For example, the controller can archive, among other things, received inputs, sent outputs, and actions taken by the controller in a searchable database. In addition, the controller 120 can comprise hardware and/or software for data backup and restoration. In addition, the searchable database can include model information, configuration information, and historical information and the controller 120 can use the database component to backup and restore model information and model configuration information both historical and current. Furthermore, the searchable database can include damage-assessment information, such as wafer data and/or process data, configuration information, and historical information and the controller can use the database component to backup and restore the damage-assessment information and wafer information both historical and current.

The controller 120 can comprise a web-based user interface. For example, the controller 120 can comprise a web enabled GUI component for viewing the data in the database. The controller can comprise a security component that can provide for multiple levels of access depending on the permissions granted by a security administrator. The controller 120 also can comprise a set of default models that are provided at installation time and have the ability to reset to default conditions.

The controller has the capability of managing multiple process models that are executed at the same time and are subject to different sets of process recipe constraints. The controller can run in three different modes: simulation mode, test mode, and standard mode. A controller can operate in simulation mode in parallel with the actual process mode. In addition, FDC applications can be run in real-time and produce real-time damage-assessment results. Furthermore, FDC applications can be run in a simulation mode and produce predicted damage-assessment results.

When the processing system includes a host system and one or more semiconductor processing systems, the host system can operate as the master system and can control and/or monitor a major portion of the processing operations. The host system can create a process sequence, and can send the process sequence to the processing system. In one embodiment, the process sequence can comprise a sequence of measurement module visits and processing module visits. A process job (PJ) can be created for each measurement module visit and each processing module visit.

In addition, virtual measurements and/or damage-assessments can be made when a processing system controller executes in a simulation mode. The results from simulation mode executions can be stored and used to predict damage-assessment and/or potential fault conditions.

A single processing tool 110 is also shown in FIG. 1, but an arrangement including only one processing tool 110 is not required for the invention. Alternately, additional processing tools can be used. In one embodiment, the processing tool 110 can comprise means for performing a trimming procedure as described. Alternatively, the processing tool 110 may comprise at least one of an etch module, a deposition module, a polishing module, a coating module, a developing module, an ashing module, an oxidation module, and a thermal treatment module, among others.

Figure 2:
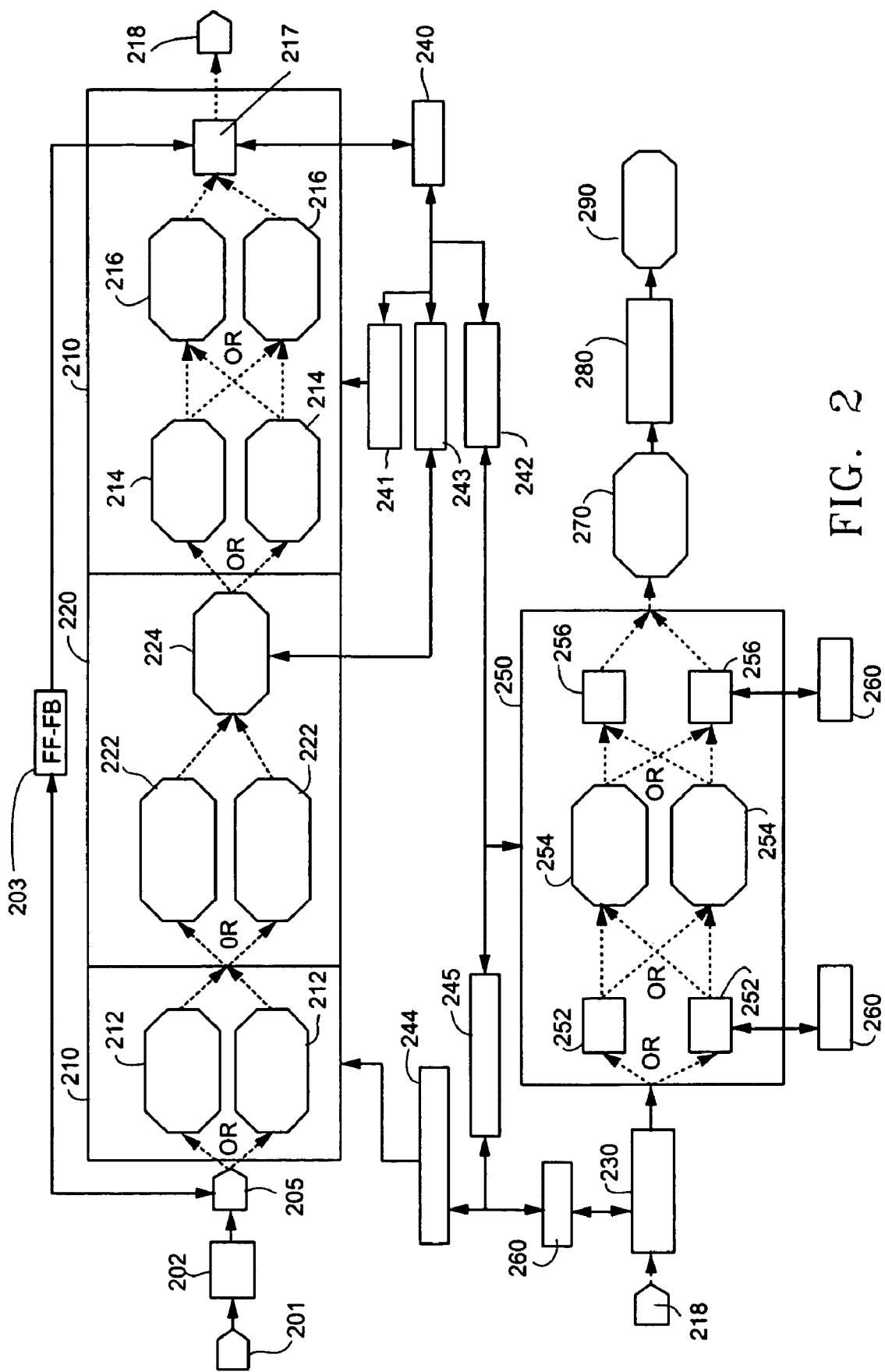
FIG. 2 illustrates a simplified schematic view of a wafer-processing diagram in accordance with embodiments of the invention.

FIG. 2 illustrates a simplified schematic view of a wafer-processing diagram in accordance with embodiments of the invention. In the illustrated embodiment, an input element 201 is shown that can be a FOUP containing a number of wafers. A wafer state element 202 is shown, and wafer state information can be fed forward and used during wafer processing to a measurement element 218. A control element 205 is shown coupled to two processing elements 212 in a lithography element 210, and coupled to another control element 203 that can be used to manage feed forward and feed back data. For example, the lithography element can be a Lithius System from Tokyo Electron Limited, and the processing elements 212 may be coating units.

A scanner element 220 can be coupled to lithography element 210. The scanner element may include two alignment elements 222 coupled to an exposure unit 224.

In addition, the lithography element 210 can also include two baking units 214 that can be coupled to two developing units 216. The developing units 216 can be coupled to a metrology module 217, when the lithography system includes a metrology unit 217. The metrology unit 217 can be coupled to a controller 240 and can exchange information with the controller 240. In addition, the metrology unit 217 can be coupled to a control element 203 and can exchange information with the control element 203. The controller can use metrology data from the metrology unit 218 during one or more wafer processing procedures, such as Dual Damascene procedures. In the illustrated embodiment, a number of decision ("OR") elements are shown to indicate different paths a wafer may take during processing. Alternatively, a different number of processing elements may be used. The controller 240 can feed back data 241 to the lithography unit 210, can exchange data 243 with the scanner unit 220, and/or exchange data 242 with an etch system 250.

In FIG. 2, the lithography system 210 is shown coupled 218 to etching system 250. The etching system 250 can include a second wafer state element 230, and some of the wafer state information can be provided to a controller 260 that can exchange information 245 with the etching system 250, and/or exchange information 244 with the lithography system 210. This wafer state information may include additional measurement data. For example, during wafer processing some wafers may be sent to an external metrology unit, which may be an external optical metrology tool, or a CD SEM tool.

The second wafer state element 230 can be coupled to the etch system 250. The etch system 250 can include a number of pre-processing metrology elements 252, a number of etch processing elements 254, and a number of post-processing metrology elements 256. The metrology elements 252 and 256 can be coupled to a controller 260 and exchange information with the controller 260. The controller 260 can use metrology data from the metrology elements 252 and 256 during one or more Dual Damascene procedures. In the illustrated embodiment, a number of decision ("OR") elements are shown to indicate different paths a wafer may take during processing. Alternatively, a different number of metrology elements and/or processing elements may be used. The controller 260 can feed back data 241 to the lithography unit 210, can feedback data 243 to the scanner unit 220, and/or feed forward data 242 to an etch system 250.

The etch system 250 can be coupled to a cleaning system 270. The cleaning system 270 can include wet and/or dry processes. The cleaning system 270 can be coupled to a measurement element 280. The measurement element can include an ODP system, a CD SEM system, a TEM system, and/or a FIB system (all not shown).

A repeat element 290 is also shown to illustrate that a wafer processing procedure may be performed a number of times when a number of wafers require processing. In addition, a different set of steps may be used. When processing systems and measurement systems are coupled and controlled as shown in FIG. 2, the wafer throughput time can be minimized, and the number of metrology modules/processes can be reduced.

The processing system 100 can be used to process wafers having isolated and nested damascene features and control strategies can be used to define the process sequence. During an isolated/nested measurement sequence, the processing tool selects one IM recipe to use, and separate IMM recipes can be used for isolated and nested structures. Each wafer can be measured separately for each pitch and structure.

For example, a wafer can be loaded into an integrated metrology (IM) module; an IM recipe can be loaded into the IM module; and a Profiler Application Server (PAS) recipe can be loaded into the IM controller. Next, the wafer can be measured and an ODP recipe can be loaded into the IM controller. The library can then be searched using the measured spectrum, and one or more isolated structures can be identified. When isolated structures are being measured and/or being examined for damage, IM, PAS, ODP, and damage-assessment recipes for isolated structures can be used.

Subsequently, another IM recipe can be loaded into an integrated metrology (IM) module, and another PAS recipe can be loaded into the IM controller. The wafer can be measured or previous measurement data can be used, and another ODP recipe can be loaded into the IM controller. Next, the library can be searched using the measured spectrum, and one or more nested structures can be identified. When Nested structures are being measured and/or being examined for damage, IM, PAS, ODP, and damage-assessment recipes for nested structures can be used. The measurement sequence can be performed for one or more different locations on a wafer, and the wafer can be unloaded.

In one embodiment, a measurement grating/structure having a first pitch is provided that is consistent with the isolated structures/features for a particular product and technology and another measurement grating/structure having a second pitch is provided that is consistent with the nested structures/features for this product and technology. For example, a 612 nm grating can be used for isolated structures and a 245 nm grating can be used for nested structures. In alternate embodiments, additional measurement gratings may be provided and different pitches may be provided.

As would be appreciated by those skilled in the art, the illustrated components of the processing system 100 are intended merely to be exemplary of the system of the present invention. As would be appreciated by those skilled in the art, and as will be made apparent from the discussion that follows, the permutations of combinations of components for the present invention is significant. Each such variation, while not discussed herein, is intended to fall within the scope of the present invention.

The processing system 100 can provide IMM wafer sampling and the wafer slot selection can be determined using a (PJ Create) function. The R2R control configuration can include, among other variables, feed forward control plan variables, feedback control plan variables, metrology calibration parameters, control limits, and SEMI Standard variable parameters. Metrology data reports can include wafer, site, structure, and composition data, among others, and the tool can report actual settings for the wafer.

The IMM 140 can use polarizing reflectometry, spectroscopic ellipsometry, reflectometry, or other optical instruments to measure true device profiles, accurate critical dimensions (CD), and multiple layer film thickness of a wafer. The process is executed in-line, which eliminates the need to break the wafer for performing the analyses. ODP can be used with the existing thin film metrology tools for inline profile and CD measurement, and can be integrated with TEL processing tools to provide real-time process monitoring and control. An ODP Profiler can be used both as a high precision metrology tool to provide actual profile, CD, and film thickness results, and a yield enhancement tool to detect in-line process excursion or process faults.

An ODP™ solution has three key components: ODP™ Profiler™ Library comprises an application specific database of optical spectra and its corresponding semiconductor profiles, CDs, and film thicknesses. Profiler™ Application Server (PAS) comprises a computer server that connects with optical hardware and computer network. It handles the data communication, ODP library operation, measurement process, results generation, results analysis, and results output. The ODP™ Profiler™ Software includes the software installed on PAS to manage measurement recipe, ODP™ Profiler™ library, ODP™ Profiler™ data, ODP™ Profiler™ results search/match, ODP™ Profiler™ results calculation/analysis, data communication, and PAS interface to various metrology tools and computer network.

An exemplary optical metrology system is described in co-pending U.S. patent application Ser. No. 09/727,530, entitled SYSTEM AND METHOD FOR REAL-TIME LIBRARY GENERATION OF GRATING PROFILES, by Jakatdar, et al., filed on Nov. 28, 2000, and is incorporated in its entirety herein by reference.

ODP techniques can be used to measure the presence and/or thickness of coatings and/or residues within features of a patterned wafer. These techniques are taught in co-pending U.S. patent application Ser. No. 10/357,705, entitled MODEL OPTIMIZATION FOR STRUCTURES WITH ADDITIONAL MATERIALS, by Niu, et al., filed on Feb. 3, 2003, and ODP techniques covering the measurement of additional materials are taught in U.S. Pat. No. 6,608,690, entitled OPTICAL PROFILOMETRY OF ADDITIONAL-MATERIAL DEVIATIONS IN A PERIODIC GRATING, filed on Dec. 4, 2001, and in U.S. Pat. No. 6,839,145, entitled OPTICAL PROFILOMETRY OF ADDITIONAL-MATERIAL DEVIATIONS IN A PERIODIC GRATING, filed on May 5, 2003, and all are incorporated by reference herein.

ODP techniques for creating a metrology model are taught in co-pending U.S. patent application Ser. No. 10/206,491, entitled MODEL AND PARAMETER SELECTION IN OPTICAL METROLOGY, by Voung, et al., filed on Jul. 25, 2002 and ODP techniques covering integrated metrology applications are taught in U.S. Pat. No. 6,785,638, entitled METHOD AND SYSTEM OF DYNAMIC LEARNING THROUGH A REGRESSION-BASED LIBRARY GENERATION PROCESS, filed on Aug. 6, 2001, and both are incorporated by reference herein.

A control system, such as the INGENIO™ system from Tokyo Electron Limited, can comprise management applications, such as a recipe management application. For example, the recipe management application can be used to view and/or control a recipe stored in the Ingenio system database that is synchronized with equipment via a network environment from the INGENIO™ system. An INGENIO™ client can be placed separately at a distance from the factory, and can provide comprehensive management functions to multiple equipment units.

Recipes can be organized in a tree structure that can comprise recipe sets, classes, and recipes that can be displayed as objects. Recipes can include process recipe data, system recipe data, and IMM recipe data. Data can be stored and organized using a recipe set. The IMM recipes that are on the processing tool 110 can be used to determine wafer sampling and a relationship between slots and IM recipes. IM recipes can exist on IMM 140, can be selected in Telius IMM recipes, can contain pattern recognition information, can be used to identify the chips to sample on each wafer, and can be used to determine which PAS recipe to use. PAS recipes can be used to determine which ODP library to use, and to define the measurement metrics to report, such as top CD, bottom CD, side wall angle (SWA), layer thicknesses, trench width, and goodness of fit (GOF).

A control system, such as the INGENIO™ system, can include APC applications that can operate as control strategies, and a control strategy can be associated with a control plan that can include an etching tool recipe. Wafer level context matching at runtime allows for custom configuration by wafer (slot, waferID, lotID, etc.). A control strategy can include one or more control plans, and a process module and/or measurement module that is being controlled has at least one control plan defined for a visit to the process module and/or measurement module. Control plans can contain damage-assessments, models, control limits, targets, and can include static recipes, formula models, and feedback plans.

In the control system, feed forward and/or feedback control can be implemented by configuring Control Strategies, Control Plans, and Control Models. A Control Strategy can be written for each system process where feed forward and/or feedback control is implemented. When a strategy is protected, all of its child objects (plans and models) cannot be edited. When a system recipe executes, one or more of the Control Plans within the Control Strategy can be executed. Each control plan can be used to modify the recipe based on feed-forward and/or feedback information.

A control strategy can be used to establish a processing recipe and processing tool; to determine control plans; to assess wafer damage, to establish an action in response to a failure; to establish context; to establish a control type (standard, simulated or test); to establish a control action (enabled/disabled); and to establish a control state (protected/unprotected).

Control strategies can comprise standard control strategies and simulation control strategies. The standard control strategies can be configured to control the process tool 110. A simulation control strategy can be associated with simulation control plan(s). Based on the model selected, the control plan will tune the recipe variables. The recipe variables can be logged by the controller but not sent to process tool. Multiple simulation control strategies can be executed simultaneously, but only one standard type of control plan will be executed for a given wafer.

Furthermore, a control strategy can include other fields that may be manipulated. For example, the LotID(s) field can be used to enter/edit the lot identifiers; the CJID(s) field can be used to enter/edit the control job identifiers. The PJID(s) field can be used to enter/edit the process job identifiers. The Cassette ID(s) field can be used to enter/edit the cassette identifiers. The Carrier ID(s) field can be used to enter/edit the carrier identifiers. The Slot(s) field can be used to enter/edit the slot numbers. The Wafer Type(s) field can be used to enter/edit the wafer types. The Scribed Wafer ID(s) field can be used to enter/edit the scribed wafer identifiers. The Wafer ID(s) field can be used to enter/edit the wafer identifiers. The Wafer ID(s) field can be used to enter/edit the wafer identifiers. The Start Time earlier than field can be used to enter/edit the start time. In addition, the Start Time later than field can be used to enter/edit the end time.

Control plans can cover multiple process steps within a module, and can be controlled by the factory. Parameter ranges can be defined for each process and/or measurement module, and variable parameter "Limit Ranges" are provided for each control parameter.

The control system can include APC applications that can be used to analyze the collected data, and establish error conditions. An analysis application can be executed when a context is matched. During the execution of an analysis application, one or more analysis plans can be executed. For example, univariate SPC models/plans may be executed, and may trigger SPC alarms; PCA and/or PLS models/plans may be executed, and may trigger SPC alarms; multivariate SPC models/plans may be executed, and may trigger SPC alarms; and other file output plans may be executed, and may trigger software alarms.

A plan can create an error when a data failure occurs, an execution problem occurs, or a control problem occurs. When an error occurs, the plan can generate an alarm message; the parent strategy status can be changed to a failed status; the plan status can be changed to a failed status; and one or more messages can be sent to the alarm log and the FDC system. When a feed forward plan or a feedback plan fails, one or more of the plans in the parent strategy may be terminated, and their status can be changed to a failed status. In one case, when a bad incoming wafer is detected, a control plan can detect and/or identify this as a faulty incoming wafer. In addition, when a feedback plan is enabled, the feedback plan can skip a wafer that has been identified to be defective and/or faulty by another plan. A data collection plan can reject the data at all the measurement sites for this wafer or reject the data because a damage-assessment procedure fails to meet allowable damage limits.

In one embodiment, feedback plan failure may not terminate the strategy or other plans, and a damage-assessment procedure failure may also not terminate the strategy or other plans. Successful plans, strategies, and/or damage-assessment procedures do not create any error/alarm messages.

Processing system 100 can include an FDC system that includes applications for managing error/alarm/fault conditions. When an error, alarm, and/or fault condition is detected, an FDC application in the FDC system can send a message to one or more processing modules and/or tools. For example, a message can be sent to pause the current process or to stop the current process when a damage-assessment limit is reached or exceeded. In one case, a tool pause/stop can be done by changing the value of the maintenance counter.

Pre-specified failure actions for strategy and/or plan errors can be stored in a database, and can be retrieved from the database when an error occurs. Failure actions can include use the nominal process recipe for this wafer and module; use a null process recipe for this wafer and module; pause the process module and wait for intervention; pause the whole tool and wait for intervention. For example, a processing tool may take action only when the wafer with the error reaches the target process module where the R2R failure occurred, and the processing tool may be able to continue processing other lots, recipes, or wafers in other modules. A null recipe can be a control recipe that is used by a processing tool and/or processing system to allow a wafer to pass through and/or remain in a processing chamber without processing. For example, a null recipe can be used when a processing tool is paused or when a wafer does not require processing.

The FDC system can detect faults, predict tool performance, predict preventative maintenance schedules, decrease maintenance downtime, and extend the service life of consumable parts in the processing tool. The FDC system collects data from the tool and additional sensors, calculates summary parameters, performs MVAs, and compares the results with normal operation using SPC. For example, the SPC component can perform a series of Western Electric run-rule evaluations, and generates an SPC alarm if a run-rule is violated.

The operations of the APC system and the FDC system can be configured by the customer and can be based on the context of the wafers being processed. Context information includes recipe, lot, slot, control job, and process job. The user interfaces for APC system and the FDC system are web-enabled, and provide a near real time tool status and a real time alarm status display.

The controller 120 can use equation-based techniques, formula-based techniques, and table-based techniques in different processing regimes. When the controller 120 uses these techniques, the feed-forward and/or feedback control variables can be configurable.

The controller 120 can operate as a single input single output (SISO) device, as a single input multiple output (SIMO) device, as a multiple input single output (MISO) device, and/or as a multiple input multiple output (MIMO) device, among other variants. In addition, inputs and outputs can be within one controller 120 and/or between one or more controllers 120. In a multi-process case including multiple modules, damage-assessment information can be fed-forward or fed-back from one controller to another controller.

When a processing tool and/or process module sends data to the database, this data can be accessed by the controller 120. For example, this data can comprise tool trace data, maintenance data, and end point detection (EPD) data. The tool-related data can be used to create and/or update damage-assessment procedures and/or processing procedures, and the updated information can be stored during processing or after the processing of a wafer is completed.

The controller 120 can receive and utilize externally provided data for process parameter limits in a process module. For example, the controller GUI component provides a means for the manual input of the process parameter limits. In addition, a factory level controller can provide limits for process parameters for each process module.

The controller 120 can receive and execute models created by commercially available modeling software. For example, the controller 120 can receive and execute models (PLA, PCA, etc.) that were created by external applications and sent to the controller 120.

Damage-assessment procedures and/or damage-assessment model updates can be performed by running test wafers, varying the process settings and observing the results, then updating the damage-assessment procedures and/or damage-assessment models. For example, an update can take place every N processing hours by measuring the before and after characteristics of a test wafer. By changing the settings over time to check different operating regions one could validate the complete operating space over time, or run several monitor wafers at once with different recipe settings. The update procedure can take place within the controller 120 at the tool or at the factory, allowing the factory control to manage the test wafers and model updates.

The controller 120 can compute an updated recipe and/or updated damage-assessment procedure for the next wafer. In one case, the controller 120 can use the feed-forward information, modeling information, and the feedback information to determine whether or not to change the current recipe before running the current wafer, before running the next wafer, or before running the next lot.

When a metrology data source is being used to provide process result data, a route sequence can be specified which causes a wafer to be routed to the IMM 140 at the correct point in the process. For example, a wafer can be routed to the IMM 140 before entering a processing module 115 and/or after the wafer has been processed in a processing module 115. In addition, an IM recipe can be specified which causes a set of pre-determined measurements to be made and a pre-determined set of output data to be provided. For example, the data can be filtered before the data is averaged and used by the controller 120.

The controller 120 can comprise one or more filters (not shown) to filter the metrology data in order to remove the random noise. A noise filter can be used to remove random noise and stabilize the control loop, an Exponentially Weighed Moving Average (EWMA) or Kalman filter can be applied. In addition, an outlier filter can be used to remove outliers that are statically not valid and should not be considered in the calculation of the mean of a wafer measurement. Furthermore, the control can include the ability to filter sites based on an alarm from the measurement analysis calculations and/or damage-assessment procedures. For example, measurement sites can be filtered based on an alarm from the metrology system, and this may occur when the site measurement calculations have an error, or when a site is outside the library space, or when a site is at the edge of the library space.

The controller 120 can receive and utilize feedback data. For example, the controller 120 can receive damage-assessment information for wafers that has already been processed and adjust the process model based on this data.

The controller 120 can send and receive notification of an error condition. For example, the controller 120 can send and receive notifications to and from a factory level controller, a R2R controller, and/or a tool level controller, among other devices. In addition, a notification can be sent via the e-Diagnostics network, e-mail, or pager after the identification of an error condition.

The controller 120 can calculate and/or run damage-assessment procedures and/or models in a simulated mode. For example, the controller 120 can operate in simulation mode in parallel with the actual process mode. In this case, the simulated actions can be recorded in the historical database, and immediate action is not taken.

The controller 120 can select damage-assessment procedures and/or models based on incoming material context. For example, the controller 120 can select damage-assessment procedures and/or models based on the incoming material state and process recipe. The controller can comprise means to verify that the system 100 can calculate a valid R2R setting.

The controller 120 inputs can include time constants for feed-forward/feed-back loops, a reset event for accumulation, an IMM step, and ODP offset, among others. Instructions can include, inter alia, targets, tolerances, computational commands, data collection plans, algorithms, models, coefficients, and recipes. The Wafer State can include information, for example, from the wafer being processed (site, wafer, lot, batch state), profiles, and characteristics measured physically or electrically. The Module Physical State can include the current or last known recorded state of the module and components that will be used to process the wafer—RF hours, number of wafers, consumable states. The Process State can include the current or last known measured state from sensors of the processing environment, including trace data, and summary statistics. The Controller Parameters can include the last settings for the recipe/controller set points and process targets that created the wafer state, module physical state, and process state.

The controller 120 can comprise at least one computer and software that supports R2R operational software, such as the Ingenio software. In one case, the operational software comprises at least one of: a configuration means, a data management means, a GUI means, a fault management means, and a trouble-shooting means. In addition, configuration GUI screens can be used to configure the interface between the computer and the processing element, to determine the device type for the processing element (i.e., tool, module, sensor, etc.). Data management GUI screens can be used to determine the amount and type of data to collect and to determine how to and where to store the collected data. Furthermore, fault management GUI screens can be used to inform a user about fault conditions.

In general, feed-forward control can include the updating of a process module and/or measurement module recipe using pre-process data measured on the wafer prior to its arrival in the module. In one case, metrology data and process target data are received by the controller 120. These values can be compared, and the result is the desired process result (for example, the desired trim amount). Then, this desired process result can be sent to the controller for model selection and calculation of the appropriate process recipe parameters. This new recipe is sent to the process module and the wafer is processed (trimmed) using the new recipe.

In the system 100, feed-forward control can be implemented, in the controller 120, by configuring Control Strategies, Control Plans, and Control Models. A Control Strategy can be written for each system recipe where feed-forward control is implemented. When this system recipe executes in the processing tool 110, the Control Plans within the Control Strategy can be executed. Each control plan can be used to modify the recipe based on feed-forward information.

A control plan can include input data sources. A different number of input data sources can be used, and each input data source can have a different symbol value. For example, one data source can be an ODP tool, and it can be part of the processing tool, such as a Telius. In addition, another data source can be a SEM, and the Parameter/Value can be actual measured data such as a CD-SEM data.

Using inputs from these data sources, a user can specify a calculation for the target calculation. The result of this calculation is then used to choose which control model to execute. The system starts with the Nominal Recipe (the recipe, as it exists on the tool). Then, the updates from each executed Control Plan are added. Once all the Control Plans are executed (within the matching Control Strategy), the final recipe is sent to the tool.

The controller 120 can operate as a recipe parameter solver that produces recipe parameters according to appropriate process model, process model constraints, process targets, and process parameter constraints. The controller 120 has the capability of managing multiple process models that are executed at the same time and are subject to a single set of process recipe constraints. If control failure occurs, the controller 120 can be configured to use the tool process recipe (nominal recipe), use the null recipe, or to stop Run-to-Run control (according to tool parameter settings). To pause the tool 110, the controller 120 can be configured to pause the process module, or to pause the entire system 100.

Figure 3:
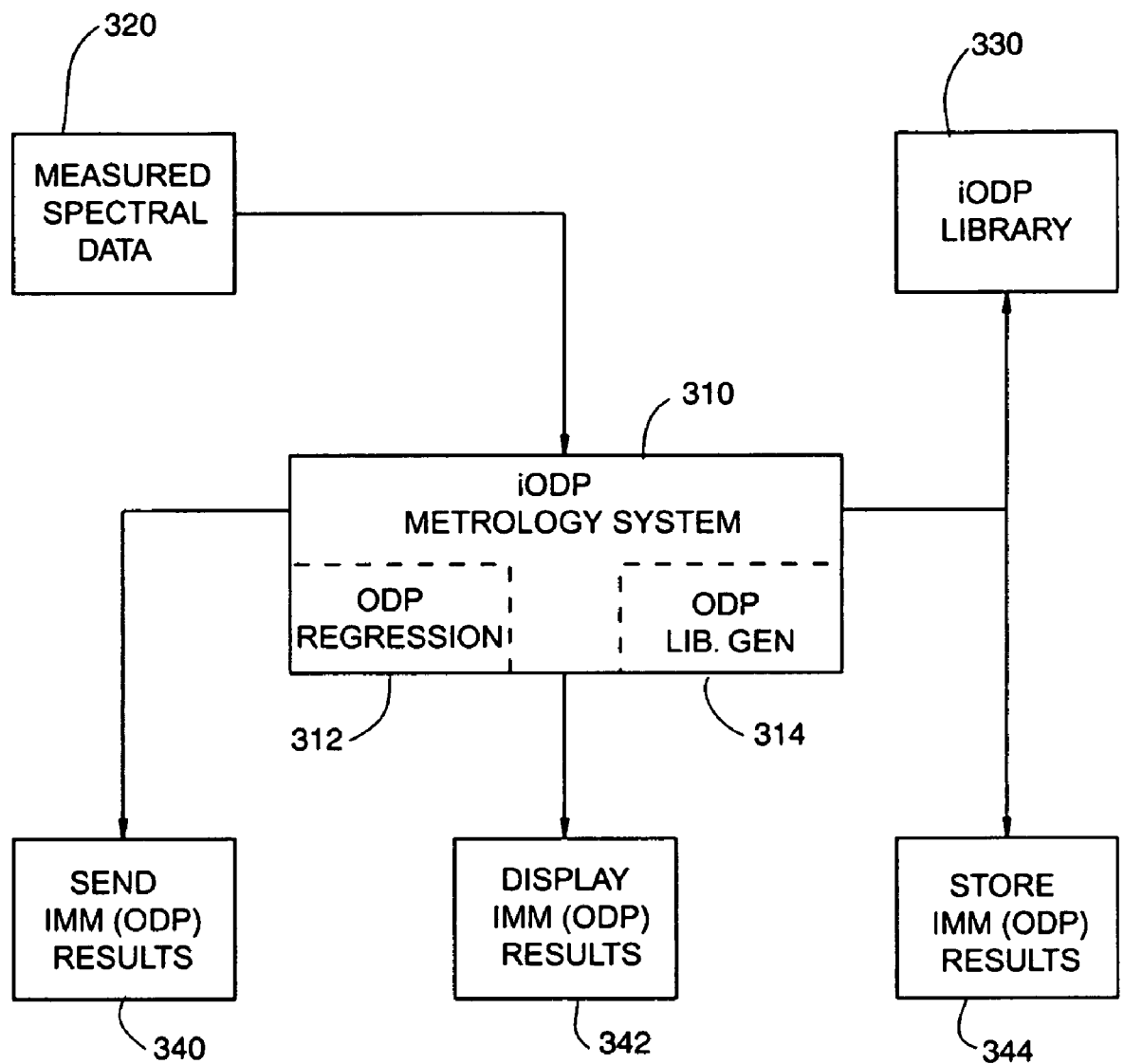
FIG. 3 shows an exemplary view of an optical metrology system in accordance with embodiments of the invention.

FIG. 3 shows an exemplary view of an optical metrology system in accordance with an embodiment of the invention. In the illustrated embodiment, an optical metrology system 300 is shown that can be configured to examine periodic structures, such as gratings and/or patterned arrays, to obtain measured spectral data 320. For example, zero-order cross polarization measurement data may be obtained, and wafer measurement data may be obtained based on the zero-order cross polarization measurement data.

Device features and/or structures can be obtained using a periodic measurement structures formed on a wafer. For example, as the features and/or structures of the devices/circuits are formed on wafer through one or more fabrication processes described herein, the features of periodic measurement structures are also formed on wafer.

In addition, one or more periodic measurement structures can be formed in test areas on wafer that are proximate to or within devices/circuits formed on wafer. For example, periodic measurement structures can be formed adjacent a device/circuit formed on wafer. Alternatively, periodic measurement structures can be formed in an area of the device/circuit that does not interfere with the operation of the device/circuit or along scribe lines on wafer. Thus, the optical measurements obtained for periodic measurement structures can be used to determine whether the devices/circuits adjacent periodic measurement structures have been fabricated according to specifications.

In addition, optical metrology system 300 can include a metrology system 310, such as an iODP system. The metrology system 310 can include a real-time component 312 that can be used to perform pattern analysis using ODP regression techniques, and off-line component 314 that can be used for the generation of iODP libraries 330. For example, regression optimization procedures can be performed on a set of measurements to obtain a set of resultant parameter values that can be associated with a profile of a structure and/or feature. In addition, the metrology system 310 can include an interface component 340 for sending IMM (ODP) results to other system components, a display component 342 for displaying IMM (ODP) results to one or more GUI screens, and a storage component 344 for storing IMM (ODP) results.

Examples of optical metrology devices include spectroscopic ellipsometers, spectroscopic reflectometers, variable angle, single wavelength reflectometers and ellipsometers, and polarization reflectometers and ellipsometers. When optical metrology system 300 includes an ellipsometer, the amplitude ratio tan Ψ and the phase Δ of a diffraction signal can be received and detected. When optical metrology system 300 includes a reflectometer, the relative intensity of a diffraction signal can be received and detected. Additionally, when optical metrology system 300 includes a polarization reflectometer, the phase information of a diffraction signal can be received and detected.

Optical metrology system 300 can receive a measured diffraction signal and analyze the measured diffraction signal, and the periodic measurement structures can be determined using various linear or non-linear profile extraction techniques, such as a library-based process, a regression-based process, and the like. For a more detailed description of a library-based process, see U.S. patent application Ser. No. 09/907,488, entitled GENERATION OF A LIBRARY OF PERIODIC GRATING DIFFRACTION SIGNALS, filed on Jul. 16, 2001, which is incorporated herein by reference in its entirety. For a more detailed description of a regression-based process, see U.S. patent application Ser. No. 09/923,578, entitled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety. For a more detailed description of a machine learning system, see U.S. patent application Ser. No. 10/608,300, entitled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

In addition, optical measurement systems and techniques are taught in U.S. Pat. No. 6,947,141, entitled OVERLAY MEASUREMENTS USING ZERO-ORDER CROSS POLARIZARIZATION MEASUREMENTS, filed on Sep. 8, 2004, U.S. Pat. No. 6,928,395, entitled METHOD AND SYSTEM FOR DYNAMIC LEARNING THROUGH A REGRESSION-BASED LIBRARY GENERATION PROCESS, filed on May 27, 2004, and U.S. Pat. No. 6,839,145, entitled OPTICAL PROFILOMETRY OF ADDITIONAL-MATERIAL DEVIATIONS IN A PERIODIC GRATING, filed on May 5, 2003 and all of which are assigned to Timbre Technologies, Inc a TEL company and all are incorporated by reference herein.

With continuing reference to FIG. 3, an optical metrology system 300 can be used to examine and analyze a damaged and/or un-damaged measurement structure. For example, optical metrology system 300 can be used to determine the profile of a measurement structure, such as a periodic grating and/or array, formed on wafer. The measurement structure can be formed in test areas on wafer, such as adjacent to a device formed on wafer. Alternatively, a measurement structure may be formed in an area of the device that does not interfere with the operation of the device or along scribe lines on wafer.

The metrology system 310 can include one or more radiation sources (not shown) and one or more radiation detectors not shown). For example, damaged and/or un-damaged measurement structures may be illuminated by an incident beam and one or more diffracted beams may be received and converted into a measured diffraction signal (measured spectral data).

The metrology system 310 can analyze the measured diffraction signal and determine the profile of a damaged and/or un-damaged measurement structure using a library-based process or a regression-based process. Additionally, other linear or non-linear profile extraction techniques are contemplated.

In some embodiments, a Library-Based process can be used for determining the profile of a damaged and/or un-damaged measurement structure. In a library-based process, the measured diffraction signal can be compared to a library of simulated diffraction signals. A simulated diffraction signal in the library can associated with a hypothetical profile of a damaged or an un-damaged measurement structure. When a match is made between the measured diffraction signal and one of the simulated diffraction signals in the library or when the difference of the measured diffraction signal and one of the simulated diffraction signals is within a preset or matching criterion, the hypothetical profile associated with the matching simulated diffraction signal is presumed to represent the actual profile of the damaged or the un-damaged measurement structure. The matching simulated diffraction signal and/or hypothetical profile can then be utilized to determine whether the structure has been fabricated according to specifications. In addition, the matching simulated diffraction signal and/or hypothetical profile can then be utilized to determine whether the structure has been damaged during processing.

The set of hypothetical profiles stored in library 330 can be generated by characterizing a hypothetical profile using a set of parameters, then varying the set of parameters to generate hypothetical profiles of varying shapes and dimensions. The process of characterizing a profile using a set of parameters can be referred to as parameterizing.

In other embodiments, measurement data can be obtained from an optical metrology tool and can include polarization data. The polarization data can be transformed into P-domain data, and the P-domain data can be used in some damage assessment procedures. For example, P-domain signatures may be used to identify specific types and amounts of damage.

Figure 4A:
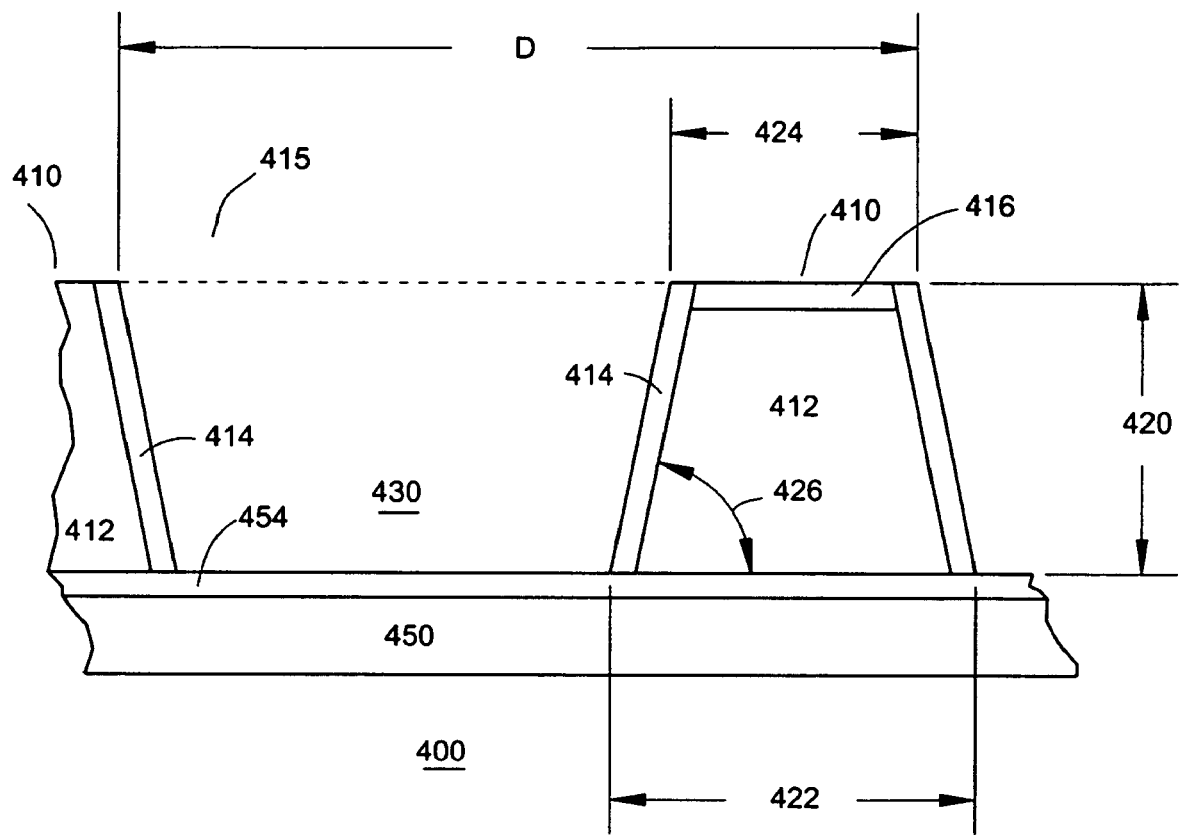
FIGS. 4A and 4B illustrate exemplary structure and hypothetical profile in accordance with embodiments of the invention.

FIG. 4A illustrates an exemplary profile in accordance with embodiments of the invention. In the illustrated embodiment shown in FIG. 4A, an exemplary periodic structure 400 is shown that includes an exemplary hypothetical feature profile 410 is illustrated including a number of characterization parameters such as a height 420, a bottom width 422, a top width 424, a sidewall angle 426. For example, the width of hypothetical profile can be referred to as the critical dimension (CD) and top and/or bottom CDs can be used to describe a hypothetical profile.

The hypothetical profile 410 can include an undamaged portion 412, a first damaged portion 414, and a second damaged portion 416, and the three portions can have different properties associated with them. Alternatively, the first damaged portion 414 and the second damaged portion 416 may have non-uniform and/or discontinuous shapes. For example, the undamaged portion 412 can be low-k and/or ultra low-k material and the first damaged portion 414, and/or the second damaged portion 416, can be damaged low-k and/or ultra low-k material, and the dielectric properties of the three portions can be different. In addition, the first damaged portion 414 and the second damaged portion 416 can include damaged surfaces, damaged edges, and/or damaged corners in a trench and/or via. Alternatively, additional shapes and features of hypothetical profiles and damaged portions may be characterized by using different shapes and/or a different number of parameters. In addition, the shape of the damaged portions can be different than the illustrated shape.

The periodic structure 400 also includes a substrate 450 with an additional layer 454 formed thereon. The substrate 450 can include semiconductor layers comprising materials such as silicon, germanium, or combinations thereof; dielectric layers, and/or metallic layers. The additional layer 454 can comprise a stop layer material. Alternatively, the additional layer may include several layers or may not be required. In addition, the additional layer may comprise a damaged portion (not shown).

The set of hypothetical profiles stored in library 330 (FIG. 3) can be generated by varying the parameters that characterize the hypothetical profile. For example, with reference to FIG. 4A, by varying parameters associated with the periodic structure, hypothetical profiles of varying shapes and dimensions can be generated. Note that one or more of these parameters can be varied at one time.

Figure 4B:
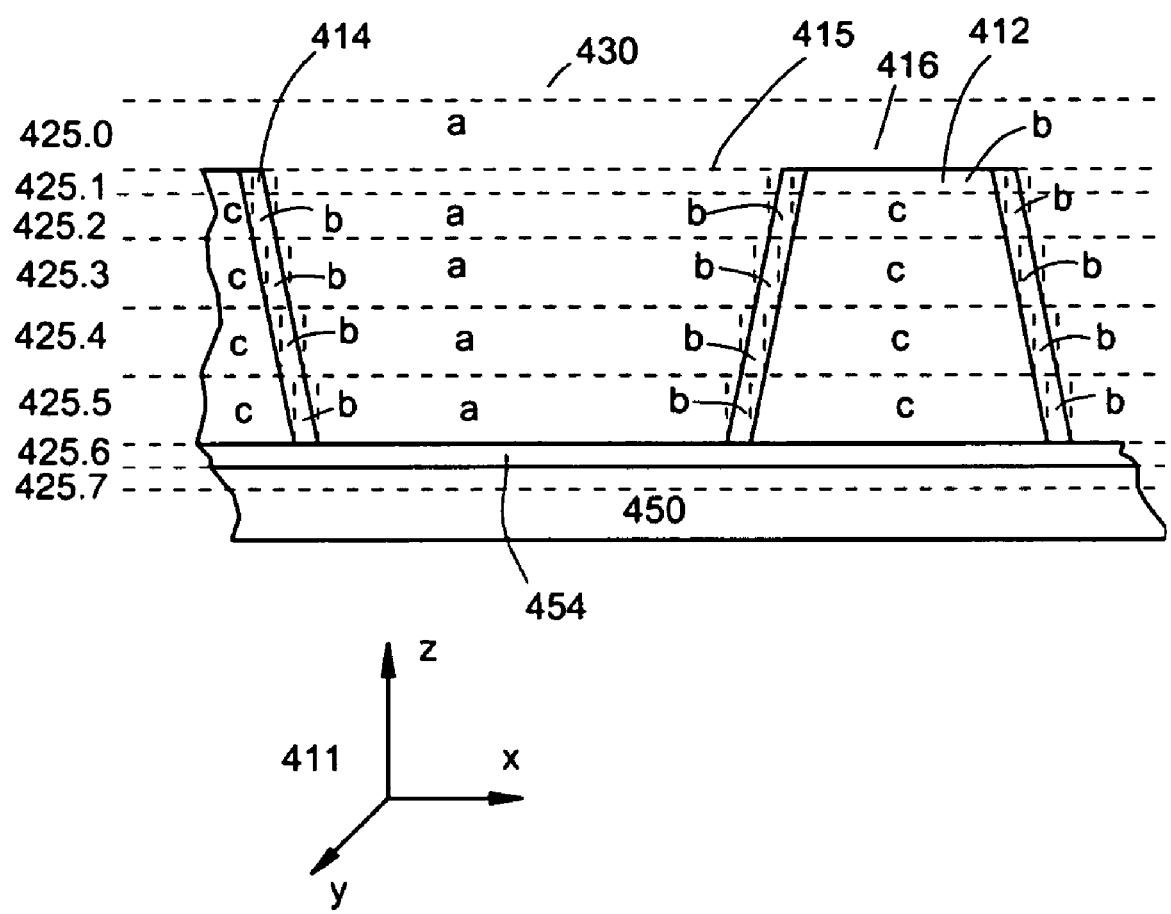

FIG. 4B illustrates an exemplary divisioning of the hypothetical profile of the periodic structure of FIG. 4A into a plurality of expansion layers to allow a mathematical analysis of the diffraction grating in accordance with the present invention. In the coordinate system 411 shown in FIG. 4B, the periodic direction is the x direction, the transverse direction is the z direction, and the y direction is a direction of essentially infinite extension orthogonal to the x direction and z direction normal to the page.

The periodic structure 400 includes a substrate 450 with an additional layer 454 formed thereon. Features 430, such as trenches and/or vias, can be etched in a periodic and/or non-periodic manner in a dielectric layer 415 on the substrate 450. Alternatively, features 430 may be etched in the additional layer 454 on the substrate 450. Damaged dielectric portions 414 are illustrated and can represent top, bottom, and/or sidewall damage to the features 430. Undamaged dielectric portions 412 are illustrated next to the damaged dielectric portions 414. Therefore, the semiconductor device can have three materials occurring along a line in the periodic direction: atmospheric gas, damaged dielectric, and undamaged dielectric.

FIG. 4B illustrates the variables associated with a mathematical description of the dimensions of exemplary damaged periodic structure 400 (i.e., a hypothetical profile defined using profile variables or parameters) according to the present invention. The exemplary hypothetical profile of FIG. 4B has one or more materials per layer: in layer 425.0 a single material is shown and that material is an atmospheric material; in layer 425.1 two materials are illustrated that can include damaged material and atmospheric material; in layers 425.2 through 425.5 three materials are shown including an atmospheric gas material, damaged material, and an undamaged material; in layer 425.6 a single material is shown and that material can be stop layer material; and in layer 425.7 a single material is shown and that material can be substrate material. Alternatively, undamaged material may be shown in 425.1 may be damaged material. In addition, a different number of materials may be present in a layer if damage does not occur uniformly in a surface. The damaged dielectric portions can be considered to be an additional-material deviation prior to discretization. In addition, atmospheric slabs (a) can be considered to be additional-material deviations of the discretized profile. Alternatively, other techniques may be used when other shapes and/or other damaged portions are analyzed.

With reference again to FIG. 3, the number of hypothetical profiles and corresponding simulated diffraction signals in the set of hypothetical profiles and simulated diffraction signals stored in library 330 (i.e., the resolution and/or range of library 330) depends, in part, on the range over which the set of parameters and the increment at which the set of parameters are varied. In one exemplary embodiment, the hypothetical profiles and the simulated diffraction signals stored in library 330 are generated prior to obtaining a measured diffraction signal from an actual structure. Thus, the range and increment (i.e., the range and resolution) used in generating library 330 can be selected based on familiarity with the fabrication process for a structure and what the range of damage is likely to be. The range and/or resolution of library 330 can also be selected based on empirical measures, such as measurements using AFM, X-SEM, CD-SEM, and the like.

For a more detailed description of a library-based process, see U.S. patent application Ser. No. 09/907,488, entitled GENERATION OF A LIBRARY OF PERIODIC GRATING DIFFRACTION SIGNALS, filed on Jul. 16, 2001, which is incorporated herein by reference in its entirety.

In other embodiments, a Regression-Based process can be used for determining the profile of a damaged and/or un-damaged measurement structure. In a regression-based process, the measured diffraction signal is compared to a simulated diffraction signal (i.e., a trial diffraction signal). The simulated diffraction signal is generated prior to the comparison using a set of parameters (i.e., trial parameters) for a hypothetical profile (i.e., a hypothetical profile). If the measured diffraction signal and the simulated diffraction signal do not match or when the difference of the measured diffraction signal and one of the simulated diffraction signals is not within a preset or matching criterion, another simulated diffraction signal is generated using another set of parameters for another hypothetical profile, then the measured diffraction signal and the newly generated simulated diffraction signal are compared. When the measured diffraction signal and the simulated diffraction signal match or when the difference of the measured diffraction signal and one of the simulated diffraction signals is within a preset or matching criterion, the hypothetical profile associated with the matching simulated diffraction signal is presumed to represent the actual profile of a damaged or an un-damaged measurement structure. The matching simulated diffraction signal and/or hypothetical profile can then be utilized to determine whether the structure has been fabricated according to specifications. In addition, the matching simulated diffraction signal and/or hypothetical profile can then be utilized to determine whether the structure has been damaged during processing.

Thus, with reference again to FIG. 3, in one exemplary embodiment, a metrology system 310 can generate a simulated diffraction signal for a hypothetical profile, and then compare the measured diffraction signal to the simulated diffraction signal. In addition, the simulated diffraction signal can be generated using an optimization algorithm, such as global optimization techniques, which includes simulated annealing, and local optimization techniques, which includes steepest descent algorithm.

In one exemplary embodiment, the simulated diffraction signals and hypothetical profiles can be stored in a library 330 (i.e., a dynamic library). The simulated diffraction signals and hypothetical profiles stored in library 330 can then be subsequently used in matching the measured diffraction signal.

For a more detailed description of a regression-based process, see U.S. patent application Ser. No. 09/923,578, entitled METHOD AND SYSTEM OF DYNAMIC LEARNING THROUGH A REGRESSION-BASED LIBRARY GEN- ERATION PROCESS, filed on Aug. 6, 2001, which is incorporated herein by reference in its entirety.

As described herein, simulated diffraction signals are generated that can be compared to measured diffraction signals. In one exemplary embodiment, simulated diffraction signals can be generated by applying Maxwell's equations and using a numerical analysis technique to solve Maxwell's equations, such as rigorous coupled-wave analysis (RCWA). It should be noted, however, that various numerical analysis techniques, including variations of RCWA, could be used. For a more detail description of RCWA, see U.S. patent application Ser. No. 09/770,997, entitled CACHING OF INTRA-LAYER CALCULATIONS FOR RAPID RIGOROUS COUPLED-WAVE ANALYSES, filed on Jan. 25, 2001, which is incorporated herein by reference in its entirety.

As described herein, optical metrology can be used to determine the profile of a damaged and/or undamaged structure formed on a semiconductor wafer. More particularly, various deterministic characteristics of the structure (e.g., height, width, critical dimension, line width, and the like) can be determined using optical metrology. Thus, the profile of the structure obtained using optical metrology is the deterministic profile of the structure. However, the structure may be formed with various stochastic effects, such as damaged surfaces, damaged edges, and/or damaged corners, and the like.

In various exemplary embodiments, to more accurately determine the overall profile of the structure and to assess damage to dielectric material in the structure, one or more of these stochastic effects can also be measured using optical metrology. It should be recognized that the terms surface damage, edge damage, and/or corner damage could be used to refer to characteristics of damaged structures other than just lines. In one example, when assessing damage to a dielectric layer, the measurable damage to multi-dimensional structures, such as trenches, vias and/or holes, can be described, measured, and modeled as edge damage and/or corner damage. In another example, when assessing damage to a dielectric layer, the measurable damage to multi-dimensional structures, such as trenches, vias and/or holes, can be described, measured, and modeled as surface damage, and damaged surfaces can include top, bottom, and sidewall surfaces. Thus, in the following description, the terms corner damage, edge damage, and surface damage can be also used in a broad sense.

Low-k damage can be due to ion bombardment, and surfaces having the largest amount of bombardment will have the most damage. Ion bombardment can be due to direct exposure or indirect (backscatter) exposure. Additional damage can occur due to process by-products.

Figure 5A:
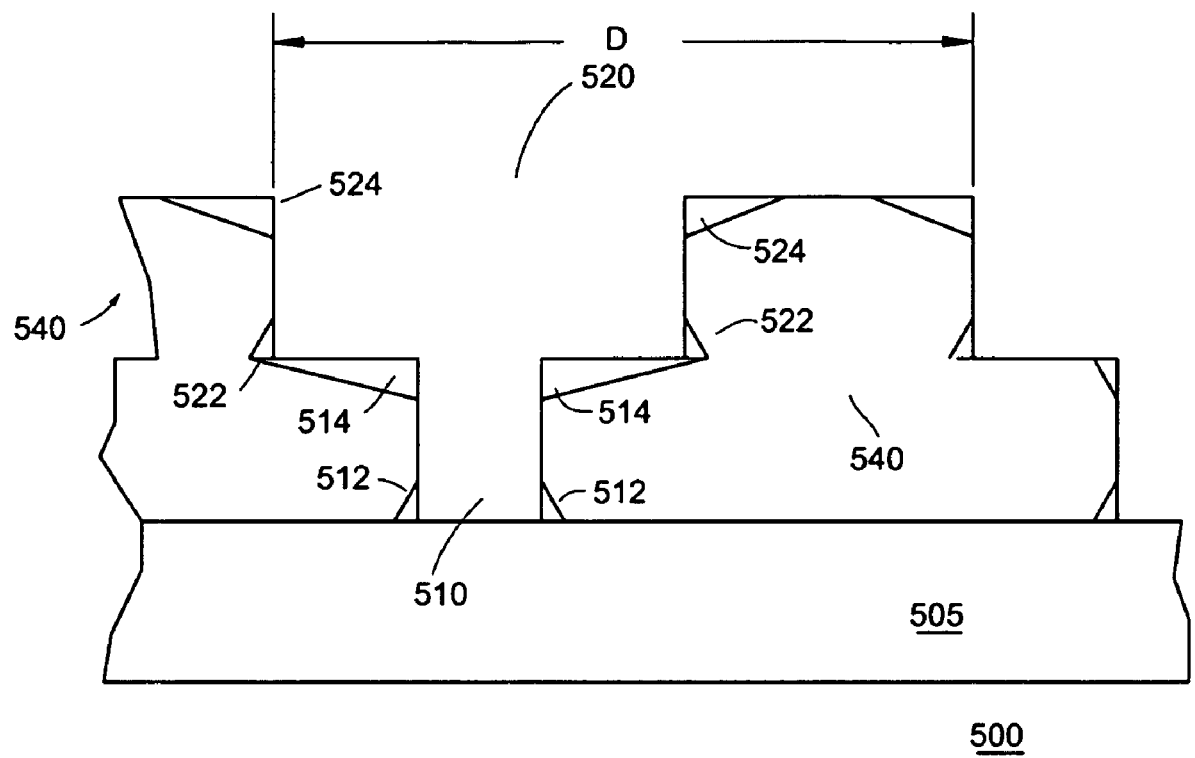
FIGS. 5A and 5B illustrate additional exemplary structure and hypothetical profile in accordance with embodiments of the invention.
Figure 5B:
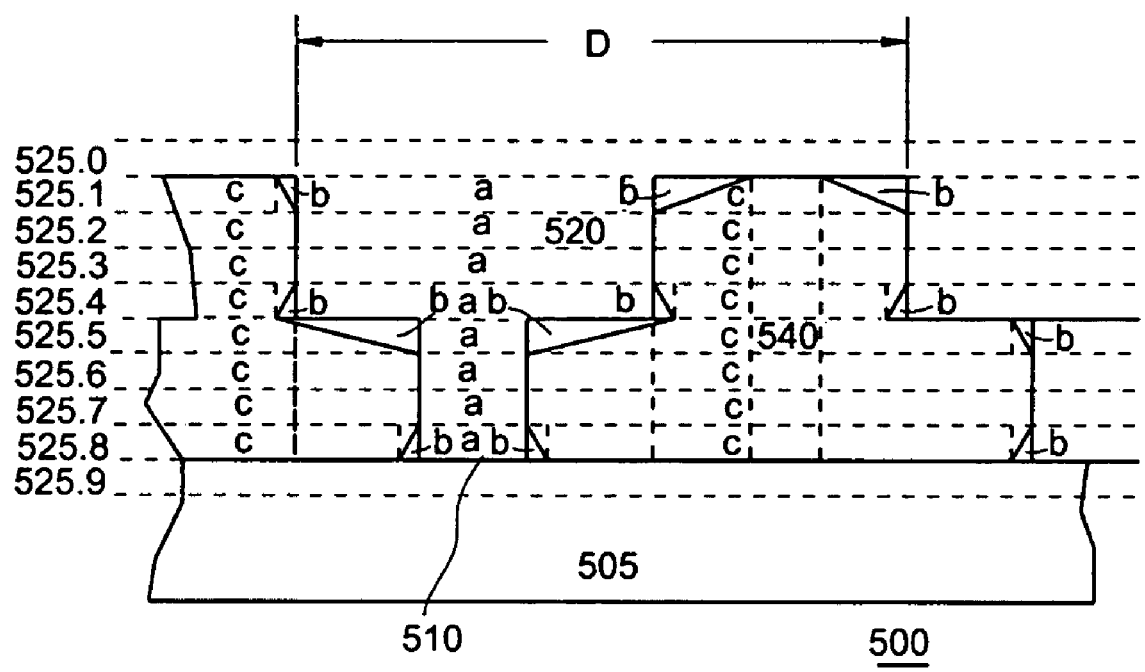

FIGS. 5A and 5B illustrate additional dual damascene structures in accordance with exemplary embodiments of the invention. A dual damascene structure 500 is shown having a via portion 510 and a trench portion 520. As depicted in FIGS. 5A and 5B, dual damascene structure 500 can include one or more areas (512, 514, 522, and 524) that can illustrate damaged material rather than undamaged material 540. In addition, the shape of the dual damascene structure 500 can include types of structures formed on a semiconductor wafer, such as periodic gratings, lines, vias, holes, multilayer structures, and the like. Furthermore, the undamaged material may include one or more of the following materials: TEOS, OSG, and Coral.

The dual damascene structure 500 also includes a substrate 505, and the substrate 505 can include semiconductor layers comprising materials such as silicon, strained silicon, germanium, or combinations thereof, dielectric layers, and/or metallic layers. Alternatively, the additional layer may be shown on the substrate.

The set of hypothetical profiles stored in library 330 (FIG. 3) can be generated by varying the parameters that characterize the hypothetical profile. For example, with reference to FIGS. 5A, 5B, by varying parameters associated with the periodic structure, the undamaged areas, and the damaged areas, hypothetical profiles of varying shapes and dimensions can be generated. Note that one or more of these parameters can be varied at one time.

FIG. 5B illustrates an exemplary divisioning of the periodic structure of FIG. 5A into a plurality of expansion layers to allow a mathematical analysis of the diffraction grating in accordance with embodiments of the invention. In the coordinate system 511 shown in FIG. 5B, the periodic direction is the x direction, the transverse direction is the z direction, and the y direction is a direction of essentially infinite extension orthogonal to the x direction and z direction normal to the page.

The dual damascene structure 500 includes a substrate 505 with one or more layers (not shown) formed therein. Features, such as trenches 520 and/or vias 510, can be etched in a periodic and/or non-periodic manner in a dielectric layer 545 on the substrate 550. Alternatively, trenches 520 and/or vias 510 may be etched in one or more additional layers (not shown) on the substrate 505. Atmospheric gas slabs "a" are shown; damaged dielectric portions "b" are illustrated and can represent surface, edge, and/or corner damage to the trenches 520 and/or vias 510; and undamaged dielectric portions "c" are also shown. The damaged dielectric portions "b" are shown as triangles, but other sizes and other shapes can be used. For example, triangles can be used to illustrate a non-uniform damage, and other shapes can be used to show other types of damage. As illustrated, the periodic structure can have a different number of materials occurring along a line in the periodic direction. For example, the materials can include atmospheric gas, damaged dielectric, and undamaged dielectric. Alternatively, photoresist materials, ARC materials, BARC materials, TERA materials, and/or stop layer materials may be included.

In various embodiments, the periodic structure can have one or more damaged areas having different shapes, and the methods of the invention can be adjusted accordingly. A process may produce damage to the trenches and/or vias, and methods can be adjusted to model and/or analyze various damage scenarios. In addition, libraries and regression techniques can be established for periodic structures having damaged dielectric in one or more of the areas shown in FIGS. 5A and 5B.

FIG. 5B illustrates the variables associated with a mathematical description of the dimensions of exemplary damaged periodic structure 500 (i.e., a hypothetical profile defined using profile variables or parameters) according to embodiments of the invention. The exemplary hypothetical profile of FIG. 5B has one or more materials per layer: in layer 525.0 a single material is shown and that material is an atmospheric material; in layers 525.1, 525.4, 525.5, and 525.8 three materials are shown including an atmospheric gas material, damaged dielectric material, and an undamaged dielectric material; in layers 525.2, 525.3, 525.6, and 525.7 two materials are shown including an atmospheric gas material, and an undamaged dielectric material; and in layer 525.9 a single material is shown and that material can be substrate material. Alternatively, a different number of layers may be used and/or a different number of materials may be present in other damage assessment scenarios.

In some embodiments, additional material techniques can be used to measure, analyze, and/or model a periodic structure having one or more damaged areas. The damaged dielectric portions can be considered to be an additional-material deviation prior to discretization. In addition, atmospheric slabs (a) can be considered to be additional-material deviations of the discretized profile.

In other embodiments, edge damage and/or corner damaged, as shown in FIGS. 5A and 5B, can be measured using a root-means-square (rms) value, which describes the fluctuations of damage thickness (at the edge and/or corner) around an average layer thickness. One or more of the damaged areas (512, 514, 522, and 524) of structure 500 can be modeled in optical metrology using one or more random spatial critical dimension (CD) variations.

With reference to FIGS. 5A and 5B, the optical properties of an inhomogeneous medium can be described by a complex dielectric function and a complex magnetic permeability, each of which is a function of position. If the wavelength of the electromagnetic radiation (i.e., the incident beam) used to measure the inhomogeneous medium is much larger than the particle size in the damaged area (e.g., for normal incidence with wavelength greater than 1.3 of the spatial period), classical theories of inhomogeneous media presume that the material can be treated as a homogeneous substance with an effective dielectric function and effective magnetic permeability. These quantities depend upon the properties of the constituents, as well as their volume fractions and sizes. In the general case, the resulting effective material will be anisotropic, i.e., the effective refraction index is a tensor.

A simulated diffraction signal for structure having one of more damaged areas can be generated for optical metrology using an exemplary structure as illustrated in FIGS. 4A, 4B, 5A, and 5B. For example, an exemplary structure may include one or more undamaged areas and one or more damaged areas. In generating a simulated diffraction signal for an exemplary structure, the refraction index used for undamaged area can be assumed to be the same as that of the material in the layer (e.g., dielectric). The refraction index used for damaged areas can be assumed to be an effective refraction index, which can be an average between the two materials that form the damaged area (e.g., dielectric and air).

In one exemplary embodiment, weighted average may be used. For example, assuming an azimuth angle of zero, the effective refraction index for TE- and TM-polarized light can be derived using the following:

$$TE: \epsilon = ((\omega_1 * \epsilon_1) + (\omega_2 * \epsilon_2))/(\omega_1 + \omega_2)$$

$$TM: \epsilon^{-1} = ((\omega_1 * (\epsilon_1)^{-1}) + (\omega_2 * (\epsilon_2)^{-1}))/(\omega_1 + \omega_2)$$

$\omega_1$ and $\omega_2$ are weighing factors corresponding to percentage of volume. For example, if the volume of the damaged area includes two percent of a first material (e.g., air) and 98 percent of a second material (e.g., dielectric), then $\omega_1$ is 0.02 and $\omega_2$ is 0.98. The effective refraction index can then be used in generating a simulated diffraction signal used in optical metrology.

Additionally, with reference to FIGS. 4B and 5B, the hypothetical profiles of representative structures 400 and 500 can be divided into multiple effective medium layers (i.e., layers $t_i$ to $t_n$). As depicted in FIGS. 4B and 5B, each effective medium layer can include an undamaged area and damaged areas. As also depicted in FIGS. 4B and 5B, the thickness of the multiple effective medium layers can be varied. Additionally, the ratio between the undamaged area and damaged areas, which corresponds to the values of $\omega_1$ and $\omega_2$ as described above, can be varied. The effective refraction indices can then be used in generating a simulated diffraction signal used in optical metrology.

Figure 5B:
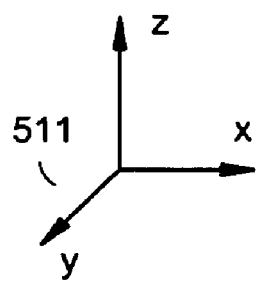

More particularly, in library-based optical metrology, a set of hypothetical profiles and corresponding simulated diffraction signals can be generated for varying amounts of damage for structure 500 (FIG. 5). Thus, a measure of damage (e.g., rms damage) can be used as one of the parameters to characterize a hypothetical profile in generating a library of hypothetical profiles and corresponding simulated diffraction signals. The amount of damage of an actual structure can then be measured by obtaining a measured diffraction signal of the actual structure, comparing the measured diffraction signal to the library of simulated diffraction signals to determine a matching simulated diffraction signal and the hypothetical profile corresponding to the matching simulated diffraction signal. A damage measurement for the structure can then be determined based on the outer layer of the hypothetical profile corresponding to the matching simulated diffraction signal.

In regression-based optical metrology, a simulated diffraction signal can be generated assuming a certain amount of damage for an actual structure. The simulated diffraction signal can be compared to a measured diffraction signal of the actual structure. If the simulated diffraction signal matches the measured diffraction signal, the actual structure can be assumed to have the amount of damage assumed in generating the simulated diffraction signal. If the simulated diffraction signal does not match the measured diffraction signal, then another simulated diffraction signal can be generated using another amount of damage and compared to the measured diffraction signal.

In still other exemplary embodiments, damage measurements of a structure can be obtained using total scattering/total integrated scattering (TS/TIS) and angle resolved scattering (ARS).

Figure 6:
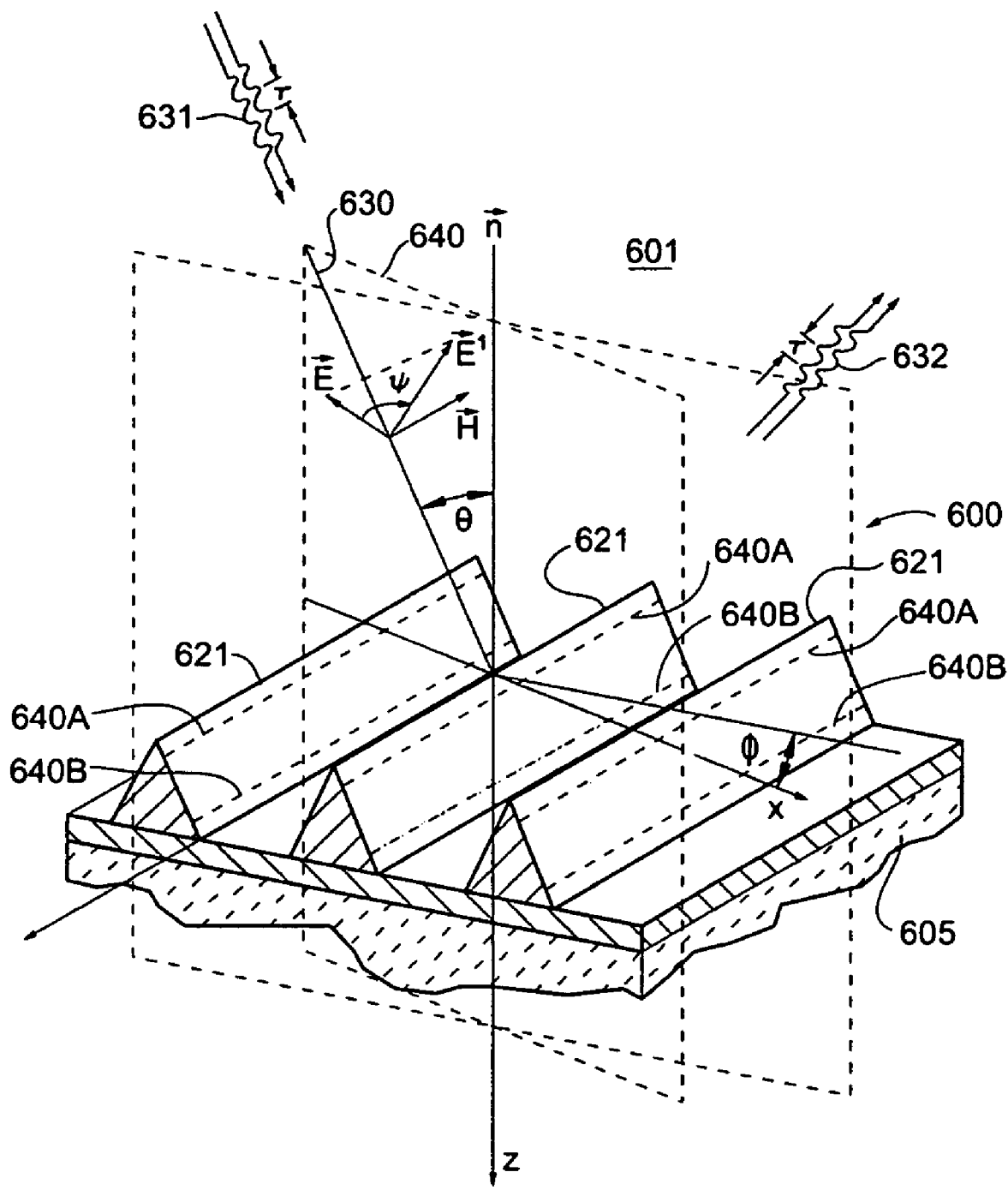
FIG. 6 illustrates a simplified schematic diagram of a section of a measurement structure in accordance with embodiments of the invention.

FIG. 6 illustrates a simplified schematic diagram of a section of a measurement structure in accordance with embodiments of the invention. In the illustrated embodiment, a section of a periodic structure/grating 600 is shown having damaged areas 640A and 640B. For example, with reference to FIG. 6, assume that the structure is a periodic grating/structure formed on a semiconductor wafer with a regular line/space pattern. As noted above; it should be recognized that the structure could be various types of structures formed on a semiconductor wafer, such as lines, vias, holes, and the like.

In the present example, as depicted in FIG. 6, assume that regular line/space pattern of the periodic grating/structure includes a damaged edge 640A and/or a damaged corner 640B and one or more of these surfaces can be characterized by using an edge roughness parameter and/or a surface roughness parameter. To measure the damaged surface, the regular line/space pattern can be considered as a periodic structure in one lateral direction (x) and a stochastic structure in a first orthogonal direction (y), and/or a second orthogonal direction (z). Thus, as depicted in FIG. 6, when illuminated with white or monochromatic light, depending on the azimuth angle φ of incidence, the edge and/or corner damage (640A and 640B) can cause an additional light response pattern that will for the most general case (φ≠0) be multi-dimensional.

For example, when using ARS to measure damaged structures, the optical metrology system 300 (FIG. 3) can include an array of detectors, and a lens system to direct the reflected light onto array of detectors, which may record the angular distribution of the scattered light.

For example, when a damaged surface has a rms surface damage that is less than a quarter of the sensing wavelength (Rayleigh criterion), the measured angle resolved intensity distribution, which is referred to as bi-directional reflection distribution function (BRDF) directly translates into a power spectrum density (PSD) of the damaged surface. A PSD can be used to illustrate how much the various spatial frequencies contribute to the overall roughness of a damaged surface and/or layer. Additionally, a Fourier transform of the PSD is the auto-correlation function (ACF) of the surface. See, John C. Stover, "Optical Scattering", SPIE Optical Engineering Press, Second Edition, Bellingham Wash. 1995, which is incorporated herein by reference in its entirety.

In addition to measuring the damaged portion of the structure, one or more of the signals from one or more of the detectors in the metrology system 310 can be used to extract the deterministic profile of the undamaged portion of the structure. For example, a detector that corresponds to a detector in the specular direction may be used to generate the simulated diffraction signal used in the library-based and/or regression-based process described above to determine the deterministic profile of the undamaged portion of the structure.

In one embodiment, when using TS/TIS to measure damage, a reflecting sphere, such as a Coblentz sphere, can integrate and direct the scattered light onto a detector. The signal from this detector can then be used to determine the damaged portion. As noted above, for a damaged surface and/or damaged layer with a rms surface roughness less than a quarter of the sensing wavelength (Rayleigh criterion), the measured scattered light is directly proportional to the rms roughness of the damaged surface and/or damaged layer.

Additionally, when using TS/TIS techniques to measure damage, the detected signal can be used to determine the deterministic profile of the undamaged portion of the structure. More particularly, the detected signal can be used to generate the simulated diffraction signal used in the library-based and/or regression-based process described above to determine the deterministic profile of the undamaged portion of the structure.

Furthermore, TS/TIS techniques can be used to measure multi-dimensional structures, and the resulting diffraction/scatter pattern from multi-dimensional structures are more complicated since diffraction and scattering occurs in multiple dimensions. For example, the diffraction peaks can be smeared out in one or more dimensions.

In alternate embodiments, detectors can be arranged in two or more dimensions to measure damaged and/or the undamaged portions of multi-dimensional structure.

Various techniques can be used to measure the presence of edge roughness on or within features of a patterned wafer and these techniques can be used to measure edge and/or corner damage. These techniques are taught in co-pending U.S. patent application Ser. No. 10/428,186, entitled EDGE ROUGHNESS MEASUREMENT IN OPTICAL METROLOGY, by Bischoff, et al., filed on May 2, 2003, and ODP techniques covering the measurement of multiple layers are taught in U.S. Pat. No. 6,743,646, entitled BALANCING PLANARIZATION OF LAYERS AND THE EFFECT OF UNDERLYING STRUCTURE ON THE METROLOGY SIGNAL", by Jakatdar, et al., filed on Oct. 22, 2001, and these two patent applications are incorporated by reference herein.

Referring back to FIG. 6, in the illustrated embodiment, a section of a periodic structure/grating 600 is shown that includes three ridges 621 that are shown as having a triangular cross-section. In other embodiments, the method of the invention is applicable to cases where the ridges have shapes that are considerably more complex, and even to cases where the categories of "ridges" and "troughs" may be ill defined. According to the lexography of the present specification, the term "ridge" will be used for one period of a periodic structure on a substrate. Each ridge 621 of FIG. 6 is considered to extend infinitely in the +y and −y directions, and an infinite, regularly spaced series of such ridges 621 are considered to extend in the +x and −x directions. The ridges 621 are atop a deposited film 610, and the film 610 is atop a substrate 605 which is considered to extend semi-infinitely in the +z direction. The normal vector n to the periodic grating/structure is in the −z direction.

In addition, FIG. 6 illustrates the variables associated with a mathematical analysis of a diffraction grating in accordance with embodiments of the invention. In particular:

$\theta$ is the angle between the Poynting vector of the incident electromagnetic radiation 631 and the normal vector n of the periodic grating/structure 600. The Poynting vector and the normal vector n define the plane of incidence 640.

$\phi$ is the azimuthal angle of the incident electromagnetic radiation 631, i.e., the angle between the direction of periodicity of the grating, which in FIG. 6 is along the x-axis, and the plane of incidence 640. (For ease of presentation, in the mathematical analysis of the present specification the azimuthal angle $\phi$ is set to zero.)

$\psi$ is the angle between the electric-field vector $\vec{E}$ of the incident electromagnetic radiation 631 and the plane of incidence 640, i.e., between the electric field vector $\vec{E}$ and its projection $\vec{E}'$ on the plane of incidence 640. When $\phi=0$ and the incident electromagnetic radiation 631 is polarized so that $\psi=\Pi/2$, the electric-field vector $\vec{E}$ is perpendicular to the plane of incidence 640 and the magnetic-field vector $\vec{H}$ lies in the plane of incidence 640, and this is referred to as the TE polarization. When $\Phi.phi.=0$ and the incident electromagnetic radiation 631 is polarized so that $\psi=0$, the magnetic-field vector $\vec{H}$ is perpendicular to the plane of incidence 640 and the electric-field vector $\vec{E}$ lies in the plane of incidence 640, and this is referred to as the TM polarization. Any planar polarization is a combination of in-phase TE and TM polarizations. The method of the present invention described below can be applied to any polarization that is a superposition of TE and TM polarizations by computing the diffraction of the TE and TM components separately and summing them. Furthermore, although the 'off-axis' $\phi \neq 0$ case is more complex because it cannot be separated into TE and TM components, embodiments of the present invention are applicable to off-axis incident radiation as well.

$\lambda$ is the wavelength of the incident electromagnetic radiation 631.

Figure 7:
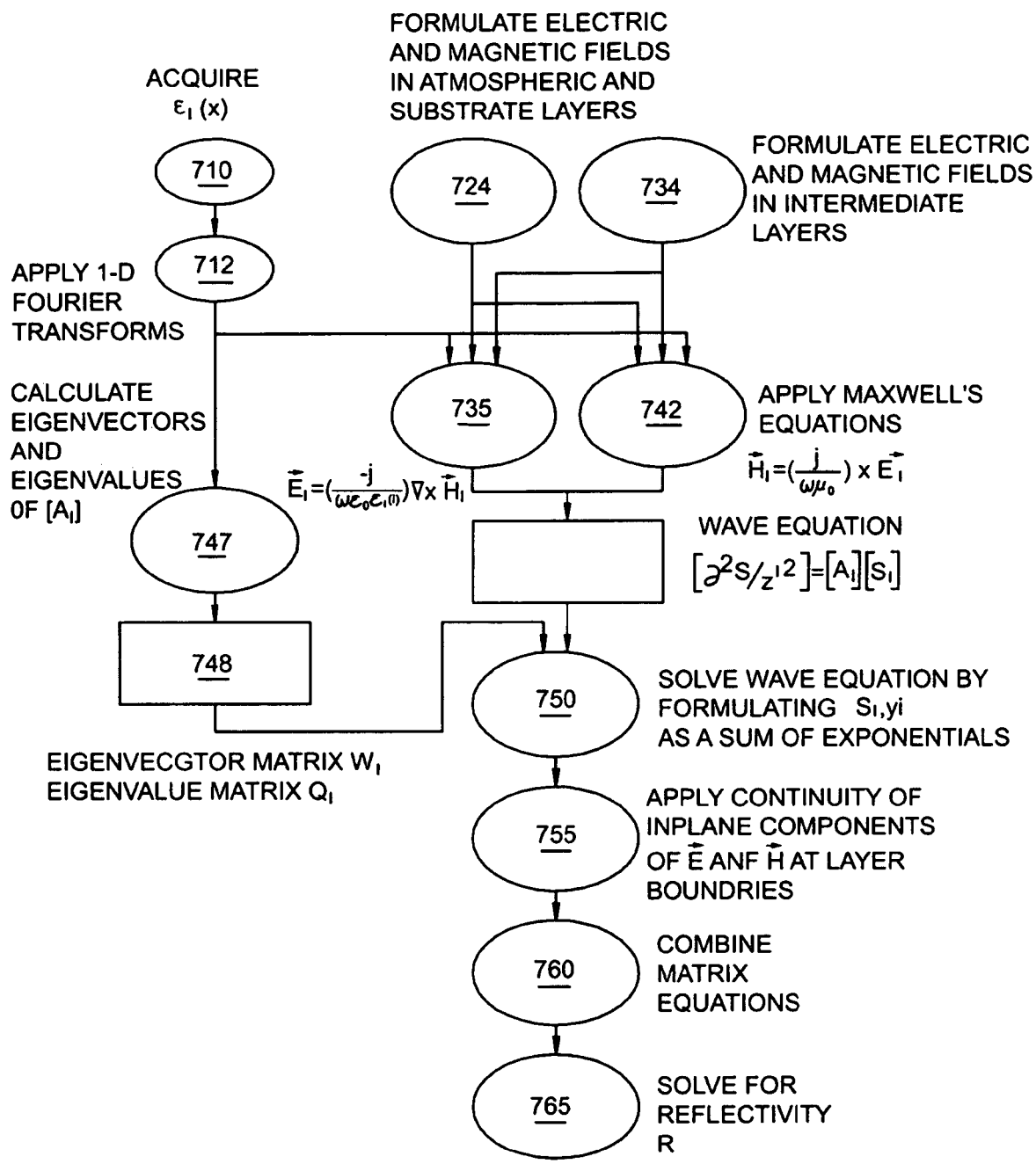
FIG. 7 shows a method for operating an optical metrology system in accordance with embodiments of the invention.

FIG. 7 shows a method for operating an optical metrology system in accordance with embodiments of the invention. FIG. 7 illustrates a flow chart for another method of determining a diffracted reflectivity of a damaged periodic structure. In the illustrated embodiment, a periodic structure is examined using additional material deviations techniques, and using the hypothetical layer data. This technique results in a periodic structure/grating with one or more materials occurring along a periodic direction. FIG. 7 illustrates a method for determining one or more permittivity functions of a damaged periodic structure having one or more materials occurring along a periodic direction, and the permittivity functions can be measured, analyzed, and/or modeled using hypothetical layer data. For example, hypothetical layer data can be used to generate a theoretical or simulated diffracted reflectivity of the damaged periodic structure that can include damaged and/or undamaged materials.

FIG. 7 illustrates a process flow for a TE-polarization rigorous coupled-wave analysis. Alternatively, a TM-polarization rigorous coupled-wave analysis may be used.

Figure 8:
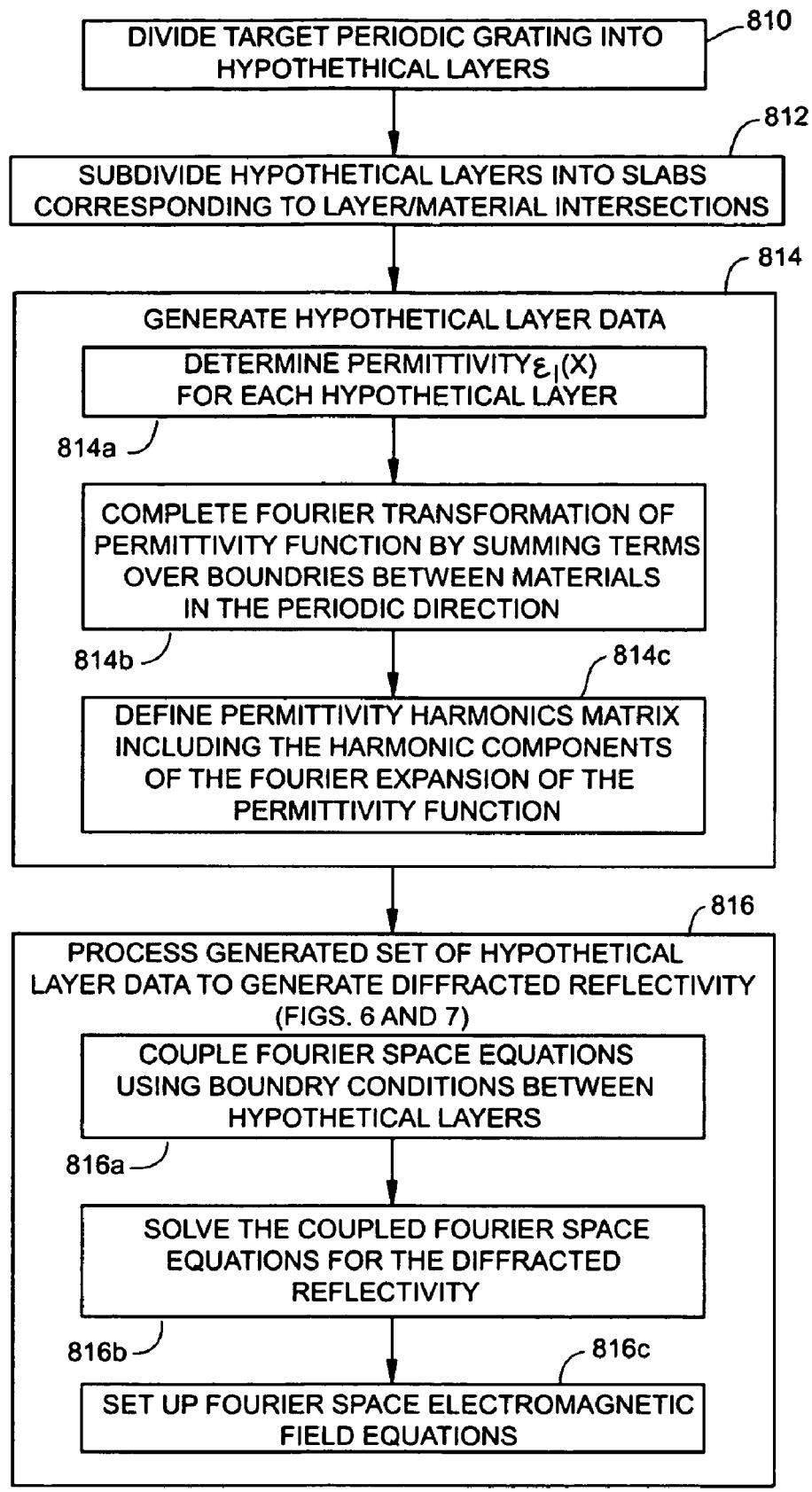
FIG. 8 shows another method for operating an optical metrology system in accordance with embodiments of the invention.

FIG. 8 illustrates another method for operating an optical metrology system in accordance with embodiments of the invention. In step 810, the damaged periodic structure (i.e. target periodic grating 600 shown in FIG. 6) can be divided into hypothetical harmonic expansion layers. Referring again to FIGS. 4B and 5B, L+1 can be used to illustrate the number of the harmonic expansion layers into which the system is divided. Harmonic expansion layers "0" and L can be considered to be semi-infinite layers. Harmonic expansion layer "0" can be an "atmospheric" layer, such as a process gas, a vacuum, or air, which can have a refractive index $n_o$ near unity. Harmonic expansion layer L can be a "substrate" layer, which is typically a semiconductor such as silicon or germanium or a combination thereof in semiconductor applications. In each illustrated case, there are a number of harmonic expansion layers, with an atmospheric layer above the structure being the "zeroth" harmonic expansion layer. Generically or collectively, the harmonic expansion layers are assigned reference numerals, and, depending on context, the harmonic expansion layers may be considered to include different materials. As shown in FIGS. 4B and 5B, the harmonic expansion layers are formed parallel to the direction of periodicity of the periodic structure. Alternatively, layers that form an angle with the direction of periodicity of the measurement structure (grating) may also be measured.

Referring again to FIG. 8, after dividing the periodic structure into the hypothetical harmonic expansion layers as described above, in step 912, the hypothetical harmonic expansion layers are further divided into slabs defined by the intersections of the harmonic expansion layers with the materials forming the damaged periodic structure. As shown in FIGS. 4B and 5B, the section of each material within each intermediate harmonic expansion layers can be approximated using one or more planar slabs of rectangular cross-section "a", "b", and "c". The top and bottom surfaces of each slab are located at the boundaries between harmonic expansion layers. The side surfaces of each slab are vertical and are located at the boundary between materials when that boundary is vertical, or across the boundary between materials when that boundary is not vertical. Clearly, any geometry of exemplary periodic structure with a cross-section which does not consist solely of vertical and horizontal borders can be better approximated using a greater number of harmonic expansion layers.

Other parameters shown in FIGS. 4-6 are as follows:

D is the periodicity length or pitch, i.e., the length between equivalent points on pairs of adjacent ridges.

$x^{(l)}_k$ is the x coordinate of the starting border of the $k^{th}$ material in the $l^{th}$ layer, and $x^{(l)}_{k-1}$ is the x coordinate of the ending border of the $k^{th}$ material in the $l^{th}$ layer, so that $x^{(l)}_k - x^{(l)}_{k-1}$ is the width of the $k^{th}$ slab in the $l^{th}$ layer. For example, as shown in FIG. 4B, $x^{(l)}_2 - x^{(l)}_1$ is the width of the damaged dielectric slab "b".

$t_l$ is the thickness of the $l^{th}$ layer for $1 < l < (L-1)$. In one exemplary embodiment, the thicknesses $t_l$ of the layers can be chosen so that (after the discretization of the profile) every vertical line segment within each layer passes through only a single material. However, when non-linear damage occurs, prior to discretization, a vertical line in the region of slab "b" may pass through a boundary between the atmospheric material and the damaged dielectric material. Thus, a smaller discretization process may be performed using a step-wise approximation for the non-linear segments to reduce the number and size of the regions where a vertical line in the region passes through the atmospheric material and the damaged dielectric material.

$n_k$ is the index of refraction of the kth material in the periodic structure.

In determining the diffraction generated by a periodic structure, as discussed herein, a Fourier space version of Maxwell's equations can be used. Referring again to FIG. 8, to generate these equations, in step 814, hypothetical layer data is generated by completing a harmonic expansion of a function of the permittivities of the materials in the damaged periodic structure.

In Step 814a of FIG. 8 (step 710 of FIG. 7 for TE polarization) the permittivities $\varepsilon_l(x)$ for each layer l are determined or acquired as is known by those skilled in the art and disclosed, for example, in U.S. patent application Ser. No. 09/728,146 filed Nov. 28, 2000, entitled PROFILER BUSINESS MODEL, by Niu et al., which is incorporated herein by reference in its entirety. A one-dimensional Fourier transformation of the permittivity $\varepsilon_l(x)$ or the inverse permittivity $\pi_l(x) = 1/\varepsilon_l(x)$ of each layer l is performed in step 814b of FIG. 8 (step 712 of FIG. 7 and step 812 of FIG. 8) along the direction of periodicity, x, of the periodic structure to provide the harmonic components of the permittivity $\varepsilon_{l,i}$ or the harmonic components of the inverse permittivity $\pi_{l,i}$ where i is the order of the harmonic component.

In particular, the real-space permittivity $\varepsilon_l(x)$ of the $l^{th}$ layer is related to the permittivity harmonics $\varepsilon_l(x)$ of the $l^{th}$ layer by $$\varepsilon_l(x) = \sum_{i=-\infty}^{\infty} \varepsilon_{l,i} \exp\left(j\frac{2\pi i}{D}x\right). \qquad 1.1.1$$

Therefore, via the inverse transform, $$\varepsilon_0 = \sum_{k=1}^{r} n_k^2 \frac{x_{k-1} - x_k}{D}, \qquad 1.1.2$$

and for i not equal to zero, $$\varepsilon_{l,i} = \sum_{k=1}^{r} \frac{n_k^2}{-ji2\pi}\left[\left(\cos\left(\frac{2i\pi}{D}x_k\right) - \cos\left(\frac{2\pi i}{D}x_{k-1}\right)\right) - j\left(\sin\left(\frac{2i\pi}{D}x_k\right) - \sin\left(\frac{2i\pi}{D}x_{k-1}\right)\right)\right]. \qquad 1.1.3$$

The sum is over the number r of borders and $n_k$ is the index of refraction of the material between the $k^{th}$ and the $(k-1)^{th}$ border and j is the imaginary number defined as the square root of $-1$. Similarly, the inverse of the permittivity, $\pi_{l,i}$, of the $l^{th}$ layer is related to the inverse-permittivity harmonics $\pi_{l,i}$ of the $l^{th}$ layer by $$\pi_l(x) = \sum_{i=-\infty}^{\infty} \pi_{l,i} \exp\left(j\frac{2\pi i}{D}x\right). \qquad 1.1.4$$

Therefore, via the inverse transform, $$\pi_0 = \sum_{k=1}^{r} n_k^{-2} \frac{x_{k-1} - x_k}{D}, \qquad 1.1.5$$

and for i not equal to zero, $$\pi_{l,i} = \sum_{k=1}^{r} \frac{n_k^{-2}}{-ji2\pi}\left[\left(\cos\left(\frac{2i\pi}{D}x_k\right) - \cos\left(\frac{2\pi i}{D}x_{k-1}\right)\right) - j\left(\sin\left(\frac{2i\pi}{D}x_k\right) - \sin\left(\frac{2i\pi}{D}x_{k-1}\right)\right)\right]. \qquad 1.1.6$$

The sum is over the number r of borders and $n_k$ is the index of refraction of the material between the $k^{th}$ and the $(k-1)^{th}$ border and j is the imaginary number defined as the square root of $-1$. It is important to note that equations for the harmonic components of the permittivity $\in$ or inverse permittivity $\pi$ provided previously are formulated as a sum over materials, and are only directed toward situations where each harmonic expansion layer has only one or two materials. In contrast, equations (1.1.2) and (1.1.3) and equations (1.1.5) and (1.1.6) are formulated as sums over the boundaries between different materials occurring in the periodic direction, and can handle geometries with any number of materials in a harmonic expansion layer.

Referring again to FIG. 8, in step 816, the sets of hypothetical layer data generated as described above are processed to generate the diffracted reflectivity. This step involves three general sub-steps: First, in sub-step 816a, Fourier space electromagnetic field equations are set up in each of the hypothetical layers using the harmonic expansion of the permittivity function. Second, in sub-step 816b, these Fourier space equations are coupled using boundary conditions between harmonic expansion layers. Finally, in sub-step 916c, the coupled Fourier space equations are solved to provide the diffracted reflectivity. These sub-steps are explained herein with reference to the corresponding step in the flow charts of FIG. 7.

To set up the Fourier space electromagnetic field equations, it is convenient to define the (2o+1)×(2o+1) Toeplitz-form, permittivity harmonics matrix $E_l$ in step 814c of FIG. 8. This permittivity harmonics matrix includes the harmonic components of the Fourier Expansion of the permittivity $\in_l(x)$ and is defined as:

$$E_l = \begin{bmatrix} \varepsilon_{l,0} & \varepsilon_{l,-1} & \varepsilon_{l,-2} & \cdots & \varepsilon_{l,-2o} \\ \varepsilon_{l,1} & \varepsilon_{l,0} & \varepsilon_{l,-1} & \cdots & \varepsilon_{l,-(2o-1)} \\ \varepsilon_{l,2} & \varepsilon_{l,1} & \varepsilon_{l,0} & \cdots & \varepsilon_{l,-(2o-2)} \\ \cdots & \cdots & \cdots & \cdots & \cdots \\ \varepsilon_{l,2o} & \varepsilon_{l,(2o-1)} & \varepsilon_{l,(2o-2)} & \cdots & \varepsilon_{l,0} \end{bmatrix}.$$

A similar permittivity harmonics matrix can be defined to include the harmonic components of the Fourier expansion of the inverse permittivity $\pi_l(x)$.

In the solving process, components of the outgoing wave vectors can be assumed to satisfy the Floquet condition (which is also called Bloch's Theorem, see Solid State Physics, N. W. Ashcrof and N. D. Mermin, Saunders College, Philadelphia, 1976, pages 133-134) in each of the layers containing the periodic ridges, and therefore, due to the boundary conditions, in the atmospheric layer and the substrate layer as well.

When solving for the electric field in the atmospheric layer, although it can be expanded using plane waves, is not determined via a Fourier transform of a real-space formulation. Rather, the formulation is produced a priori based on the Floquet condition and the requirements that both the incoming and outgoing radiation have wave vectors of magnitude $n_0 k_0$. Similarly, the plane wave expansion for the electric field in the substrate layer can be produced a priori. In the substrate layer, the electric field E is formulated as a transmitted wave which is a sum of plane waves-where the x-components $k_{xi}$ of the wave vectors ($k_{xi}$, $k_{0,zi}$) satisfy the Floquet condition.

The plane wave expansions for the electric and magnetic fields in the intermediate layers (425.1 through 425.(L-1) of FIG. 4B, and 525.1 through 525.(L-1) of FIG. 5B) are also, referring again to FIG. 7, produced (step 734) a priori based on the Floquet condition. The electric field $E_{l,y}$ in the $l^{th}$ layer is formulated (step 734) as a plane wave expansion along the direction of periodicity.

Similarly, the magnetic field $H_{l,y}$ in the $l^{th}$ layer is formulated (step 734) as a plane wave expansion along the direction of periodicity. Maxwell's equations may be used to relate the electric and magnetic fields within a layer.

As shown in FIG. 8, (sub-step 816b) the Fourier space equations can be coupled using boundary conditions between the harmonic expansion layers. Applying (steps 741 and 742) Maxwell's equations can provide relationships between the electric and magnetic field harmonic amplitudes of the $l^{th}$ layer.

Combining results from Maxwell's equations and truncating the calculation to order "o" in the harmonic amplitude "S" provides (step 745) a second-order differential matrix equation having the form of a wave equation.

In step 747, an eigen-equation can be solved, that is eigenvectors and eigenvalues can be calculated. In step 748, a diagonal eigenvalue matrix can be formed. In 750, the wave equation can be solved and a homogenous solution can be obtained using the sum of the exponentials.

In step 755, constants in the homogeneous solution can be determined by applying the requirement that the tangential electric and magnetic fields be continuous at the boundary between each pair of adjacent layers. At the boundary between the atmospheric layer and the first layer, the electric field $E_y$ and the magnetic field $H_x$ must be continuous. In addition, at the boundary between adjacent intermediate layers, the electric field $E_y$ and the magnetic field $H_x$ must be continuous. Furthermore, at the boundary between the (L-l)th layer and the substrate layer, the electric field $E_y$ and the magnetic field $H_x$ must also be continuous.

In step 760, matrix equations can be combined to provide a boundary-matched system matrix equation, and as is well understood by those skilled in the art, this boundary-matched system matrix equation may be solved (step 765) (sub-step 816c in the flow chart of FIG. 8) to provide the reflectivity $R_i$ for each harmonic order i. (Alternatively, the partial-solution approach described in "Stable Implementation of the Rigorous Coupled-Wave Analysis for Surface-Relief Dielectric Gratings: Enhanced Transmittance Matrix Approach", E. B. Grann and D. A. Pommet, J Opt. Soc. Am. A, vol. 12, 1077-1086, May 1995, can be applied to calculate either the diffracted reflectivity R or the diffracted transmittance T.)

As shown herein, a planar polarization can be a combination of in-phase TE and TM polarizations. The method of the present invention can be applied to any polarization which is a superposition of TE and TM polarizations by computing the diffraction of the TE and TM components separately and summing them.

In alternate embodiments, the diffracted reflectivity of TM-polarized incident electromagnetic radiation can be calculated using a method (not shown) that parallels procedures described above for the diffracted reflectivity of TE-polarized incident electromagnetic radiation. Referring to FIG. 6, for TM-polarized incident radiation 631 the electric field vector E is in the plane of incidence 640, and the magnetic field vector H is perpendicular to the plane of incidence 640. (The similarity in the TE- and TM-polarization RCWA calculations and the application of the present invention motivates the use of the term 'electromagnetic field' in the present specification to refer generically to either or both the electric field and/or the magnetic field of the electromagnetic radiation.)

Figure 9A:
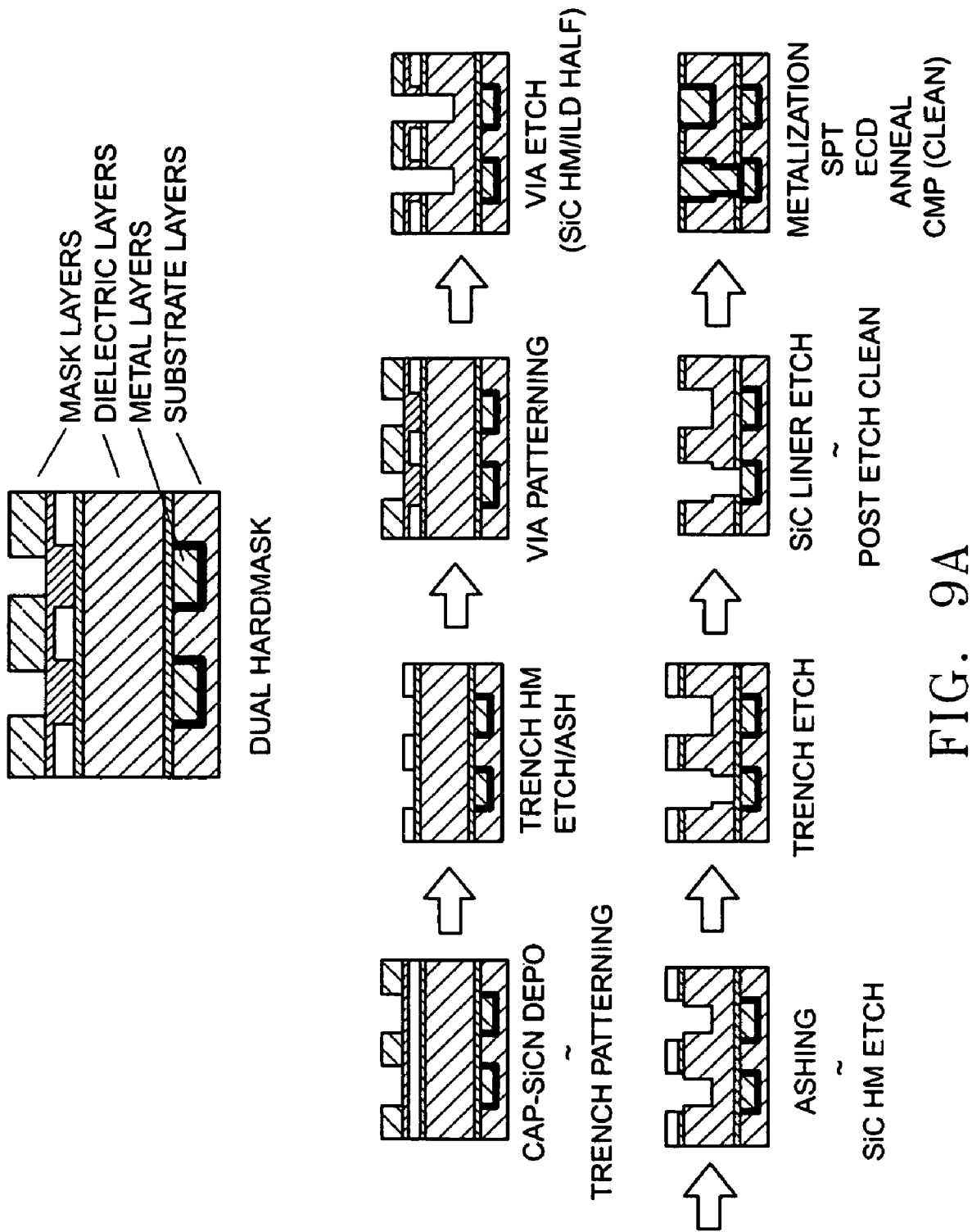
FIGS. 9A-9G illustrate simplified flow diagrams for Dual Damascene procedures in accordance with embodiments of the invention.
Figure 9B:
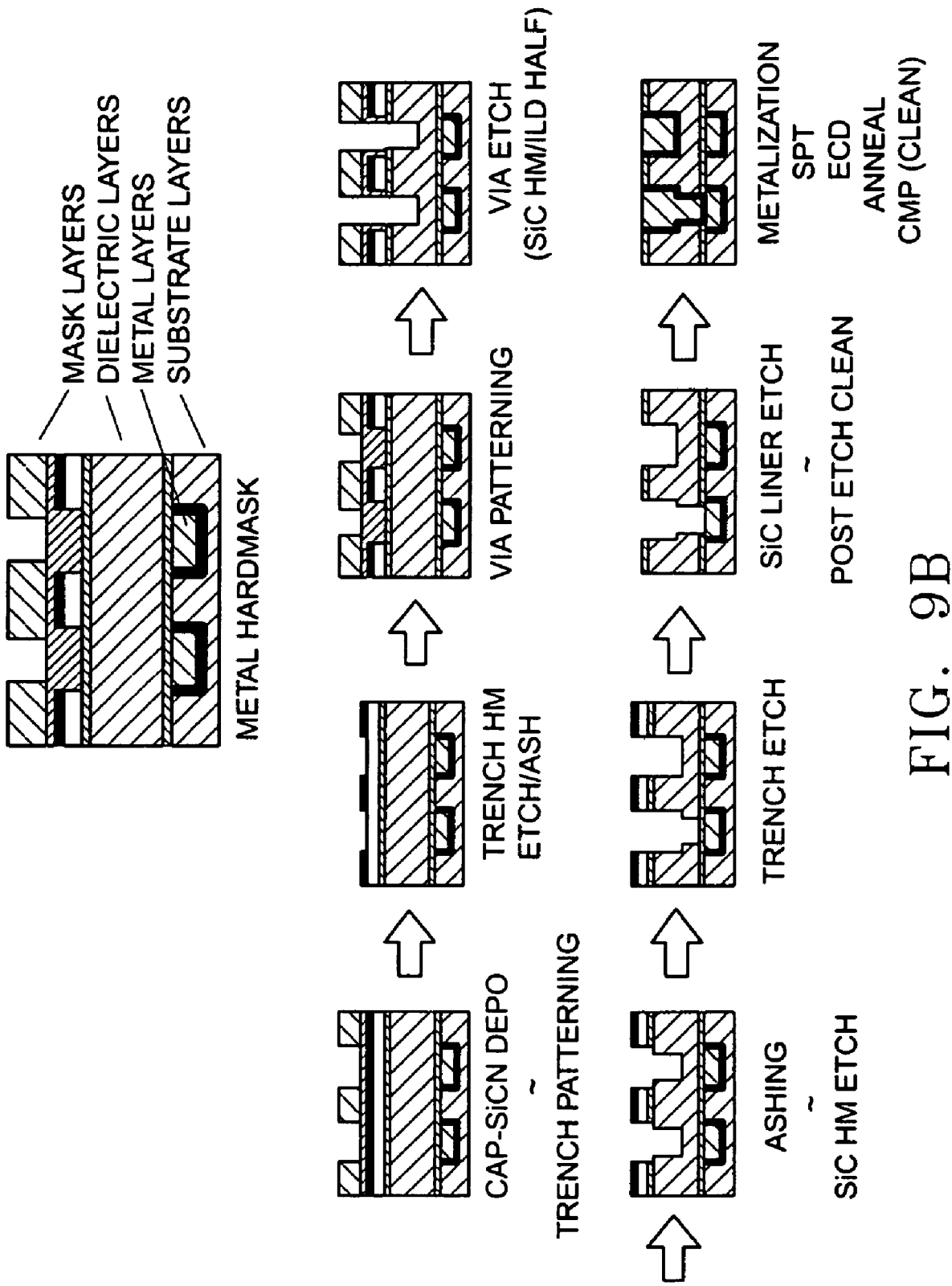
Figure 9C:
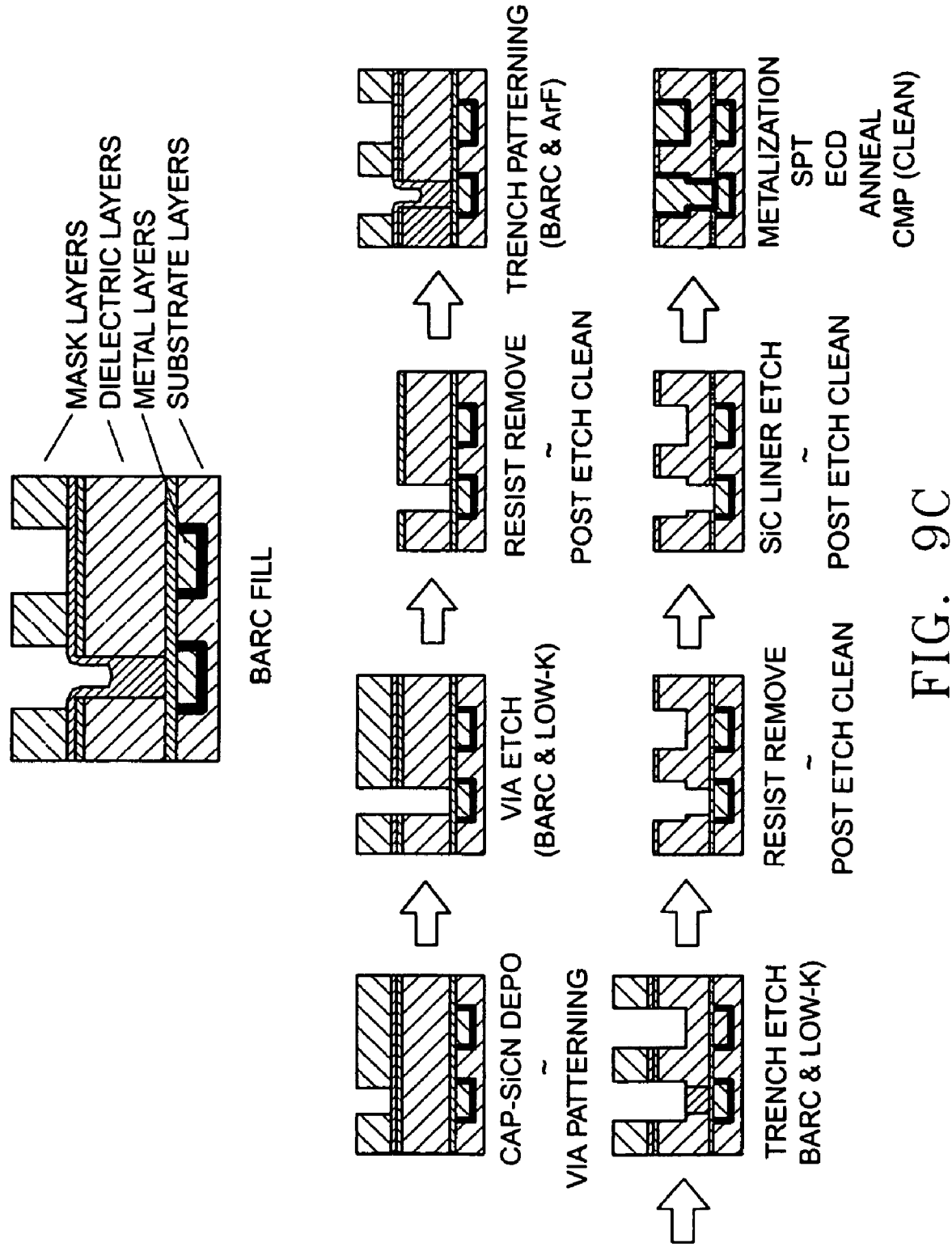
Figure 9D:
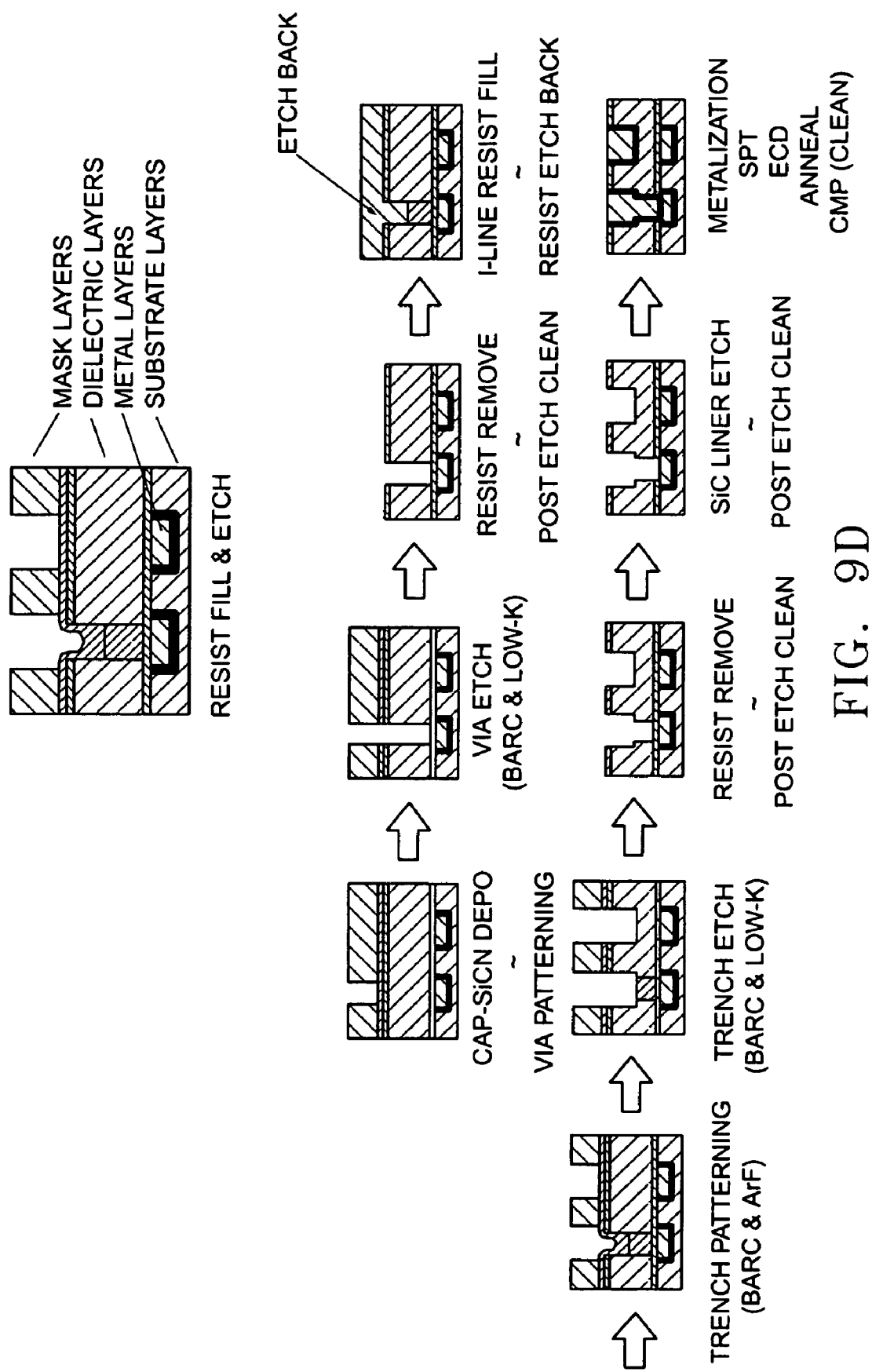
Figure 9E:
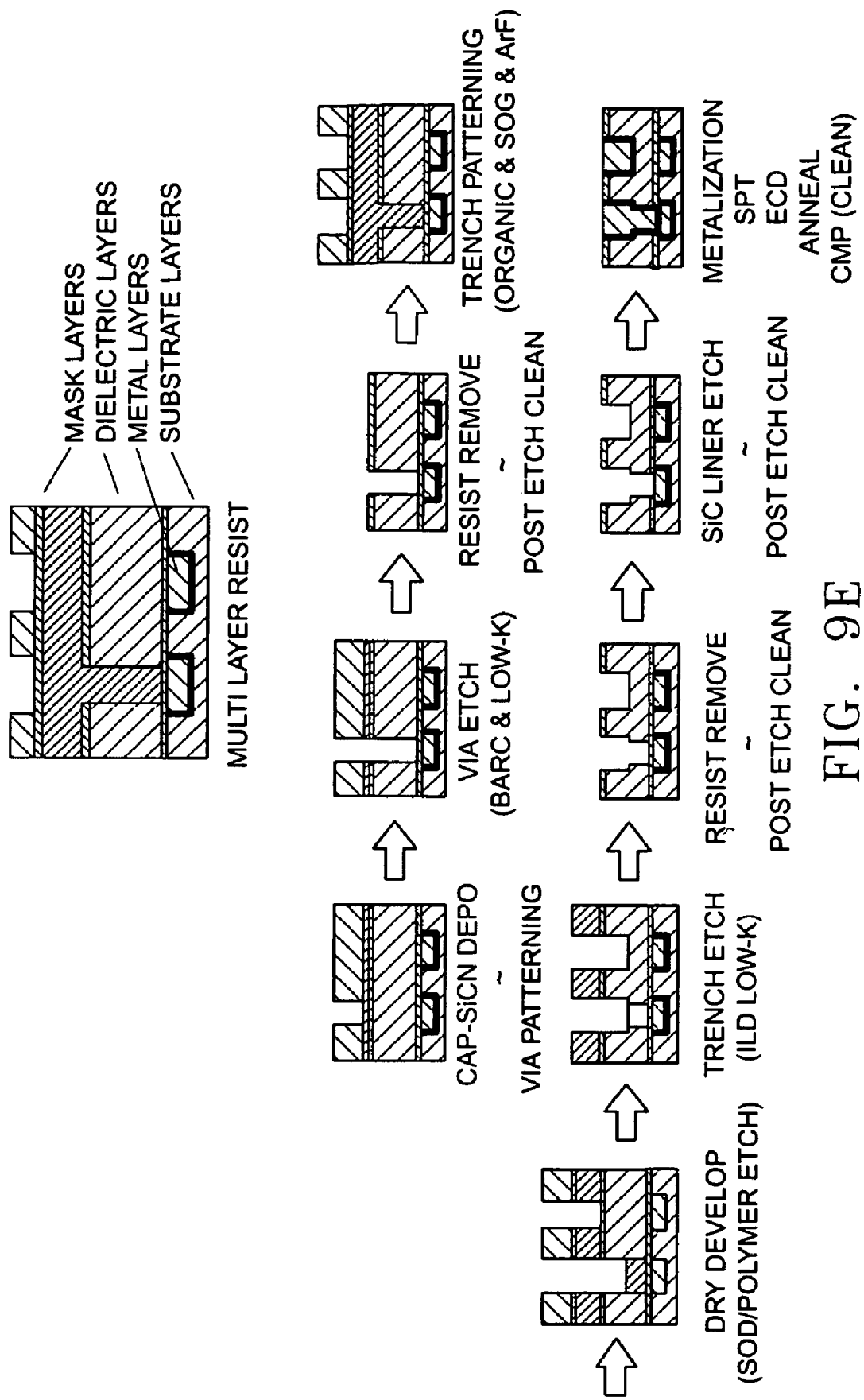
Figure 9F:
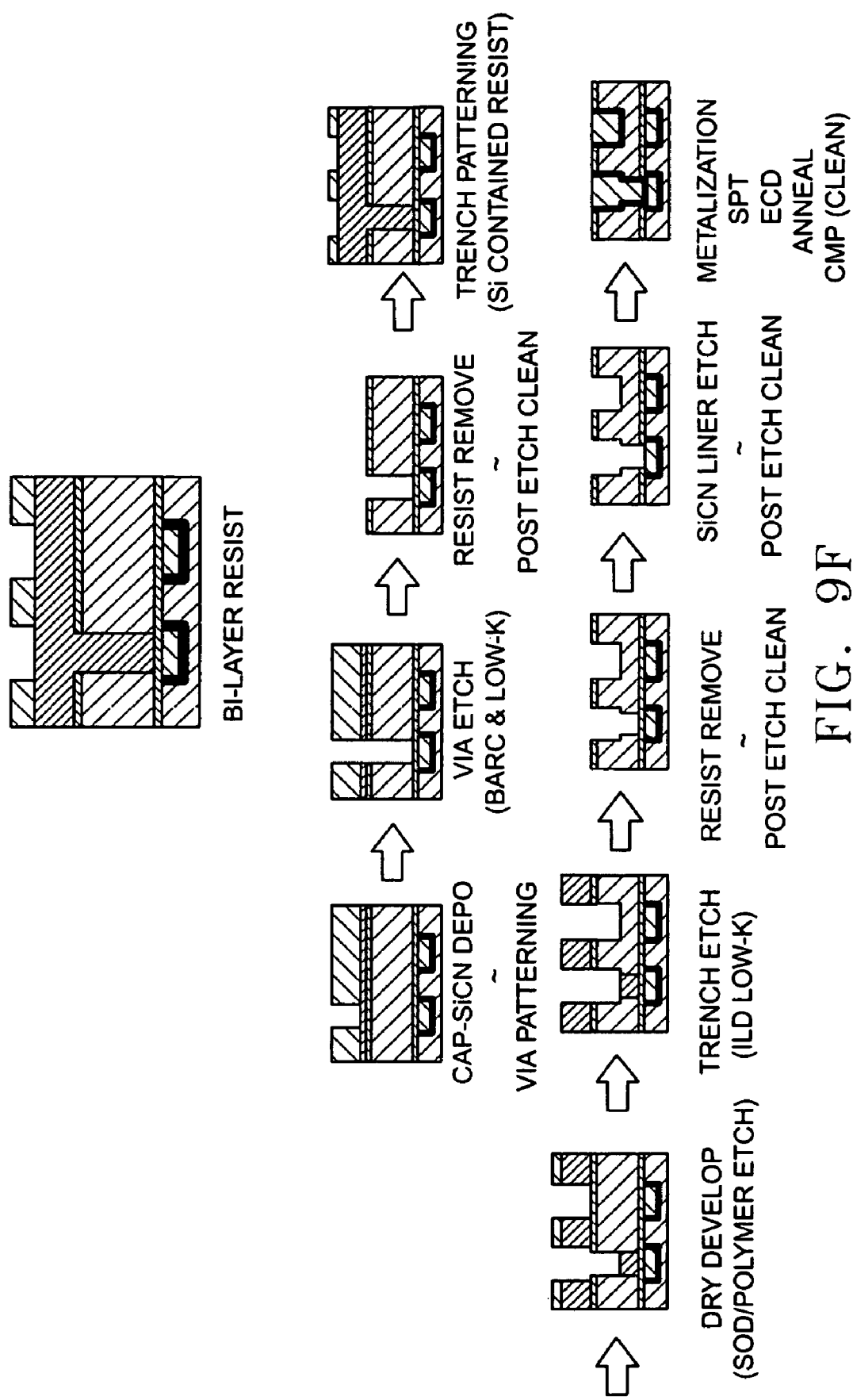
Figure 9G:
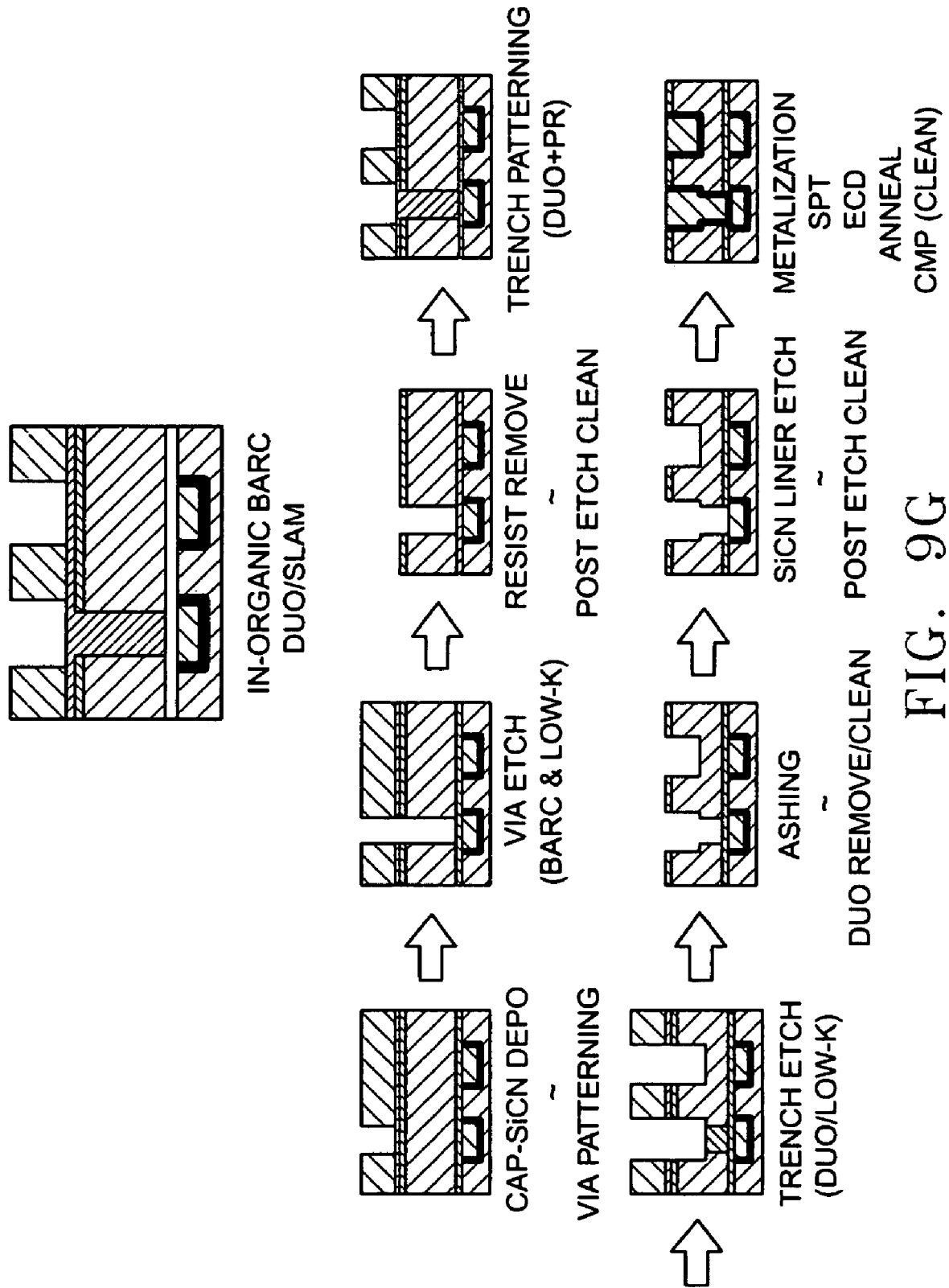

FIGS. 9A-9G illustrate simplified flow diagrams for Dual Damascene procedures in accordance with embodiments of the invention. An exemplary Dual Hardmask procedure is shown in FIG. 9A. An exemplary Metal Hardmask procedure is shown in FIG. 9B. An exemplary BARC Fill procedure is shown in FIG. 9C. An exemplary Resist Fill and Etch procedure is shown in FIG. 9D. An exemplary Multi-Layer Resist procedure is shown in FIG. 9E. An exemplary Bi-Layer Resist procedure is shown in FIG. 9F. An exemplary Inorganic BARC (DUO/SLAM) procedure is shown in FIG. 9G.

In alternate embodiments, a Tunable Etch Resistance ARC (TERA) material may be used as a BARC material and/or an ARC material and/or a hard mask material, and the gate material may include GaAs, SiGe, and strained silicon. The low-k dielectrics can include non-organic material, organic material, combinations thereof. Examples can include HOSP™, NANOGLASS™, organosilicate glass (OSG), CORAL, and Black Diamond.

During Dual Damascene procedures data collection (DC) plans and damage-assessment procedures associated with the control strategies can be executed. Data collection plans and/or damage-assessment procedures can run before, during, and/or after control plans are executed. Data collection plans can obtain data from processing elements such as a tool, a module, a chamber, and a sensor; measuring elements such as a OES system, ODP system, a SEM system, a TEM system, and a MES system.

In addition, the data collection plan selection and initiation can also be context-based. DC plans can be used to provide data for damage-assessment procedures that are associated with a control strategy. The DC plan determines which data is collected, how the data is collected, and where the data is stored. The controller can auto-generate data collection plans and/or damage-assessment procedures for physical modules. One or more data collection plans can be active at a time for a specific module, and the controller can select and use the data collection plan(s) that match the wafer context. Data can include trace data, process log information, recipe data, maintenance counter data, ODP data, OES data, VIP data, or analog data, or a combination of two or more thereof. Measurement devices and/or sensors can be started and stopped by a DC plan. A DC plan can also provide information for trimming data, clipping data, and dealing with spike data and outliers.

In addition, before, during, and/or after data collection, data can be analyzed, and alarm/fault conditions can be identified. The analysis plans associated with an analysis strategy can also be executed. In addition, judgment and/or intervention plans can be executed. For example, after the data has been collected, the data can be sent to a judgment and/or intervention plan for run-rule evaluation. Fault limits can be calculated automatically based on historical data or entered manually based on the customer's experience or process knowledge, or obtained from a host computer. The data can be compared with the warning and control limits, and when a run-rule is violated, an alarm can be generated, indicating the process has exceeded statistical limits.

Furthermore, when an analysis strategy is executed, wafer data, process data, module data, and/or damage-assessment data can be analyzed, and alarm/fault conditions can be identified. In addition, when judgment and/or intervention plans are associated with damage-assessment procedures, they can be executed. For example, after a damage-assessment data has been created, the data can be analyzed using run-rule evaluation techniques. Fault limits can be calculated automatically based on historical data or entered manually based on the customer's experience or process knowledge, or obtained from a host computer. The damage-assessment data can be compared with the warning and control limits, and when a run-rule is violated, an alarm can be generated, indicating the damage has exceeded statistical limits.

When an alarm is generated, the controller can perform either notification or intervention. Notification can be via e-mail or by an e-mail activated pager. In addition, the controller can perform an intervention: either pausing the process at the end of the current lot, or pausing the process at the end of the current wafer. The controller can identify the processing module that caused the alarm to be generated.

Figure 10:
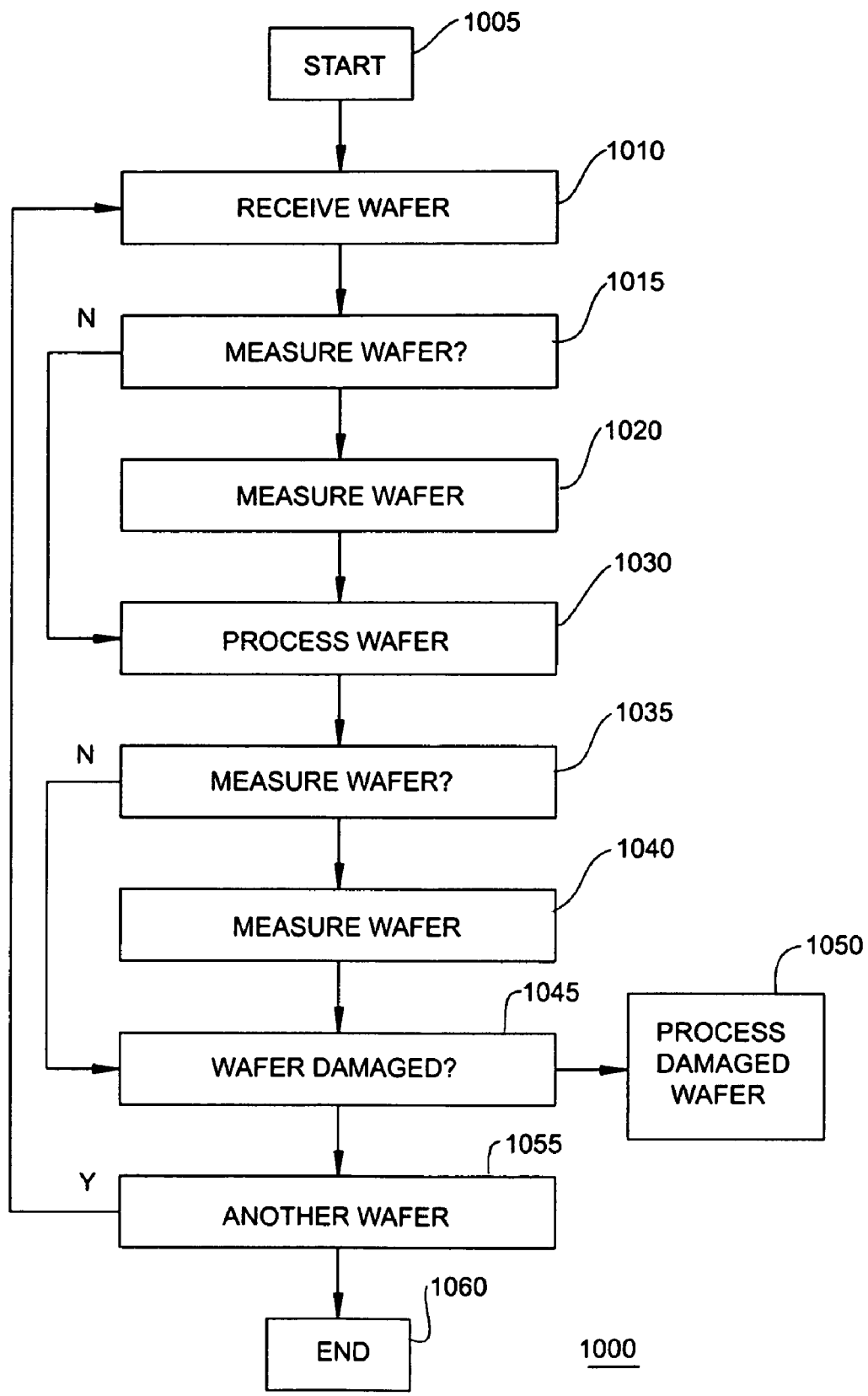
FIG. 10 illustrates an exemplary flow diagram of a method for operating a processing system in accordance with embodiments of the invention.

FIG. 10 illustrates an exemplary flow diagram of a method for operating a processing system in accordance with embodiments of the invention. Procedure 1000 starts at task 1005. In one embodiment, a host system can download recipes and/or variable parameters to a processing tool, such as processing tool 110 (FIG. 1). In addition, a host system can determine wafer sequencing. The downloaded data can include system recipes, process recipes, metrology recipes, and wafer sequencing plans. For example, when all of the recipes that are referenced by the control plans in the matching control strategy have been verified, the controller 120 sends a message to the processing tool 110 indicating that the system recipe verification was successful. If the system recipe is verified, the lot can start with R2R control. If it is not verified, the lot cannot start with R2R control.

In task 1010, when a wafer is received by a processing system 100 (FIG. 1), the pre-process data associated with the wafer and/or lot can be received. Pre-process data can include wafer-related maps, such as damage-assessment maps,. reference map(s), measurement map(s), prediction map(s), and/or confidence map(s), for an in-coming wafer and/or in-coming lot. Pre-process data can include measurement data from a measurement module associated with the processing system, a host system, and/or another processing system.

In task 1015, a query can be performed to determine when to perform a pre-processing measurement and/or damage-assessment process. When the processing sequence is mature, wafer damage should not occur, and the pre-processing measurement and/or damage-assessment process should not be required for all wafers. However, some wafers may be identified as process verification and/or damage-assessment wafers and a pre-processing measurement and/or damage-assessment process can be performed on these wafers. When the process is being developed and/or verified, the process results can be varying, and a pre-processing measurement and/or damage-assessment process can be performed on a larger number of wafers. When pre-processing process is required, procedure 1000 can branch to task 1020, and when a pre-processing process is not required, procedure 1000 can branch to task 1030.

In task 1020, a pre-processing measurement and/or damage-assessment process can be performed. In one embodiment, a control strategy can be executed and used to establish a measurement and/or damage-assessment process plan/recipe. When the wafer is positioned in a metrology tool, the measurements can be made in real-time. When the wafer is not currently positioned in a metrology tool, the wafer can be transferred into the metrology module, and then the measurements can be made in real-time. For example, the wafer can be located in or sent to a metrology tool, such as IMM 140 (FIG. 1).

During a Dual Damascene procedure, a first damascene process can be performed followed by a second damascene process. In some embodiments, a Via First Trench Last (VFTL) procedure can be performed. In other embodiments, a Trench First Via Last (TFVL) procedure can be performed. A pre-processing measurement and/or damage-assessment process can be performed before a first damascene process, a second damascene process, or both damascene processes. Alternatively, a pre-processing measurement and/or damage-assessment process may not be required.

In some embodiments, etched features on a first patterned damascene layer can be measured after a "via first" or a "trench first" etching procedure is performed. One or more data collection (DC) plans and/or mapping applications can be used. Alternatively, a different metrology system can be used.

The number of measurement sites used in a measurement and/or damage-assessment plan can be reduced as the manufacturer becomes more confident that the process is and will continue to produce high quality devices. Alternatively, other pre-processing measurement plans and/or other measurement sites may be used.

A pre-processing measurement and/or damage-assessment plan can be specified by a semiconductor manufacturer based on data stored in a historical database. For example, a semiconductor manufacturer may have historically chosen a number of positions on the wafer when making SEM measurements and would like to correlate the measured data from a integrated metrology tool to the data measured using a SEM tool. Other manufacturers can use TEM and/or FIB data.

When new and/or additional metrology and/or damage-assessment data is required, optical metrology measurements can be made at one or more sites on the wafer. For example, measurement features, such as periodic gratings, periodic arrays, and/or other periodic structures, on a pre-processed wafer can be measured at one or more of the measurement and/or damage-assessment sites. For example, the features on a wafer may be in a layer for a Dual Damascene process as shown in FIGS. 10A-10G.

The pre-processing measurement and/or damage-assessment process can be time consuming and can affect the throughput of a processing system. During process runs, a manufacturer may wish to minimize the amount of time used to measure a wafer. The pre-processing measurement and/or damage-assessment plan can be context driven and different strategies and/or plans may be selected based on the context of the wafer. For example, one or more wafers may not be measured and/or the pre-processing measurement process may be performed using a subset of measurement sites included in the pre-processing measurement plan.

In one embodiment, during a development portion of the semiconductor process, one or more reference maps can be created and stored for later use. The reference maps can include measurement maps, damage-assessment maps, prediction maps, and/or confidence maps.

During pre-processing, one or more prediction maps can be created and/or modified, and the prediction maps can include predicted measured data, predicted damage-assessment data, and/or predicted process data. For example, predicted damage-assessment data can be obtained using a damage-assessment model. Furthermore, one or more confidence maps can be created and/or modified, and the confidence maps can include confidence values for the measured data, confidence values for the damage-assessment data, and/or confidence values for the process data.

In task 1030, the wafer can be processed. For example, a wafer can be process when at least one wafer map or at least one area of a wafer map is within the required limits. During a Dual Damascene procedure, a first damascene process can be performed followed by a second damascene process. In some embodiments, a VFTL procedure can be performed. In other embodiments, a TFVL procedure can be performed. A measurement process can be performed before, during, and/or after a first damascene process or before, during, and/or after a second damascene process, or before, during, and/or after both damascene processes. Alternatively, a measurement process may not be required.

Figure 11A:
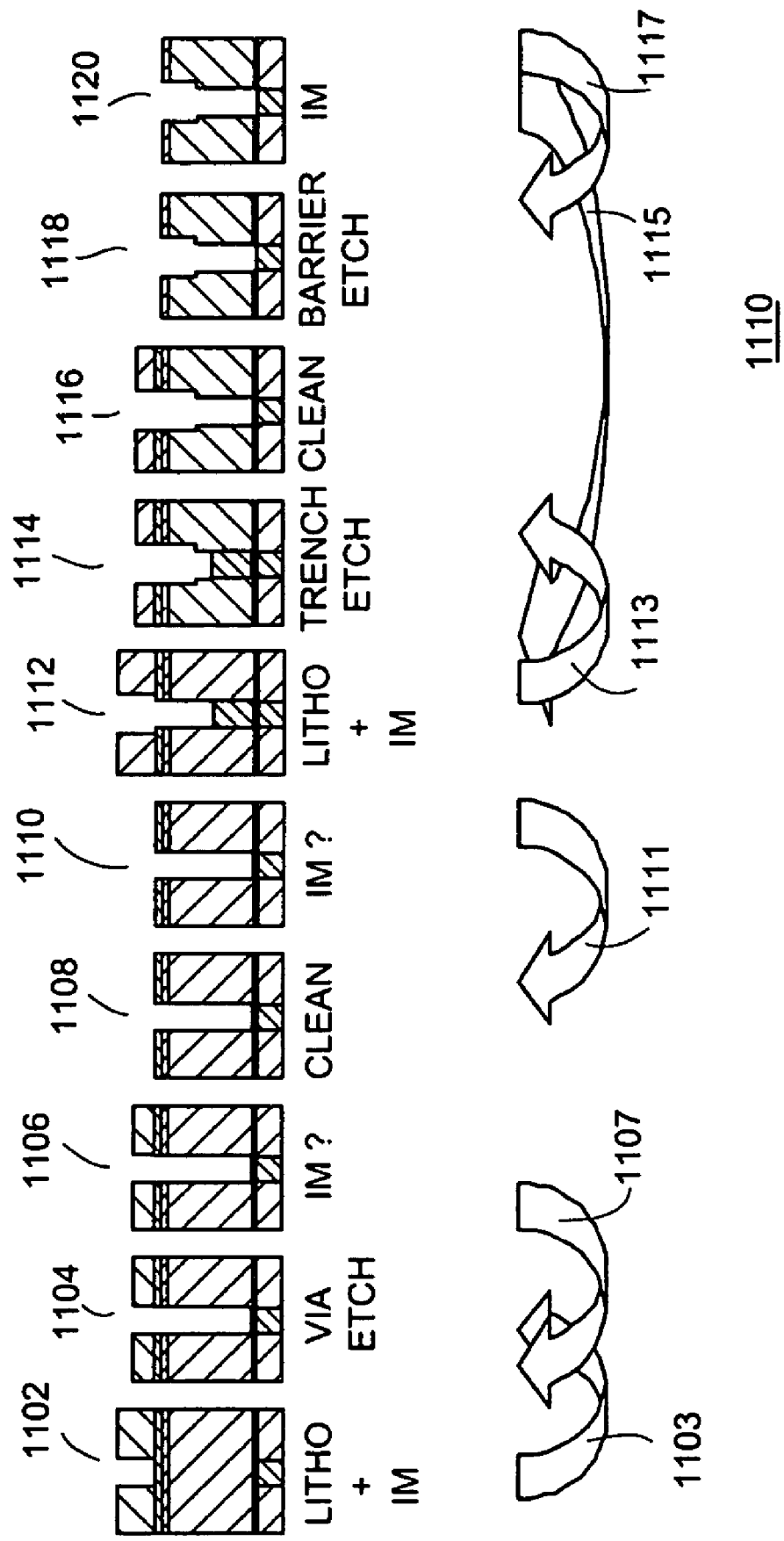
FIG. 11A illustrates a simplified schematic representation of a Via First Trench Last (VFTL) process in accordance with embodiments of the invention.

FIG. 11A illustrates a simplified schematic representation of a VFTL process in accordance with embodiments of the invention. In some cases, the VFTL procedure can include a full via process and a stop layer is not used. Alternatively, a partial via process may be performed and one or more stop layers may be used.

As shown in FIG. 11A, the VFTL procedure 1100 can include a first set of lithography steps 1102, such as deposit, expose, develop, overlay, and measure steps. For example, when the lithography system includes an integrated metrology module, measurements can be performed by the IMM, and optionally measurements may be made using other measurement tools.

Information developed and/or obtained during the lithography steps 1102 can be fed forward 1103 to the etching steps 1104.

The VFTL procedure 1100 can also include etching steps 1104 in which a full or partial via can be etched. Measurement steps 1106 may be used as required during and/or after the via etching steps. Next, cleaning steps 1108 such as ashing and/or wet cleaning steps can be performed to remove process residues from the wafer. Measurement steps 1110 can be used as required after and/or during the cleaning steps.

In addition, the VFTL procedure 1100 can include a second set of lithography steps 1112, such as deposit, expose, develop, overlay, and measure steps. For example, when the lithography system includes an integrated metrology module measurements can be performed by the IMM, and optionally measurements may be made using other measurement tools.

Information developed and/or obtained during the second set of lithography steps 1112 can be fed forward 1113 to the trench etching steps 1112.

VFTL procedure 1100 can also include a second set of etching steps 1112 to etch a full or partial trench. Measurement and/or damage-assessment steps (not shown) can be used as required after and/or during the trench etching steps. Next, cleaning steps 1116 such as ashing and/or wet cleaning steps can be performed to remove process residues from the wafer. Measurement steps (not shown) can be used as required after and/or during the cleaning steps.

Furthermore, the VFTL procedure 1100 can include additional etching steps 1118 such as barrier etching steps and IM measurements 1120 can be made after the additional etching steps have been performed.

Information developed and/or obtained during the IM measurements 1120 can be fed back 1115 to the trench etching steps 1112 and fed back 1119 to the additional etching steps 1118.

Measurement data can be created and/or modified during one or more steps in the VFTL procedure 1100. Measurement maps, damage-assessment maps, prediction maps, reference maps, process maps, confidence maps and/or other maps can be created and/or modified during one or more steps in the VFTL procedure 1100. For example, data and/or maps may be created and/or modified and may be used for damage assessment.

Figure 11B:
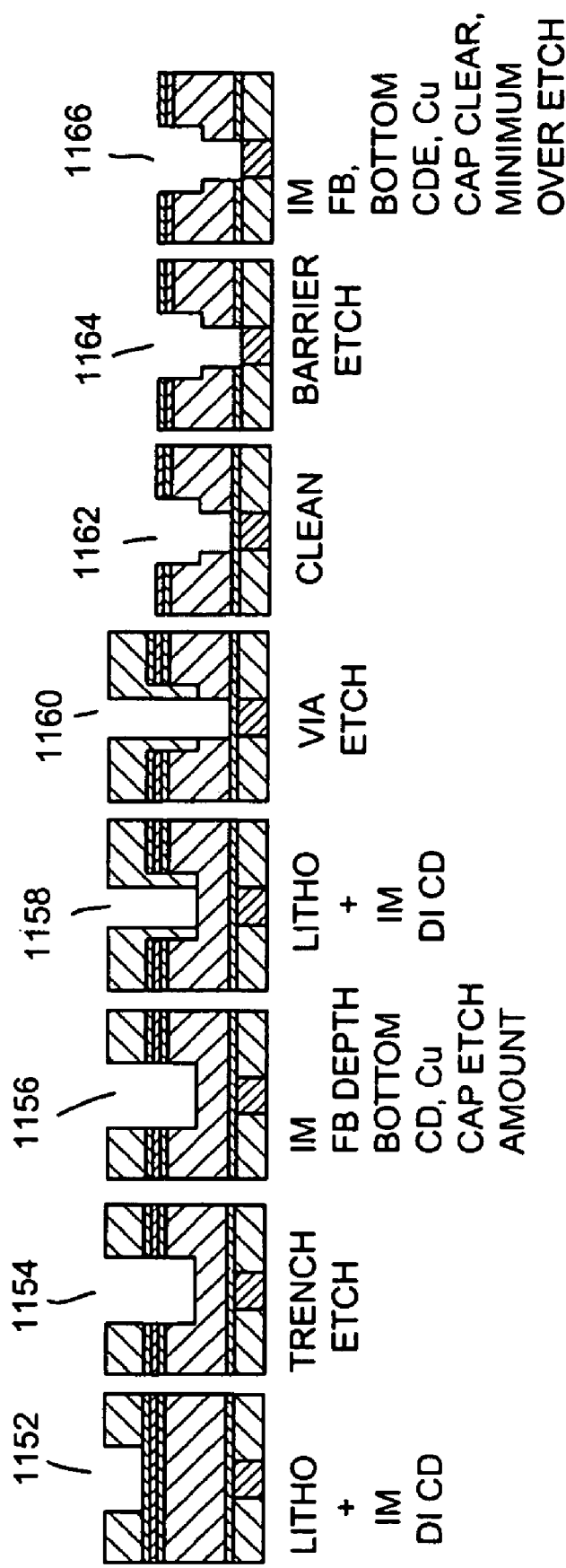
FIG. 11B illustrates a simplified schematic representation of a Trench First Via Last (TFVL) process in accordance with embodiments of the invention.
Figure 11B:
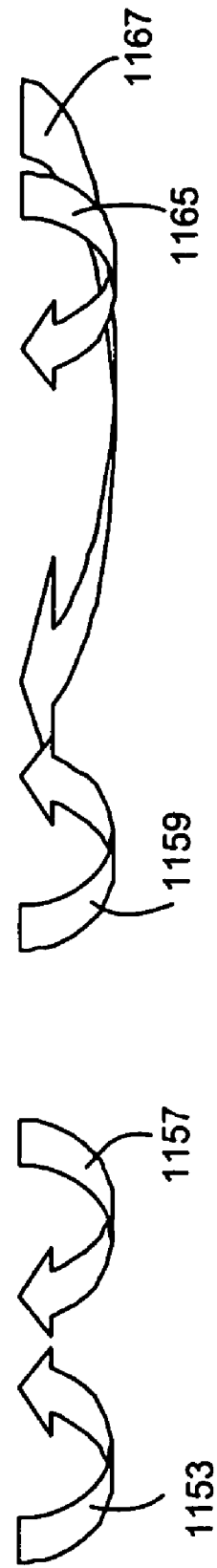

FIG. 11B illustrates a simplified schematic representation of a TFVL process in accordance with embodiments of the invention. In some cases, the TFVL procedure 1150 can include a full trench process and a stop layer is not used. Alternatively, a partial trench process may be performed and one or more stop layers may be used.

The TFVL procedure 1150 can include a first set of lithography steps 1152, such as deposit, expose, develop, overlay, and measure steps. For example, when the lithography system includes an integrated metrology module measurements can be performed by the IMM, and optionally measurements may be made using other measurement tools.

Information developed and/or obtained during the first set of lithography steps 1152 can be fed forward 1153 to the etching steps 1154.

The TFVL procedure 1150 can also include etching steps 1154 to etch a full or partial trench. Measurement and/or damage-assessment steps 1156 can be used as required after and/or during the trench etching steps. Information developed and/or obtained during the etching steps 1154 and/or measurement steps 1156 can be fed back 1157 to the etching steps 1154. Next, cleaning steps (not shown) such as ashing and/or wet cleaning steps can be performed to remove process residues from the wafer. Measurement and/or damage-assessment steps (not shown) can be used as required after and/or during the cleaning steps.

In addition, the TFVL procedure 1150 can include a second set of lithography steps 1158, such as deposit, expose, develop, overlay, and measure steps. For example, when the lithography system includes an integrated metrology module measurements can be performed by the IMM, and optionally measurements may be made using other measurement tools.

Information developed and/or obtained during the second set of lithography steps 1158 can be fed forward 1159 to the via etching steps 1160.

The TFVL procedure 1150 can also include etching steps 1160 to etch a full or partial via after a trench has been etched. Measurement and/or damage-assessment steps (not shown) can be used as required after and/or during the via etching steps. Next, cleaning steps 1162 such as ashing and/or wet cleaning steps can be performed to remove process residues from the wafer. Measurement and/or damage-assessment steps (not shown) can be used as required after and/or during the cleaning steps.

Furthermore, the TFVL procedure 1150 can include additional etching steps 1164 such as barrier etching steps and IM measurements 1166 can be made after the additional etching steps have been performed.

Information developed and/or obtained during the IM measurements 1166 can be fed back 1165 to the via etching steps 1160 and fed back 1165 to the additional etching steps 1164.

New measurement sites can be created and/or used during one or more steps in the TFVL procedure 1150. Measurement maps, damage-assessment maps, prediction maps, reference maps, process maps, confidence maps and/or other maps can be used and/or created during one or more steps in the TFVL procedure 1150. For example, maps may be used to create new measurement sites, and the new measurement sites can be used to create and/or update one or more maps.

Before, during, and/or after a process in a Dual Damascene procedure is perform, one or more process results and/or damage-assessment maps can be created and/or modified. For example, a process results map and/or a damage-assessment can be determined using a measurement map and/or a process map, or a process results map and/or a damage-assessment map may be determined using a process model. A process results and/or a damage-assessment map can illustrate measured, predicted, and/or simulated values.

A process results map for a via etching process can include X and Y dimensions for a via opening, layer information for one or more layers below the via opening, sidewall angle data for the one or more layers, depth information for the via, alignment data, iso/nested data, and a number of modeling shapes used to characterize the shape of the via.

A process results map for a trench etching process can include CD data for the trench width, CD data for the trench depth, layer information for one or more layers above and/or below the trench opening, sidewall angle data for the one or more layers, alignment data, iso/nested data, and a number of modeling shapes used to characterize the shape of the trench.

Tolerance values and/or limits can be associated with the process results and/or damage-assessment maps can be used to identify allowable variations in one or more processes. In addition, process results and/or damage-assessment maps can be used to establish risk factor for one or more processes in a process sequence. For example, process results and/or damage-assessment maps may vary with time and may vary in response to chamber cleaning procedures.

When a wafer is received by the processing system 100, the processing system can receive wafer data that can be used to determine when a damage-assessment process is required. For example, wafer state data may be used. When the process is mature, the process results should be constant and a damage-assessment process should not be required for every wafer. However, some wafers may be identified as process verification wafers and a damage-assessment process can be performed on these wafers. When the process is immature and the process results are varying, a damage-assessment process can be performed.

In various embodiments, a control strategy can be executed and used to establish a damage-assessment measurement recipe for one or more metrology tools. After a Dual Damascene procedure has been performed a wafer can have via features within trench features, isolated and/or nested via features, and isolated and/or nested trench features. For example, the wafer can be sent to an IMM 140 (FIG. 1) where a damage-assessment procedure can be performed using ODP techniques after a Dual Damascene procedure has been performed on the wafer. Alternatively, a different metrology system can be used. For example, FIB, TEM, and/or SEM measurements may be made. In addition, a damage-assessment procedure can include different damage-assessment processes for isolated and nested features.

When the wafer is measured, a damage-assessment plan can be used to determine the number and location of the measurement sites. In addition, one or more data collection plans can be executed, one or more mapping applications can be used, and one or more measurement maps can be created. In addition, stored measurement maps may be used.

In task 1035, a query can be performed to determine when to perform a post-processing measurement and/or damage-assessment process. When the processing sequence is mature, wafer damage should not occur, and the post-processing measurement and/or damage-assessment process should not be required for all wafers. However, some wafers may be identified as process verification and/or damage-assessment wafers and a post-processing measurement and/or damage-assessment process can be performed on these wafers. When the process is being developed and/or verified, the process results can be varying, and a post-processing measurement and/or damage-assessment process can be performed on a larger number of wafers. When post-processing process is required, procedure 1000 can branch to task 1040, and when a post-processing process is not required, procedure 1000 can branch to task 1050.

In task 1040, a post-processing measurement and/or damage-assessment process can be performed. In one embodiment, a control strategy can be executed and used to establish a measurement and/or damage-assessment process plan/recipe. When the wafer is positioned in a metrology tool, the measurements and/or damage-assessments can be made in real-time. When the wafer is not currently positioned in a metrology tool, the wafer can be transferred into the metrology module, and then the measurements and/or damage-assessments can be made at a later time. For example, the wafer can be located in or sent to a metrology tool, such as IMM 140 (FIG. 1).

During a Dual Damascene procedure, a first damascene process can be performed followed by a second damascene process. In some embodiments, a Via First Trench Last (VFTL) procedure can be performed. In other embodiments, a Trench First Via Last (TFVL) procedure can be performed. A post-processing measurement and/or damage-assessment process can be performed before a first damascene process, a second damascene process, or both damascene processes. Alternatively, a post-processing measurement and/or damage-assessment process may not be required.

In some embodiments, etched features on a patterned damascene layer can be measured after a "via last" or a "trench last" etching procedure is performed. One or more data collection (DC) plans and/or mapping applications can be used. Alternatively, a different metrology system can be used.

Figure 12A:
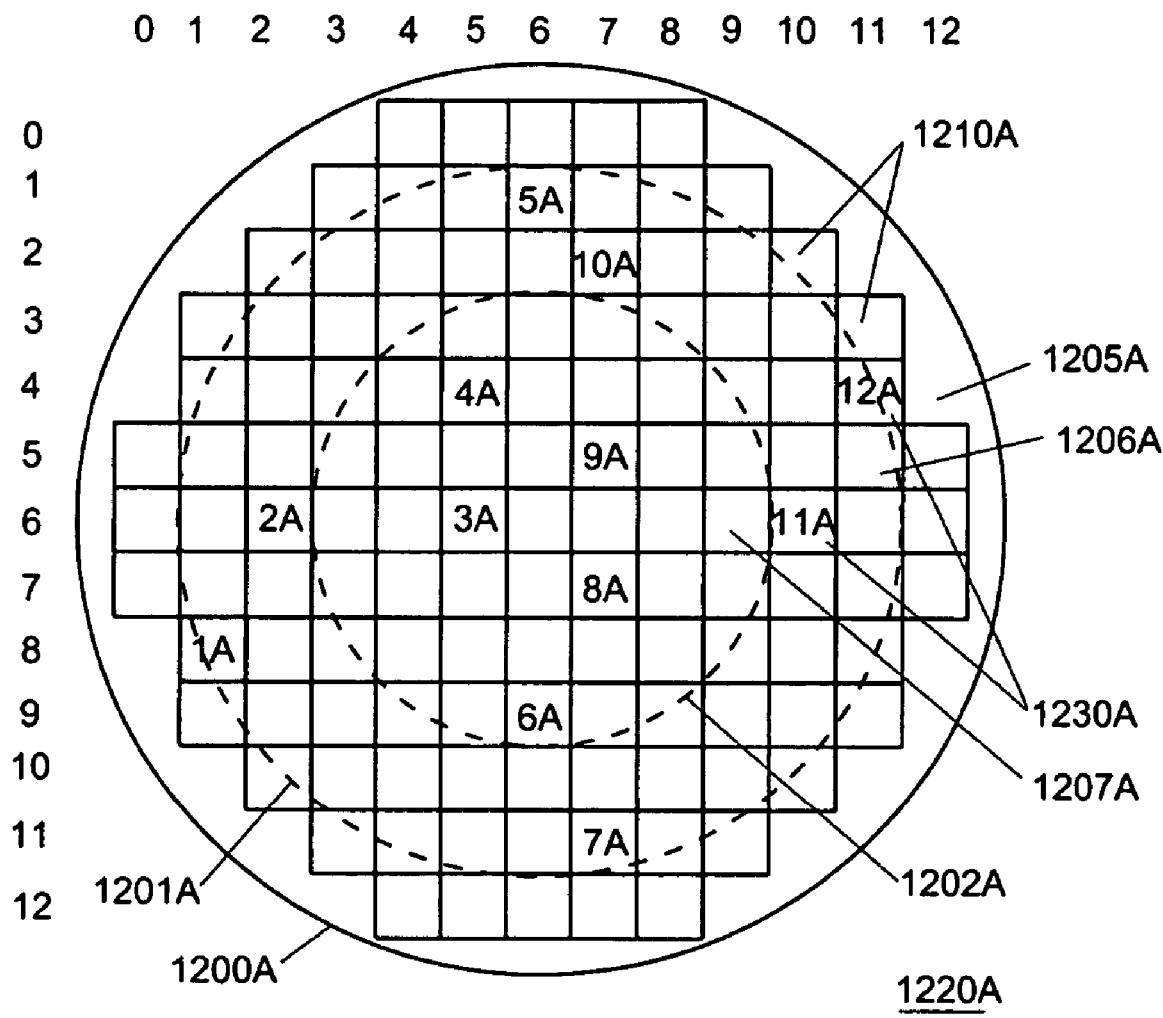
FIGS. 12A-12C show simplified views of wafer maps in accordance with embodiments of the invention.
Figure 12B:
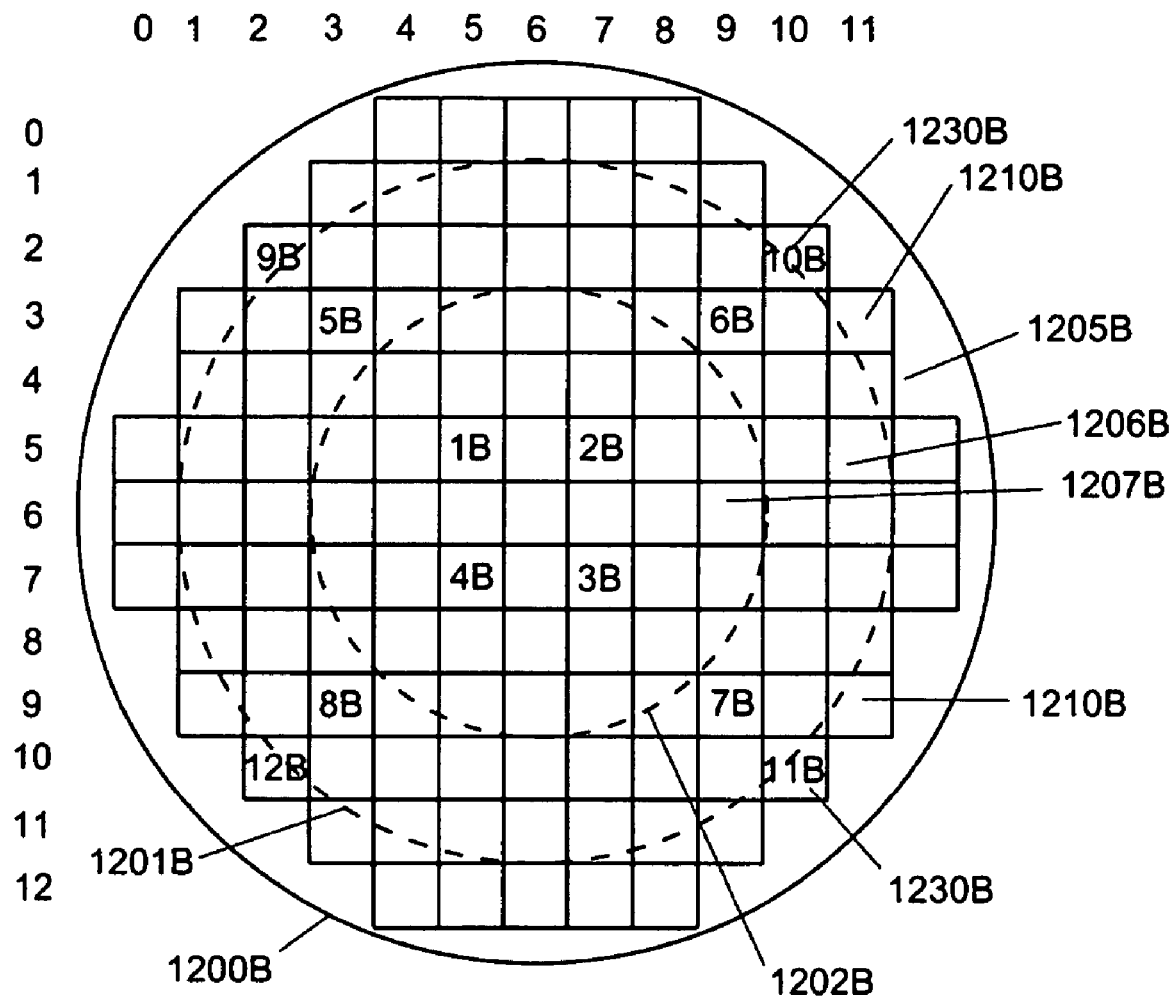
Figure 12C:
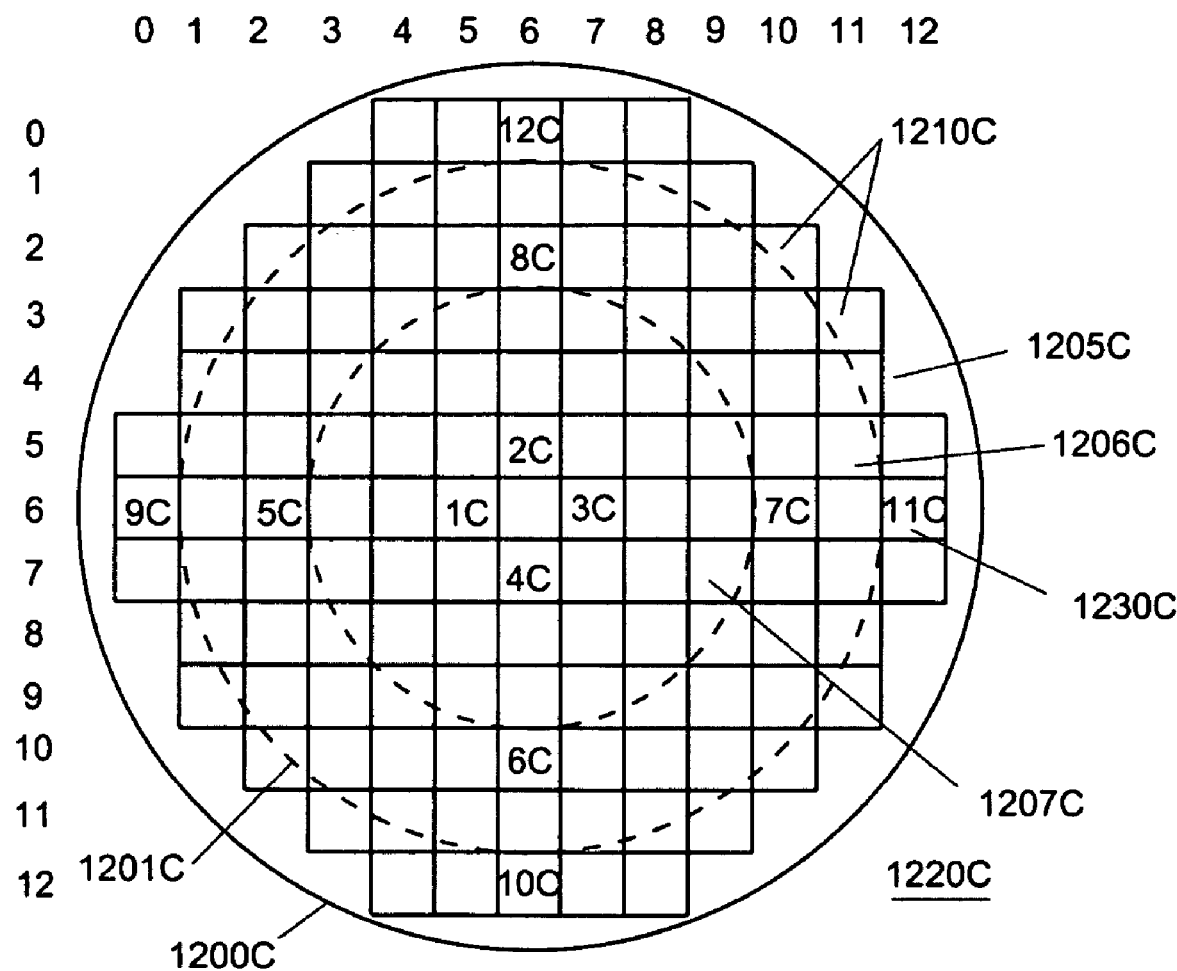

FIGS. 12A-12C show simplified views of wafer maps in accordance with embodiments of the invention. In the illustrated embodiments, post-processing wafer maps are shown having one-hundred twenty-five chip/dies, but this is not required for the invention. Alternatively, a different number of chip/dies may be shown. In addition, the circular shapes shown are for illustration purposes and are not required for the invention. For example, the circular wafer may be replaced by a non-circular substrate, and the chip/dies may have non-circular shapes.

FIG. 12A shows a simplified view of a first post-processing wafer map 1220A on a wafer 1200A that includes a plurality of chip/dies 1210A. Rows and columns are shown that are numbered from zero to twelve for illustration. In addition, twelve chip/dies 1230A are labeled (1A-12A), and these chip/dies can be used to define the location of the measurement sites for the illustrated post-processing measurement and/or damage-assessment plan 1220A. In addition, two circular lines (1201A and 1202A) are shown, and these lines can be used to establish three regions (1205A, 1206A, and 1207A) on the wafer 1200A. Alternatively, a different number of regions having different shapes may be established on wafer map 1220A, and a different number of measurement and/or damage-assessment sites may be established at different locations on the wafer. When a measurement and/or damage-assessment plan is created for a wafer, one or more measurement and/or damage-assessment sites can be established in one or more wafer areas. For example, when the plan is created, measurements and/or damage-assessments do not have to be made at all of the measurement sites 1230A shown in FIG. 12A.

FIG. 12B shows a simplified view of a second post-processing wafer map 1220B on a wafer 1200B that includes a plurality of chip/dies 1210B. Rows and columns are shown that are numbered from zero to twelve for illustration. In addition, twelve chip/dies 1230B are labeled (1B-12B), and these chip/dies can be used to define the location of the measurement sites for the illustrated post-processing measurement and/or damage-assessment plan 1220B. In addition, two circular lines (1201B and 1202B) are shown, and these lines can be used to establish three regions (1205B, 1206B, and 1207B) on the wafer 1200B. Alternatively, a different number of regions having different shapes may be established on the map 1220B, and a different number of sites may be established at different locations on the wafer. When a measurement and/or damage-assessment plan is created for a wafer, one or more measurement and/or damage-assessment sites can be established in one or more wafer areas. For example, when the plan is created, measurements and/or damage-assessments do not have to be made at all of the sites 1230B shown in FIG. 12B.

FIG. 12C shows a simplified view of a third post-processing wafer map 1220C on a wafer 1200C that includes a plurality of chip/dies 1210C. Rows and columns are shown that are numbered from zero to twelve for illustration. In addition, twelve chip/dies 1230C are labeled (1C-12C), and these chip/dies can be used to define the location of the measurement sites for the illustrated post-processing measurement and/or damage-assessment plan 1220C. In addition, two circular lines (1201C and 1202C) are shown, and these lines can be used to establish three regions (1205C, 1206C, and 1207C) on the wafer 1200C. Alternatively, a different number of regions having different shapes may be established on the post-processing measurement and/or damage-assessment map 1220C, and a different number of sites may be established at different locations on the wafer. When a measurement and/or damage-assessment plan is created for a wafer, one or more measurement and/or damage-assessment sites can be established in one or more wafer areas. For example, when the plan is created, measurements and/or damage-assessments do not have to be made at all of the sites 1230C shown in FIG. 12C.

The number of measurement sites used in a measurement and/or damage-assessment plan can be reduced as the manufacturer becomes more confident that the process is and will continue to produce high quality devices. Alternatively, other post-processing measurement plans and/or other measurement sites may be used.

A measurement and/or damage-assessment plan can be specified by a semiconductor manufacturer based on data stored in a historical database. For example, a semiconductor manufacturer may have historically chosen a number of positions on the wafer when making SEM measurements and would like to correlate the measured data from a integrated metrology tool to the data measured using a SEM tool. Other manufacturers can use TEM and/or FIB data.

When new and/or additional metrology and/or damage-assessment data is required, optical metrology measurements can be made at one or more sites on the wafer. For example, measurement features, such as periodic gratings, periodic arrays, and/or other periodic structures, on a post-processed wafer can be measured at one or more of the measurement sites shown in FIGS. 12A-12C. For example, the features on a wafer may be in a layer for a Dual Damascene process as shown in FIGS. 12A-12B.

The post-processing measurement and/or damage-assessment process can be time consuming and can affect the throughput of a processing system. During process runs, a manufacturer may wish to minimize the amount of time used to measure a wafer. The post-processing measurement and/or damage-assessment plan can be context driven and different strategies and/or plans may be selected based on the context of the wafer. For example, one or more wafers may not be measured and/or the post-processing measurement process may be performed using a subset of measurement sites included in the post-processing measurement plan.

During a development portion of the semiconductor process, one or more reference maps can be created and stored for later use. A reference measurement map can include measured data at measurement sites that are different from those shown in FIGS. 12A-12C. A reference damage-assessment map can include damage-assessment data at measurement sites that are different from those shown in FIGS. 12A-12C. Alternatively, a reference map can use the same set of measurement sites or a reference measurement map may not be required.

Before, during, and/or after processing, one or more prediction maps can be created and/or modified, and the prediction maps can include predicted measured data, predicted damage-assessment data, and/or predicted process data. For example, predicted damage-assessment data can be obtained using a damage-assessment model.

In addition, before, during, and/or after processing one or more confidence maps can be created and/or modified, and the confidence maps can include confidence values for the measured data, confidence values for the damage-assessment data, and/or confidence values for the process data.

The wafer maps can include one or more Goodness Of Fit (GOF) maps, one or more grating thickness maps, one or more via-related maps, one or more Critical Dimension (CD) maps, one or more CD profile maps, one or more material related maps, one or more trench-related maps, one or more sidewall angle maps, one or more differential width maps, or a combination thereof. The post-process data can also include site result data, site number data, CD measurement flag data, number of measurement sites data, coordinate X data, and coordinate Y data, among others.

In some embodiments, curve-fitting procedures can be performed to calculate data for the sites on the wafer that are not measured. Alternatively, the wafer maps may be determined using surface estimating, surface fitting techniques, or other mathematical techniques. When maps are created for a wafer, one or more measurement sites can be established in one or more wafer areas, and these measurement sites can be used to provide areas where the data can be more accurate. For example, when the maps are created, measurements do not have to be made at all of the measurement sites.

Some errors that are generated by mapping applications can be sent to the FDC system, and the FDC system can decide how the processing system should respond to the error. Other errors can be resolved by the mapping applications.

When wafer maps are created and/or modified, values may not be calculated and/or required for the entire wafer, and a wafer map may include data for one or more chip/dies, one or more different areas, and/or one or more differently shaped areas. For example, a processing chamber may have unique characteristics that may affect the damage levels in certain areas of the wafer. In addition, a manufacturer may allow wider limits for chips/dies in one or more regions of the wafer to maximize yield. A mapping application and/or the FDC system can use business rules to determine uniformity and/or damage-assessment limits.

When a value in a map, such as damage-assessment map, is close to a limit, the confidence value may be lower than when the value in a map is not close to a limit. In addition, the damage-assessment values can be weighted for different chips/dies and/or different areas of the wafer. For example, a higher confidence weight can be assigned to the calculations and/or data associated with one or more of the previously discussed measurement sites.

In addition, process result, measurement, damage-assessment, and/or prediction maps associated with one or more processes may be used to calculate a confidence map for a wafer. For example, values from another map may be used as weighting factors.

Data from damage-assessment procedures can be used to change a measurement and/or damage-assessment plan and to determine when to establish a new measurement and/or damage-assessment site. In addition, when the confidence values are low in one or more areas of the wafer, or when an error has occurred, one or more new measurement sites can be established. Furthermore, when the values on a confidence map are consistently high for a particular process and/or when damage-assessment values are consistently within acceptable limits for a particular process, a new measurement plan may be establish that uses a smaller number of measurement sites and that decreases the throughput time for each wafer.

When a processing sequence is being developed and/or modified, new measurement sites can be established for the entire wafer, or for a particular area, such as a quadrant (Q1, Q2, Q3, or Q4), or in a particular direction, such as a radial direction. For example, in some processing chambers, process results may be measured, modeled, and/or modified more easily in a radial direction.

A damage-assessment plan can be specified by a semiconductor manufacturer based on data stored in a historical database. For example, a semiconductor manufacturer may have historically chosen a number of positions on the wafer when making CDSEM measurements and would like to correlate the measured data from a integrated metrology tool to the data measured using a CDSEM tool. Other manufacturers can use TEM and/or FIB data.

When new and/or additional damage-assessment metrology data is required, optical metrology measurements can be made at one or more sites on the wafer. For example, measurement features on a wafer can be measured at one or more of the measurement sites during a damage-assessment procedure. The damage-assessment process can be time consuming and can affect the throughput of a processing system. During process runs, a manufacturer may wish to minimize the amount of time used to measure a wafer. The damage-assessment plan can be context driven and different strategies and/or plans may be selected based on the context of the wafer. For example, one or more wafers may not be measured and/or the damage-assessment process may be performed using a subset of measurement sites included in the damage-assessment plan.

In some cases, data for an entire wafer can be calculated during a damage-assessment procedure. Alternatively, data may be calculated and/or predicted for a portion of the wafer. For example, a portion may include one or more radial areas and/or quadrants. An error condition can be declared when damage-assessment data cannot be determined. In addition, an error condition can be declared when one or more of the measured values and/or calculated/predicted values are outside a damage limit established for the wafer. Some errors that are generated during a damage-assessment procedure can be sent to the FDC system, and the FDC system can decide how the processing system should respond to the error. Other errors can be resolved by the measurement and/or processing tools.

During a damage-assessment procedure, one or more post-processing measurement, prediction, and/or confidence maps can be calculated and/or modified. The maps can include one or more areas of a wafer. In addition, a manufacturer may allow wider limits (more damage) for chips/dies in one or more regions of the wafer to maximize yield. A damage-assessment application and/or the FDC system can use business rules to determine acceptable limits for damaged dielectric.

Before, during, and/or after processing, different types of confidence maps can be created and/or modified. A first kind of confidence map can provide an estimate of the confidence in the measured data. Since it would take too long to measure the entire wafer, a smaller number of measurement sites is being used and confidence factors must be establish to ensure that the predicted measured data accurately represents the data that would be obtained if more sites or a larger portion of the wafer were used to make the measurements.

A second kind of confidence map can provide an estimate of the confidence in one or more processes performed during a Dual Damascene procedure. Since it would take too long to measure the entire wafer after it has been processed and a semiconductor manufacturer would like to be sure that the one or more processes performed during a Dual Damascene procedure have been performed correctly, the actual measured data and/or the predicted measured data can be compared to the expected values and when these numbers are with specified limits, the semiconductor manufacturer can assume that the Dual Damascene procedure was performed correctly even though the entire wafer has not been measured.

A third kind of confidence map can provide an estimate of the confidence that the one or more processes performed during a Dual Damascene procedure have not damage the wafer. Since it would take too long to measure the entire wafer after it has been processed and a semiconductor manufacturer would like to be sure that the one or more processes performed during a Dual Damascene procedure have not damaged the wafer, the actual measured damage-assessment data and/or the predicted damage-assessment data can be compared to the expected values and when these numbers are with specified limits, the semiconductor manufacturer can assume that the wafer was not damaged during the Dual Damascene procedure even though a damage-assessment procedure was not performed on the entire wafer.

In task 1045, a query can be performed to determine when the wafer has one or more damaged areas. When one or more damaged areas are present, procedure 1000 can branch to task 1070, and when one or more damaged areas are not present, procedure 1000 can branch to task 1080.

In task 1050, a damaged wafer can be processed. For example, when a damaged wafer is identified during normal processing the wafer can be transferred to a first location, which may be a holding location. When the damage-assessment procedure does not identify a damaged wafer, then wafer processing can continue.

When a damaged wafer is identified, one or more wafer maps can be examined. A damage-assessment map can be examined to determine the amount of damage present on the wafer.

In one embodiment, when a damage-assessment is made at one assessment site, and the data at that site suggests that the wafer is damaged. Then, the damage-assessment process can be repeated at additional assessment sites. When the damage-assessment data at one or more of the additional assessment sites indicates a damaged wafer, then the wafer can be removed from the processing sequence, and additional measurements can be performed.

When the damage-assessment data at one or more of the additional assessment sites indicates an undamaged wafer, then the wafer can be re-measured using the first assessment site. When the re-measured assessment data again indicates that the wafer is damaged, the wafer can be removed from the processing sequence, and additional measurements and/or analysis can be performed. In addition, an error condition can be established, and a person responsible for the tool and/or process can be notified when a damaged wafer is detected.

In some embodiments, a damaged wafer can be treated in order to heal, seal, and/or clean the wafer. Techniques for treating damaged wafers are taught in co-pending U.S. patent application Ser. No. 10/682,196, entitled METHOD AND SYSTEM FOR TREATING A DIELECTRIC FILM, by Toma, et al., filed on Oct. 10, 2003, and batch techniques for treating damaged wafers are taught in U.S. patent application Ser. No. 11/239,294, entitled TREATMENT OF LOW DIELECTRIC CONSTANT FILMS USING A BATCH PROCESSING SYSTEM, by Toma et al. filed on Sep. 29, 2005, both of which are incorporated by reference herein in their entirety.

In other embodiments, damaged wafers can be treated using supercritical processes and techniques for treating wafers using supercritical processes are taught in co-pending U.S. patent application Ser. No. 10/379,984, entitled METHOD OF PASSIVATING OF LOW-K DIELECTRIC MATERIALS IN WAFER PROCESSING, by Toma, et al., filed on Mar. 4, 2003, and additional techniques for treating damaged wafers are taught in U.S. patent application Ser. No. 11/060,352, entitled METHOD AND SYSTEM FOR TREATING A DIELECTRIC FILM, by Kevwitch et al. filed on Feb. 18, 2005, both of which are incorporated by reference herein in their entirety.

Additional damage-assessment procedures can be performed on some wafers after these wafers have been treated in order to verify that the damaged areas of the wafer have been treated properly.

In some embodiments, wafers can be treated using the techniques described above before they are subject to a damage-assessment procedure.

Libraries can be expanded to include profiles and simulated results for "repaired" measurement structures. When a library is created, one or more library creation criteria can be used to determine the size and/or structure of the library. For example, the library creation criteria can include size data, resolution data, process data, fabrication data, and/or structure data.

During a library development process, one or more wafers can be subject to processing conditions that are designed to create one or more damaged areas as shown in FIGS. 4A and 5A, and damage-assessment procedures can be performed to measure the damaged structures and characterize the expected optical response. Additional measurements can then be made using other measurement tools to verify the results obtained during the damage-assessment procedures. Furthermore, electrical tests can be performed later in the processing sequence, and this data can be used to verify the dielectric properties of undamaged and/or damaged structures.

In addition, a wafer that has damaged areas can be cleaned to remove the damaged material. Measurements can then be made to obtain a more accurate measurement of the undamaged portion of a structure since a less complicated diffraction signal can be obtained when the damaged material is removed.

When damage-assessment libraries are being created, the damage-assessment measurement site can be selected from a set of previously defined sites. For example, during an installation procedure for a metrology tool, measurements may have been made at more than forty sites, and one or more of these sites can be used. Alternatively, a damage-assessment measurement site may not be selected from a set of previously defined sites.

When a new damage-assessment measurement site is required, a new control strategy including a new damage-assessment metrology recipe can be created, and the new recipe can be used to instruct the metrology tool to make additional damage-assessment measurements at the one or more new sites.

In task 1080, a query can be performed to determine when an additional wafer requires processing. When a process is performed, a number of wafers can be processed as a lot or a batch. When additional wafer processing is not required, procedure 1000 can branch to task 1060, and when an additional wafer requires processing, procedure 1000 can branch to task 1010.

Procedure 1000 can end in 1060.

Referring back to FIG. 1, the controller 120 can use the difference between the measurement maps for the incoming material (input state) and process results maps (desired state) to predict, select, or calculate a set of process parameters to achieve the desired result of changing the state of the wafer from the input state to the desired state. For example, this predicted set of process parameters can be a first estimate of a recipe to use to provide a uniform process that does not damage the dielectric material of the wafer. In addition, damage-assessment data, measurement maps, and/or process results maps can be obtained from the MES 130 and can be used to update the first estimate.

Damage-assessment procedures can be updated using feedback data that can be generated by running monitor, test, and/or production wafers, varying the process settings and observing the results, then updating one or more different applications. For example, a damage-assessment update can take place every N processing hours by measuring the before and after characteristics of a monitor wafer. By changing the settings over time to check different operating regions, the complete operating space can be validated over time, or run several monitor wafers at once with different recipe settings. The damage-assessment update can take place within the controller 120, at the processing tool, or at the factory, allowing the factory to control and/or manage the monitor wafers and damage-assessment updates.

The controller 120 can update damage-assessment procedures at one or more points in a processing sequence. In one case, the controller 120 can use the feed-forward information, modeling information, and the feedback information to determine whether or not to change one or more of the currently used damage-assessment procedures before running the current wafer, before running the next wafer, or before running the next lot.

In another aspect of the invention, one or more controllers can be use to perform a regression optimization procedure. For example, a controller can receive a set of measurements and selects values for parameters, parameter ranges, and parameter resolutions. A controller may run the regression optimization, generate regression results, analyze the generated regression results, and use the generated regression results to adjust parameters, ranges, and/or resolutions. In addition, the results can be used to create libraries of damaged periodic structures, and to identify damaged periodic structures.

When damage-assessment procedures are being performed, the data sources and/or libraries may be important and may be identified in advance. For example, damage-assessment procedures may be either externally generated or internally generated. The externally generated damage-assessment procedures and/or libraries may be provided by the MES 130. The internally generated damage-assessment procedures can be obtained from a database and/or created using inputs from a GUI. In addition, business rules can be provided that can be used to determine when to use an externally generated or an internally generated procedure and//or libraries. Damage-assessment procedures and/or libraries must be evaluated and pre-qualified before they can be used. For example, the database and library may be stored in a computer-readable medium or a memory associated with a computer. Furthermore, a controller may also optionally cluster the library, as described in U.S. patent application Ser. No. 09/727,531, entitled CLUSTERING FOR DATA COMPRESSION, filed Jul. 28, 2000, which is incorporated by reference in its entirety.

Although only certain embodiments of this invention have been described in detail above, those skilled in the art will readily appreciate that many modifications are possible in the embodiments without materially departing from the novel teachings and advantages of this invention. Accordingly, all such modifications are intended to be included within the scope of this invention.

Thus, the description is not intended to limit the invention and the configuration, operation, and behavior of the present invention has been described with the understanding that modifications and variations of the embodiments are possible, given the level of detail present herein. Accordingly, the preceding detailed description is not mean or intended to, in any way, limit the invention—rather the scope of the invention is defined by the appended claims.

What is claimed is:

1. A method of measuring a damaged structure formed on a semiconductor wafer using optical metrology, the method comprising:

directing an incident beam on the damaged structure;

receiving a diffracted beam from the damaged structure;

processing the received diffracted beam to determine a profile of an undamaged portion of the damaged structure and to measure an amount of dielectric damage of the damaged structure, wherein processing the received diffracted beam comprises:

obtaining a measured diffraction signal based on the received diffracted beam; obtaining a first simulated diffraction signal, wherein the first simulated diffraction signal was generated using a hypothetical profile of the damaged structure, wherein the hypothetical profile is divided into multiple effective medium layers, and wherein each effective medium layer includes an undamaged dielectric portion and a damaged dielectric portion;

comparing the measured diffraction signal to the first simulated diffraction signal; and when the measured diffraction signal and the first simulated diffraction signal match within a matching criterion, determining a damage amount for the damaged structure based on the damaged portions of the effective medium layers of the hypothetical profile that corresponds to the first simulated diffraction signal, wherein the undamaged dielectric portion is associated with a refraction index of one dielectric material, and wherein the damaged dielectric portion is associated with an effective refraction index, which is a weighted average of refraction indices of at least two materials.

2. The method of claim 1, wherein receiving a diffracted beam comprises:
receiving an angular distribution of diffracted beams, wherein the amount of dielectric damage of the damaged structure is measured based on the angular distribution of diffracted beams, and wherein the profile of the undamaged portion of the damaged structure is determined based on one of the diffracted beams in the angular distribution of diffracted beams.

3. The method of claim 2, wherein the angular distribution of diffracted beams is received using an array of detectors, and wherein the diffracted beam processed to determine the profile of the undamaged portion of the damaged structure is received using one of the detectors in the array of detectors.

4. The method of claim 3, wherein receiving an angular distribution of diffracted beams comprises:
receiving a first angular distribution of diffracted beams using a first array of detectors in a first dimension; and
receiving a second angular distribution of diffracted beams using a second array of detectors in a second dimension.

5. The method of claim 2, wherein the angular distribution of diffracted beams is received by translating the detector across a range of angles, and wherein the diffracted beam processed to determine the profile of the undamaged portion of the damaged structure is received by translating the detector to one of the angles in the range of angles.

6. The method of claim 5, wherein receiving an angular distribution of diffracted beams comprises:
receiving a first angular distribution of diffracted beams by translating the detector across a range of angles in a first dimension; and
receiving a second angular distribution of diffracted beams by translating the detector across a range of angles in a second dimension.

7. The method of claim 1, wherein receiving a diffracted beam comprises:
receiving an angular distribution of diffracted beams using a lens;
integrating the angular distribution of diffracted beams using the lens; and directing the integrated angular distribution of diffracted beams to a first detector, wherein the amount of dielectric damage of the damaged structure is measured based on the integrated angular distribution of diffracted beams; and
receiving a diffracted beam using a second detector, wherein the profile of the undamaged portion of the damaged structure is determined based on the diffracted beam received using the second detector.

8. The method of claim 7, wherein receiving an angular distribution of diffracted beams comprises:
receiving a first angular distribution of diffracted beams in a first dimension; and
receiving a second angular distribution of diffracted beams in a second dimension.

9. The method as claimed in claim 1, wherein the damaged structure includes, a trench with top edge damage, a trench with bottom corner damage, a trench with bottom surface damage, a trench with sidewall damage, a trench with sidewall angle damage, a via with top edge damage, a via with bottom corner damage, a via with bottom surface damage, a via with sidewall damage, a via with sidewall angle damage, or a feature with top surface damage, or combinations of two or more thereof.

10. The method of claim 1, wherein the weighted average comprises a volume-based average, a surface area-based average, a process-based average, a length-based average, or a depth-based average or a combination of two or more thereof.

11. The method of claim 1, wherein damaged dielectric portion comprises a damaged low-k dielectric, or a damaged ultra-low-k dielectric, or a combination thereof.

12. The method of claim 1 further comprising: when the measured diffraction signal and the first simulated diffraction signal do not match within a matching criterion, obtaining a different simulated diffraction signal to compare with the measured diffraction signal, wherein the different simulated diffraction signal was generated using a different hypothetical profile having at least one effective medium layer with a different damaged dielectric portion than that of the hypothetical profile used to generate the first simulated diffraction signal.

13. The method of claim 12, wherein the first simulated diffraction signal is obtained from a library of simulated diffraction signals, and the different simulated diffraction signal is generated by the processor.

14. The method of claim 1 further comprising: when the measured diffraction signal and the first simulated diffraction signal do not match within a matching criterion, obtaining a different simulated diffraction signal to compare with the measured diffraction signal, wherein the different simulated diffraction signal was generated using a different hypothetical profile having at least one effective medium layer with a damaged dielectric portion that has one or more properties different than that of the effective medium layers of the hypothetical profile corresponding to the first simulated diffraction signal.

15. The method of claim 1, wherein the first simulated diffraction signal is obtained from a library of simulated diffraction signals.

16. The method of claim 1, wherein the hypothetical profile of the damaged structure corresponds to at least one deterministic characteristic of the damaged structure, and wherein processing the received diffracted beam comprises: when the measured diffraction signal and simulated diffraction signal match within a matching criterion, determining a deterministic characteristic for the damaged structure based on the at least one deterministic characteristic of the damaged structure corresponding to the hypothetical profile.

17. The method of claim 16, wherein the at least one deterministic characteristic comprises a height, a width, a thickness, a depth, a volume, an area, a dielectric property, a process recipe parameter, a processing time, a critical dimension, a spacing, a period, a position, or a line width, or a combination of two or more thereof.

18. The method of claim 17, further comprising;
performing a treating procedure on the semiconductor wafer, wherein the treating procedure comprises a healing process, a sealing process, or a cleaning process, or a combination of two or more thereof.

* * * * *